(12) United States Patent
Gallagher et al.

(10) Patent No.: US 10,925,834 B2
(45) Date of Patent: Feb. 23, 2021

(54) EXTENDED RELEASE PHARMACEUTICAL COMPOSITIONS OF LEVETIRACETAM

(71) Applicant: AgeneBio, Inc., Baltimore, MD (US)

(72) Inventors: Michela Gallagher, Baltimore, MD (US); Sharon Rosenzweig-Lipson, East Brunswick, NJ (US); Elsie Melsopp, Wilmington, NC (US); Jack Lawrence James, Castle Hayne, NC (US)

(73) Assignee: AgeneBio, Inc., Baltimore, MD (US)

( * ) Notice: Subject to any disclaimer, the term of this patent is extended or adjusted under 35 U.S.C. 154(b) by 0 days.

(21) Appl. No.: 15/574,824

(22) PCT Filed: May 20, 2016

(86) PCT No.: PCT/US2016/033567
§ 371 (c)(1),
(2) Date: Nov. 16, 2017

(87) PCT Pub. No.: WO2016/191288
PCT Pub. Date: Dec. 1, 2016

(65) Prior Publication Data
US 2018/0140555 A1    May 24, 2018

Related U.S. Application Data

(63) Continuation of application No. 15/160,424, filed on May 20, 2016, now Pat. No. 10,159,648.
(Continued)

(51) Int. Cl.
*A61K 9/20* (2006.01)
*A61K 9/00* (2006.01)
*A61K 31/4015* (2006.01)

(52) U.S. Cl.
CPC .......... *A61K 9/2054* (2013.01); *A61K 9/0053* (2013.01); *A61K 9/2009* (2013.01); *A61K 9/2013* (2013.01); *A61K 31/4015* (2013.01)

(58) Field of Classification Search
CPC .............. A61K 9/2054; A61K 31/4015; A61K 9/0053; A61K 9/2009; A61K 9/2013;
(Continued)

(56) References Cited

U.S. PATENT DOCUMENTS 2,701,225 A    2/1955    Lorenz et al.
4,118,396 A    10/1978   Pifferi et al.
(Continued)

FOREIGN PATENT DOCUMENTS

AU    08904016    8/2008
AU    08904021    8/2008
(Continued)

OTHER PUBLICATIONS

"The Merck Manual", 1999, Merck Research Laboratories, (12 pages).
(Continued)

*Primary Examiner* — Robert A Wax
*Assistant Examiner* — Quanglong N Truong
(74) *Attorney, Agent, or Firm* — Haley Guiliano LLP; James F. Haley, Jr.

(57) ABSTRACT

This invention relates to novel extended release pharmaceutical compositions of levetiracetam and preparations and characterizations thereof. This invention further relates to using these extended release pharmaceutical compositions of levetiracetam for the treatment of cognitive impairment associated with central nervous system (CNS) disorders in a subject in need or at risk thereof.

14 Claims, 9 Drawing Sheets

Related U.S. Application Data

(60) Provisional application No. 62/165,812, filed on May 22, 2015.

(58) Field of Classification Search
CPC .......... A61P 25/30; A61P 25/28; A61P 25/18; A61P 25/16; A61P 25/08
See application file for complete search history.

(56) References Cited

U.S. PATENT DOCUMENTS

| | | |
|---|---|---|
| 4,145,347 A | 3/1979 | L'Italien et al. |
| 4,173,569 A | 11/1979 | Banfi et al. |
| 4,221,789 A | 9/1980 | Rodriguez et al. |
| 4,372,960 A | 2/1983 | L'Italien |
| 4,476,308 A | 10/1984 | Aschwanden et al. |
| 4,558,070 A | 12/1985 | Bauer et al. |
| 4,595,695 A | 6/1986 | Ladkani et al. |
| 4,650,878 A | 3/1987 | Aschwanden et al. |
| 4,654,370 A | 3/1987 | Marriott, III et al. |
| 4,663,318 A | 5/1987 | Davis |
| 4,668,687 A | 5/1987 | Yevich et al. |
| 4,678,801 A | 7/1987 | Kurono et al. |
| 4,696,943 A | 9/1987 | Gobert et al. |
| 4,816,456 A | 3/1989 | Summers |
| 4,837,223 A | 6/1989 | Gobert et al. |
| 4,837,224 A | 6/1989 | Gobert et al. |
| 4,895,841 A | 1/1990 | Sugimoto et al. |
| 4,895,873 A | 1/1990 | Schafer |
| 4,913,906 A | 4/1990 | Friedman et al. |
| 4,914,102 A | 4/1990 | Glamkowski |
| 4,939,126 A | 7/1990 | Kurono et al. |
| 4,943,639 A | 7/1990 | Gobert et al. |
| 4,948,807 A | 8/1990 | Rosin et al. |
| 4,950,658 A | 8/1990 | Becker et al. |
| 4,981,870 A | 1/1991 | Koe |
| 5,017,613 A | 5/1991 | Aubert et al. |
| 5,019,398 A | 5/1991 | Daste |
| 5,034,402 A | 7/1991 | Aschwanden et al. |
| 5,049,586 A | 9/1991 | Ortega et al. |
| 5,061,725 A | 10/1991 | Giannessi et al. |
| 5,100,901 A | 3/1992 | Sugimoto et al. |
| 5,102,891 A | 4/1992 | Effland et al. |
| 5,106,856 A | 4/1992 | Kosley, Jr. et al. |
| 5,162,573 A | 11/1992 | Chiesi et al. |
| 5,166,181 A | 11/1992 | Cottens |
| 5,187,165 A | 2/1993 | Hamer et al. |
| 5,231,093 A | 7/1993 | Flanagan et al. |
| 5,238,945 A | 8/1993 | Perregaard et al. |
| 5,246,947 A | 9/1993 | Effland et al. |
| 5,288,758 A | 2/1994 | Vidaluc et al. |
| 5,300,517 A | 4/1994 | Hasegawa et al. |
| 5,302,593 A | 4/1994 | Alisi et al. |
| 5,338,548 A | 8/1994 | Kochinke et al. |
| 5,364,864 A | 11/1994 | Bigg et al. |
| 5,389,629 A | 2/1995 | Shutske et al. |
| 5,391,553 A | 2/1995 | Shutske et al. |
| 5,439,930 A | 8/1995 | Seredenin et al. |
| 5,440,023 A | 8/1995 | Cheng et al. |
| 5,447,952 A | 9/1995 | Wulfert et al. |
| 5,455,245 A | 10/1995 | Effland et al. |
| 5,574,046 A | 11/1996 | Chen et al. |
| 5,602,176 A | 2/1997 | Enz |
| 5,622,976 A | 4/1997 | Takasugi et al. |
| 5,663,448 A | 9/1997 | Collard et al. |
| 5,668,117 A | 9/1997 | Shapiro |
| 5,693,668 A | 12/1997 | Schirlin et al. |
| 5,744,476 A | 4/1998 | Locke et al. |
| 5,750,542 A | 5/1998 | Villalobos et al. |
| 5,856,569 A | 1/1999 | Santaniello et al. |
| 5,886,008 A | 3/1999 | Macor |
| 5,886,023 A | 3/1999 | Otomo et al. |
| 5,965,569 A | 10/1999 | Camps Garcia et al. |
| 5,965,571 A | 10/1999 | Hutchinson |
| 5,985,864 A | 11/1999 | Imai et al. |
| 6,131,106 A | 10/2000 | Steele, Jr. |
| 6,140,321 A | 10/2000 | Imai et al. |
| 6,245,911 B1 | 6/2001 | Imai et al. |
| 6,277,866 B1 | 8/2001 | Takeuchi et al. |
| 6,372,760 B1 | 4/2002 | Kato et al. |
| 6,479,523 B1 | 11/2002 | Puskas |
| 6,495,700 B1 | 12/2002 | Bruening |
| 6,555,544 B2 | 4/2003 | Francois et al. |
| 6,610,326 B2 | 8/2003 | Chen et al. |
| 6,620,802 B1 | 9/2003 | Schatzberg et al. |
| 6,706,741 B2 | 3/2004 | Iimura et al. |
| RE39,198 E | 7/2006 | Strupczewski et al. |
| 7,090,985 B2 | 8/2006 | Lynch et al. |
| 7,091,218 B1 | 8/2006 | Iimura et al. |
| 7,378,425 B2 | 5/2008 | Iimura et al. |
| 7,544,705 B2 | 6/2009 | Farina et al. |
| 7,557,137 B2 | 7/2009 | Decicco et al. |
| 7,563,808 B2 | 7/2009 | Pratt |
| 7,635,709 B2 | 12/2009 | Korsten et al. |
| 7,678,808 B2 | 3/2010 | Barlow et al. |
| 7,732,162 B2 | 6/2010 | Hoffman et al. |
| 7,846,930 B2 | 12/2010 | Keith |
| 7,858,611 B2 | 12/2010 | Barlow et al. |
| 7,863,316 B2 | 1/2011 | Kshisagar |
| 8,058,291 B2 | 11/2011 | Went et al. |
| 8,211,936 B2 | 7/2012 | Quere |
| 8,604,075 B2 | 12/2013 | Gallagher |
| 10,154,988 B2 | 12/2018 | Gallagher |
| 10,624,875 B2 | 4/2020 | Gallagher |
| 2001/0036949 A1 | 11/2001 | Coe et al. |
| 2002/0119963 A1 | 8/2002 | Sanner et al. |
| 2003/0069289 A1 | 4/2003 | Iimura et al. |
| 2003/0078252 A1 | 4/2003 | Sanner et al. |
| 2004/0063776 A1 | 4/2004 | Ueda et al. |
| 2004/0082644 A1 | 4/2004 | Korsten |
| 2004/0106147 A1 | 6/2004 | Lynch et al. |
| 2004/0116505 A1 | 6/2004 | Krauss et al. |
| 2004/0116506 A1 | 6/2004 | Krusz |
| 2004/0204388 A1 | 10/2004 | Lynch et al. |
| 2005/0124642 A1 | 6/2005 | Limura et al. |
| 2005/0245504 A1 | 11/2005 | Corbett et al. |
| 2006/0052428 A1 | 3/2006 | Chez |
| 2006/0063707 A1 | 3/2006 | Baudry et al. |
| 2006/0165796 A1 | 7/2006 | Kshirsagar et al. |
| 2006/0276412 A1 | 12/2006 | Tollefson |
| 2007/0031513 A1 | 2/2007 | Kikuchi |
| 2007/0135514 A1 | 6/2007 | Lynch et al. |
| 2007/0212428 A1 | 9/2007 | Wittlin |
| 2007/0213337 A1 | 9/2007 | Wacker et al. |
| 2007/0244143 A1 | 10/2007 | Barlow et al. |
| 2007/0264358 A1 | 11/2007 | Wittlin |
| 2007/0275959 A1 | 11/2007 | Verheijen et al. |
| 2007/0298098 A1 | 12/2007 | Jenkins et al. |
| 2008/0014264 A1 | 1/2008 | Goffin et al. |
| 2008/0076820 A1 | 3/2008 | Otomo et al. |
| 2008/0103105 A1 | 5/2008 | Barlow et al. |
| 2008/0167291 A1 | 7/2008 | Barlow et al. |
| 2008/0242698 A1 | 10/2008 | Flor et al. |
| 2008/0261950 A1 | 10/2008 | Rupniak et al. |
| 2008/0269316 A1 | 10/2008 | Deelers |
| 2008/0045583 A1 | 12/2008 | Delmarre et al. |
| 2009/0030403 A1* | 1/2009 | Leyde ................. G06F 19/3456 604/890.1 |
| 2009/0074854 A1 | 3/2009 | Caron et al. |
| 2009/0123541 A1 | 5/2009 | Zala |
| 2009/0124659 A1 | 5/2009 | Moebius |
| 2009/0131508 A1 | 5/2009 | Verdru |
| 2009/0176740 A1 | 7/2009 | Phillips, II |
| 2009/0306051 A1 | 12/2009 | Meyerson et al. |
| 2010/0048634 A1 | 2/2010 | Cha |
| 2010/0087422 A1 | 4/2010 | Bird |
| 2010/0099735 A1 | 4/2010 | Gallagher et al. |
| 2010/0125096 A1 | 5/2010 | Farina et al. |
| 2010/0151018 A1 | 6/2010 | Brochart et al. |
| 2010/0152108 A1 | 6/2010 | Hung et al. |
| 2010/0172979 A1 | 7/2010 | Yu et al. |
| 2010/0216734 A1 | 8/2010 | Barlow et al. |
| 2010/0227852 A1 | 9/2010 | Moebius |
| 2010/0297181 A1 | 11/2010 | Hanada |
| 2010/0311697 A1 | 12/2010 | Went et al. |

(56) References Cited

U.S. PATENT DOCUMENTS

| | | | |
|---|---|---|---|
| 2011/0206767 | A1 | 8/2011 | Zala |
| 2011/0212928 | A1 | 9/2011 | Gallagher |
| 2011/0262442 | A1 | 10/2011 | Hamilton |
| 2011/0319449 | A1 | 12/2011 | Ahmad |
| 2012/0028961 | A1 | 2/2012 | Allen |
| 2012/0046336 | A1 | 2/2012 | Gallagher et al. |
| 2012/0142729 | A1 | 6/2012 | Dounay |
| 2012/0171125 | A1 | 7/2012 | Kenda et al. |
| 2012/0214859 | A1 | 8/2012 | Gallagher et al. |
| 2012/0245215 | A1 | 9/2012 | Quere |
| 2014/0044780 | A1 | 2/2014 | Sue et al. |
| 2014/0206667 | A1 | 7/2014 | Gallagher |
| 2015/0094352 | A1 | 4/2015 | Gallagher et al. |
| 2015/0313876 | A1 | 11/2015 | Gallagher |
| 2016/0030391 | A1 | 2/2016 | Gallagher et al. |
| 2018/0015109 | A1 | 1/2018 | Gallagher |
| 2018/0140555 | A1 | 5/2018 | Gallagher |

FOREIGN PATENT DOCUMENTS

| | | |
|---|---|---|
| CA | 2180703 | 1/1998 |
| CN | 101647789 | 8/2011 |
| EP | 162036 | 11/1985 |
| EP | 0165919 | 12/1985 |
| EP | 0381959 | 8/1990 |
| EP | 0236684 | 5/1992 |
| EP | 0298202 | 8/1994 |
| EP | 0611769 | 8/1994 |
| EP | 0409676 | 3/1995 |
| EP | 0411534 | 3/1995 |
| EP | 0487071 | 7/1995 |
| EP | 0477903 | 4/1996 |
| EP | 0468187 | 3/1998 |
| EP | 1050303 | 11/2000 |
| EP | 0481429 | 1/2001 |
| EP | 1731149 | 12/2006 |
| EP | 1878844 | 1/2008 |
| EP | 2018874 | 1/2009 |
| EP | 2260839 | 12/2010 |
| EP | 2486918 | 8/2012 |
| EP | 2533645 | 7/2016 |
| JP | 4-187674 | 7/1992 |
| JP | 7-252216 | 10/1995 |
| JP | 2000-319257 | 11/2000 |
| JP | 2001-139547 | 5/2001 |
| RU | 2359675 C2 | 6/2009 |
| WO | WO1988008708 | 11/1988 |
| WO | WO1991003467 | 3/1991 |
| WO | WO1992017475 | 10/1992 |
| WO | WO1992019238 | 11/1992 |
| WO | WO1993003034 | 2/1993 |
| WO | WO1993003041 | 2/1993 |
| WO | WO1993007140 | 4/1993 |
| WO | WO1993013100 | 7/1993 |
| WO | WO1993016690 | 9/1993 |
| WO | WO1994019356 | 9/1994 |
| WO | WO1994020476 | 9/1994 |
| WO | WO1994029255 | 12/1994 |
| WO | WO1994029272 | 12/1994 |
| WO | WO1996040682 | 12/1996 |
| WO | WO1997008146 | 3/1997 |
| WO | WO1997013754 | 4/1997 |
| WO | WO1997019059 | 5/1997 |
| WO | WO1997021681 | 6/1997 |
| WO | WO1997029750 | 8/1997 |
| WO | WO1997038993 | 10/1997 |
| WO | WO1998003510 | 1/1998 |
| WO | WO1998030243 | 7/1998 |
| WO | WO1998039000 | 9/1998 |
| WO | WO1999007359 | 2/1999 |
| WO | WO1999008672 | 2/1999 |
| WO | WO1999047131 | 9/1999 |
| WO | WO2000002549 | 1/2000 |
| WO | WO2000007600 | 2/2000 |
| WO | WO2000009483 | 2/2000 |
| WO | WO2000015205 | 3/2000 |
| WO | WO2000023057 | 4/2000 |
| WO | WO2000030446 | 6/2000 |
| WO | WO2000033840 | 6/2000 |
| WO | WO2001000215 | 1/2001 |
| WO | WO2001021590 | 3/2001 |
| WO | WO200139779 | 6/2001 |
| WO | WO2001066096 | 9/2001 |
| WO | WO2001066114 | 9/2001 |
| WO | WO2001078728 | 10/2001 |
| WO | WO2002032412 | 4/2002 |
| WO | WO2002074293 | 9/2002 |
| WO | WO2003020289 | 3/2003 |
| WO | WO2003032981 | 4/2003 |
| WO | WO2003082794 | 10/2003 |
| WO | WO2003082820 | 10/2003 |
| WO | WO2003091220 | 11/2003 |
| WO | WO2003101458 | 12/2003 |
| WO | WO2004032929 | 4/2004 |
| WO | WO2004034963 | 4/2004 |
| WO | WO2004037234 | 5/2004 |
| WO | WO2004052348 | 6/2004 |
| WO | WO2004080393 | 9/2004 |
| WO | WO2004084884 | 10/2004 |
| WO | WO2004105682 | 12/2004 |
| WO | WO2005027975 | 3/2005 |
| WO | WO2005035523 | 4/2005 |
| WO | WO2005039580 | 5/2005 |
| WO | WO2005072713 | 8/2005 |
| WO | WO2005074535 | 8/2005 |
| WO | WO2005079789 | 9/2005 |
| WO | WO2005092009 | 10/2005 |
| WO | WO2005108358 | 11/2005 |
| WO | WO2005121082 | 12/2005 |
| WO | WO2006040688 | 4/2006 |
| WO | WO2006044176 | 6/2006 |
| WO | WO2006060082 | 6/2006 |
| WO | WO2006070394 | 7/2006 |
| WO | WO2006071274 | 7/2006 |
| WO | WO2006097588 | 9/2006 |
| WO | WO2006113937 | 10/2006 |
| WO | WO2007019312 | 2/2007 |
| WO | WO2007104035 | 9/2007 |
| WO | WO2007107846 | 9/2007 |
| WO | WO2007127474 | 11/2007 |
| WO | WO2008006528 | 1/2008 |
| WO | WO2008062446 | 5/2008 |
| WO | WO2008073452 | 6/2008 |
| WO | WO2008074896 | 6/2008 |
| WO | WO2008095221 | 8/2008 |
| WO | WO2008097546 | 8/2008 |
| WO | WO2009008769 | 1/2009 |
| WO | WO2009011412 | 1/2009 |
| WO | WO2009038412 | 3/2009 |
| WO | WO2009109547 | 9/2009 |
| WO | WO2010006929 | 1/2010 |
| WO | WO2010015029 | 2/2010 |
| WO | WO2010057088 | 5/2010 |
| WO | WO2010057870 | 5/2010 |
| WO | WO2010086315 | 8/2010 |
| WO | WO2010089372 | 8/2010 |
| WO | WO2011015349 | 2/2011 |
| WO | WO2011100373 | 8/2011 |
| WO | WO2011143721 | 11/2011 |
| WO | WO2012070785 | 5/2012 |
| WO | WO2012109491 | 8/2012 |
| WO | WO2012159609 | 11/2012 |
| WO | WO2013007698 | 1/2013 |
| WO | WO2014078568 | 5/2014 |
| WO | WO2014144546 | 9/2014 |
| WO | WO2014144663 | 9/2014 |
| WO | WO2014144801 | 9/2014 |

OTHER PUBLICATIONS

Aarts et al., "Selective cognitive impairment during focal and generalized epileptiform EEG activity," Brain, 107(Pt. 1):293-308 (1984).

(56) References Cited

OTHER PUBLICATIONS

Abou-Khalil, "Benefit-risk assessment of levetiracetam in the treatment of partial seizures," Drug Safety, 28(10):871-890 (2005).
Abou-Khalil, "Levetiracetam in the treatment of epilepsy," Neuropsychiatric Disease and Treatment, 4(3):507-523 (2008).
Adam et al., "Symptomatic Treatment of Huntington Disease," The Journal of the American Society for Experimental NeuroTherapeutics 5(2):181-197 (2008).
ADR news: Levetiracetam. Parkinsonism: case report. Reactions (Nov. 30, 2006) ISSN:0114-9954 (1 page).
Aeby et al., "Levetiracetam efficacy in epileptic syndromes with continuospikes and waves during slow sleep: experience in 12 cases," Epilepsia, 46(12):1937-1942 (2005).
Agam et al., "Levetiracetam does not interfere with attention to novel and targeted stimuli: An psychophysiological study," Neurology, 68(12), S1, p. 06.051 (2007) (Abstract).
Aisen et al., "Clinical Core of the Alzheimer's Disease Neuroimaging Initiative: progress and plans," Alzheimer's & Dementia, 6(3):239-246 (2010).
Albert et al., "The diagnosis of mild cognitive impairment due to Alzheimer's disease: Recommendations from the National Institute on Aging-Alzheimer's Association workgroups," Alzheimer's & Dementia 1-10 (2011).
Aldenkamp et al., "Newer antiepileptic drugs and cognitive issues," Epilepsia, 44(S4):21-29 (2003).
Altenmüller et al., "Termination of absence statepilepticby low-dose intravenolevetiracetam—a case report," Epilepsia, 48(S6):336, p. 3.238 (2007) (Abstract).
Arcas et al., "Levetiracetaminn children and adolescents with refractory epilepsy: A clinical experience," Epilepsia, 47(S3):179 Absp696 (2006) (Abstract).
Asconapé, "Some common issues in the use of antiepileptic drugs," Seminars in Neurology, 22(1):27-39 (2002).
Ashe et al., "Probing the biology of Alzheimer's disease in mice," Neuron. 66:631-645 (2010).
Bakker et al., "Response of the medial temporal lobe network in amnestic mild cognitive impairment to therapeutic intervention assessed by fMRI and memory task performance," NeuroImage Clinical, 21(7):688-698 (2015).
Bakker et al., "Reduction of hippocampal hyperactivity improves cognition in amnestic mild cognitive impairment," Neuron, 74(3):467-474 (2012).
Banfi et al., "Cyclic GABA-GABOB analogs. IV. Activity on learning and memory," Farmaco, Edizione Scientifica, 39(1):16-22 (1984).
Barner et al., "Donepezil use in Alzheimer disease," Ann. Pharmacotherapy, 32:70-77 (1998).
Bartolini et al., "Aniracetam restores object recognition impaired by age, scopolamine, and nuclebasalis lesions," Pharmacol. Biochem. Behav., 53(2):277-283 (1996).
Bartolini et al., "Effect of scopolamine and nootropic drugs on rewarded alternation in a T-maze," Pharmacol. Biochem. Behav., 43(4):1161-1164 (1992).
Béatrice Brunner et al., Neurocognitive effects of antiepileptic drugs frequently used in long term treatement of epilepsies: A review, Epileptologie, 25:118-130 (2008).
Bennett, "Seletracetam (UCB 44212)," Neurotherapeutics: The Journal of the American Society for Experimental NeuroTherapeutics, 117-122 (2007).
Berchtold et al., "Brain gene expression patterns differentiate mild cognitive impairment from normal aged and Alzheimer's disease," Neurobiology of Aging, S0197-4580(14)00289-9 (2014).
Bernhard et al., "Levetiracetam add-on treatment for bipolar patients suffering from subsyndromal symptoms: preliminary data of an open 6-months longitudinal study," European Neuropsychopharmacology, Elsevier Science Publisher BV, NL, S416 p. 2055 (1 page) (2005).
Bertolucci et al., "Proposta de uma versão brasileira para a escala adcs-cgic," Arq Neuropsiquiatr 61(3-B):881-890 (2003) (Portuguese language, English Abstract only).

Bhattacharya et al., "Latency of memory consolidation induced in mice by piracetam, a nootropic agent," Indian J Exp. Biol., 31(11):898-901 (1993).
Boido et al., "Cortico-hippocampal hyperexcitability in synapsin IIIII knockout mice: age-dependency and response to the antiepileptic drug levetiracetam," Neuroscience, 171(1):268-283 (2010).
Bootsma et al., "The effect of antiepileptic drugs on cognition: patient perceived cognitive problem of topiramate verslevetiracetam in clinical practice," Epilepsia, 47(S2):24-27 (2006).
Bora et al., "Theory of mind impairment: a distinct trait-marker for schizophrenia spectrum disorders and bipolar disorder?" Acta Psychiatr Scand., 120 (12 pages) (2009).
Bores et al., "Galanthamine derivatives for the treatment of alzheimer's disease," Drugs of the future, 21(6):15—(1996).
Bottini et al., "Oxiracetam in dementia: a double-blind, placebo-controlled study," Acta. Neurol. Scand., 86(3):237-241 (1992).
Bourgeois, "Determining the effects of antiepileptic drugs on cognitive function in pediatric patients with epilepsy," Journal of Child Neurology, 19(S1):S15-S24 (2004).
Brandt et al., "Prophylactic treatment with levetiracetam after statepilepticus: lack of effect on epileptogenesis, neuronal damage, and behavioral alterations in rats," Neuropharmacology, 53(2):207-221 (2007).
Bridgman et al., "Memory during subclinical hippocampal seizures," Neurology, 39(6):853-856 (1989).
Brown et al., "Impact of levetiracetam on mood and cognition during prednisone therapy," European Psychiatry, 22(7):448-452 (2007).
Buschke et al., "Evaluating storage, retention, and retrieval in disordered memory and learning," Neurology, 24:1019-1025 (1974).
Butler et al., "Amnesia-reversal activity of a series of N-[(disubstituted-amino)alkyl]-2-oxo-1-pyrrolidineacetamides, including pramiracetam," Journal of Medicinal Chemistry, 27:684-691 (1984).
Campos-Castello, "Neuropsychology and epilepsy," Revista de Neurologia, 39(2):166-177 (2004) (English Abstract only).
Carreno et al., "Cognitive disorders associated with epilepsy: Diagnosis and treatment," The Neurologist, 14(6S):S26-S34 (2008).
Cavoy et al., "Relationships between arousal and cognition-enhancing effects of oxiracetam," Pharmacol. Biochem. Behav., 47(2):283-287 (1994).
Cercy et al., "Gelastic epilepsy and dysprosodia in a case of late-onset right frontal seizures," Epilepsy & Behavior, 16(2):360-365 (2009).
Chaisewikul et al., "Levetiracetam add-on for drug-resistant localization related (partial) epilepsy (review)," Cochrane Database of Systematic Reviews Issue 1 (2010).
Chang et al., "SV2 renders primed synaptic vesicles competent for Ca2+-induced exocytosis," Journal of Neuroscience, 29(4):883-897 (2009).
Chappell et al., "A re-examination of the role of basal forebrain cholinergic neurons in spatial working memory," Neuropharmacology, 37(4-5):481-487 (1998).
Chen, Yangmei et al., "Epilepsy Therapeutics," Sichuan Publishing Group, Sichuan Science and Technology Press, Jun. 2004 (Full-text English translation).
Cicolin et al., "[Levetiracetam and cognitive functions: A single blind, crossover, placebo controlled study in healthy volunteers]," Bolletinno Lega Italiana control'Epilessia, No. 113-114:79-81 (2001) (English Abstract only).
Ciesielski et al., "Neuropsychological and psychiatric impact of add-on titration of pregabalin verslevetiracetam: A comparative study," Epilepsia, 47(S3):Absp518 (2006).
Claus al., "Nootropic drugs in Alzheimer's disease: symptomatic treatment with pramiracetam," Neurology, 41(4):570-574 (1991).
Coras et al., "Low proliferation and differentiation capacities of adult hippocampal stem cells correlate with memory dysfunction in humans," Brain, 133(11):3359-3372 (2010).
Cramer et al., "A systematic review of the behavioral effects of levetiracetam in adults with epilepsy, cognitive disorders, or an anxiety disorder during clinical trials," Epilepsy & behavior, 4(2):124-132 (2003).
Cramer et al., "Effect of levetiracetam on epilepsy-related quality of life. N132 Study Group," Epilepsia, 41(7):868-874 (2000).

(56) References Cited

OTHER PUBLICATIONS

Cramer et al., "Tolerability of levetiracetam in elderly patients with CNS disorders," Epilepsy Research, 56(2-3):135-145 (2003).

Croisile et al., "Long-term and high-dose piracetam treatment of Alzheimer's disease," Neurology, 43(2):301-305 (1993).

Crook et al., "Age-associated memory impairment: Proposed diagnostic criteria and measures of clinical change—Report of a National Institute of Mental Health workgroup," Developmental Neuropsychology, 2:261-276 (1986).

Cumbo et al., "Levetiracetam, lamotrigine, and phenobarbital in patients with epileptic seizures and Alzheimer's disease," Epilepsy & Behavior, 17(4):461-466 (2010).

Cumbo, "Effects of levetiracetam, phenobarbital and lamotrigine on neuropsychological performance and mood in patients with alzheimer's disease and epilepsy," Epilepsia, 50(S4):101-102 (2009).

Czubak et al., "Cognitive effects of GABAergic antiepileptic drugs," Arzneimittel-Forschung, 60:(1)1-11 (2010).

De Smedt et al., "Levetiracetam: the profile of a novel anticonvulsant drug—part I: preclinical data," CNS Drug Review, 13(1):43-56 (2007).

De Vreese et al., "Memory training and drug therapy act differently on memory and metamemory functioning: evidence from a pilot study," Arch. Gerontol. Geriatr., 22(S 1):9-22 (1996).

Detrait et al., "Brivaracetam does not alter spatial learning and memory in both normal and amygdala-kindled rats," Epilepsy Research, 91(1):74-83 (2010).

Detrait et al., "Brivaracetam does not impair cognitive performance of rats in the morris water maze test," Epilepsia, 49(S7):111, p. 1.253 (2008) (Abstract).

Detrait et al., "Brivaracetam does not impair cognitive performance in normal and kindled rats," Epilepsia, 50(S10):96, p. 450 (2009) (Abstract).

Diaz Negrillo et al., "[Levetiracetam efficacy in patients with Lennox-Gastaut syndrome. Presentation of a case]," Neurologia, 26(5):285-290 (2011) (Spanish language article, English Abstract Only).

Dietrich et al., "Clinical patterns and biological correlates of cognitive dysfunction associated with cancer therapy," Oncologist, 13:1285-1295 (2008).

Dinapoli et al., "Quality of life and seizure control in patients with brain tumor-related epilepsy treated with levetiracetam monotherapy: preliminary data of an open-label study," Neurological Sciences, 30(4):353-359 (2009).

Doheny et al., "Blood and cerebrospinal fluid pharmacokinetics of the novel anticonvulsant levetiracetam (ucb L059) in the rat," Epilepsy Research, 34: 161-168 (1999).

Dyzdarer et al., "Levetiracetam in the treatment of refractory epilepsy in children," Epilepsia, 50(S 4)244:AbsE720 (2009) (Abstract).

Eddy, et al. "The cognitive impact of antiepileptic drugs," Therapeutic Advances in Neurological Disorders, 4(6):385-407 (2011).

Edelbroek et al., "Evaluation of the pharmacokinetic and neuropsychometric parameters in chronic comedicated epileptic patients of three increasing dosages of a novel, antiepileptic drug, UCB L059 250-mg capsules per Os each dose for one week followed by two-weeks of placebo," Epilepsia, 34(S2):7 (1993) (Abstract).

Ehtisham et al., "Cognitive outcomes following seizure prophylaxis for intracranial hemorrhages of different subtypes with levetiracetam versphenytoin," Annals of Neurology, 64(S12):S30, M-110 (2008).

Ennaceur et al., "A new one-trial test for neurobiological studies of memory in rats. II: Effects of piracetam and pramiracetam," Behav. Brain Research, 33(2):197-207 (1989).

Estimating the Safe Starting Dose in Clinical Trials for Therapeutics in Adult Healthy Volunteers, Dec. 2002, Center for Biologics Evaluation and Research.

Farlow, "Treatment of Mild Cognitive Impairment (MCI)," Current Alzheimer Research, 6:362-367 (2009).

Fattouch et al., "IntravenoLevetiracetam as first-line treatment of statepilepticin the elderly," Acta. Neurol. Scand., 121(6):418-421 (2010).

Fauser et al., "Effect of levetiracetam in limbic encephalitis: A case report," Epilepsia, 44(S 8):111-112 p. 298 (2003) (Abstract).

Fedi et al., "Long-term efficacy and safety of piracetam in the treatment of progressive myoclonepilepsy," Arch. Neurol., 58(5):781-786 (2001).

Feleppa et al., "Epileptogenic KLUVER-BUCY syndrome (EKBS) treated with nasogastric levetiracetam (LVT) as adjunctive therapy: A case of excellent neurological recovery at 4 months after discharge," European Journal of Neurology, 14(S1):214 Absp2206 (2007) (Abstract).

Firstova et al., "Effects of nootropic drugs on hippocampal and cortical BDNF levels in mice with different exploratory behavior efficacy," Eksperimental'naya i Klinicheskaya Farmakologiya, 72(6):3-6 (2009) (English Abstract only).

French et al., "A systematic review of the safety profile of levetiracetam: a new antiepileptic drug," Epilepsy Research, 47(1-2):77-90 (2001).

French et al., "Levetiracetam overall safety profile," Epilepsia, 42(S7):151 (2001).

Frings et al., "Early detection of behavioral side effects of antiepileptic treatment using handheld computers," Epilepsy & Behavior, 13(2):402-406 (2008).

Frings et al., "Effects of add-on treatment with levetiracetam on cognition in epilepsy patients," Epilepsia, 44, S 8, p. 111, p. 297 (2003) (Abstract).

Fritz et al., "Effects of add-on treatment with topiramate or levetiracetam on cognition and health related quality of life in patients with epilepsy," European Journal of Neurology, 12 (S2):121 p. 1341 (2005) (Abstract).

Fritz et al., "Effects of add-on treatment with topiramate or levetiracetam on cognition and health related quality of life for patients with epilepsy," Epilepsia, 46(S6):106-107 (2005) (Abstract).

Frostl et al., "The families of cognition enhancers," Pharmacopsychiatry, 22(2):54-100 (1989).

Gallai et al., "A clinical and neurophysiological trial on nootropic drugs in patients with mental decline," Acta. Neurol. (Napoli), 13(1):1-12 (1991).

Gamzu et al., "Drug improvement of cognition: Hope and reality," Psychiatric et Psychobiologie, 3(No. SPEC. ISS B):115-123 (1988).

Gamzu et al., "Recent developments in 2-pyrrolidinone-containing nootropics," Drug Development Research, 18(3):177-189 (1989).

Gamzu, "Animal behavioral models in the discovery of compounds to treat memory dysfunction," Annals of the New York Academy of Sciences, 444:370-393 (1985).

Garcia-Penas et al., "Efficacy and safety of levetiracetam monotherapy for children with epilepsy," Epilepsia, 48(S7):150 Absp390 (2007) (Abstract).

Gaudenzi et al., "[Levetiracetam therapy in patients with epilepsy and dementia]," Bollettino—Lega Italiana contro l'Epilessia, 125-126:215-216 (2004) (English Abstract only).

Genton et al., "Piracetam and levetiracetam: close structural similarities but different pharmacological and clinical profiles," Epileptic disorders, 2( 2):99-105 (2000) (Abstract).

Gevins et al., "Neuropsychological and neurophysiological effects of carbamazepine and levetiracetam," Epilepsia, 47(S4):157-158,p. 2112 (2006).

Ghelardini et al., "The novel nootropic compound DM232 (unifiram) ameliorates memory impairment in mice and rats," Drug Development Research, 56:23-32 (2002).

Gillard et al., "Binding characteristics of brivaracetam, a selective, high affinity SV2A ligand in rat, mouse and human brain: relationship to anti-convulsant properties," European Journal of Pharmacology, 664:36-44 (2011).

Glien et al., "Effects of the novel antiepileptic drug levetiracetam on spontaneorecurrent seizures in the rat pilocarpine model of temporal lobe epilepsy," Epilepsia, 43(4):350-357 (2002).

Goldberg et al., "Cognitive side effects of anticonvulsants," Journal of Clinical Psychiatry, 62(S14):27-33 (2001).

Gomer et al., "The influence of antiepileptic drugs on cognition: a comparison of levetiracetam with topiramate," Epilepsy & Behavior, 10(3):486-494 (2007).

Gouliaev et al., "Piracetam and other structurally related nootropics," Brain Research Review, 19(2):180-222 (1994).

(56) References Cited

OTHER PUBLICATIONS

Green et al., "Treatment trial of oxiracetam in Alzheimer's disease," Arch. Neurol., 49(11):1135-1136 (1992).
Gualtieri et al., "Design and study of piracetam-like nootropics, controversial members of the problematic class of cognition-enhancing drugs," Current Pharmaceutical Design, 8(2):125-138 (2002).
Guido et al., "Event-related potential sin the evaluation of the effect of levetiracetam and carbamazepine on cognitive functions in newly diagnosed epilepsy patients; preliminary results of a randomized trial," Epilepsia, 48(S7):107, p. 244 (2007) (Abstract).
Guido et al., "Event-related potentials (ERPs) in the evaluation of the effect of levetiracetam and carbamazepine on cognitive functions in adult patients with newly diagnosed epilepsy," European Journal of Neurology, 15(S3):305 (2008) (Abstract).
Guo et al., "Effects of levetiracetam on quality of life in children with refractory epilepsy," Changjiang Daxue Xuebao, Ziran Kexueban, 8(1):151-155 (2011) (English Abstract only).
Haber et al., "Cognitive effects of levetiracetam in patients treated for interactable epilepsy," Epilepsia, 47( S4):97-98, p. 1.197 (2006) (Abstract).
Halgren et al., "Recall deficits produced by afterdischarges in the human hippocampal formation and amygdale," Electroencephalogr. Clin. Neurophysiol., 61(5):375-380 (1985).
Hamann et al., "Brivaracetam and seletracetam, tWOnew SV2A ligands, improve paroxysmal dystonia in the dtsz mutant hamster," European Journal of Pharmacology, 601:99-102 (2008).
Hamed, "The aspects and mechanisms of cognitive alterations in epilepsy: the role of antiepileptic medications," CNS Neuroscience & Therapeutics, 15(2):134-156 (2009).
Hassel et al., "Up-regulation of hippocampal glutamate transport during chronic treatment with sodium valproate," Journal of Neurochemistry, 77:1285-1292 (2001).
Heidegger et al., "Effects of antiepileptic drugs on associative LTP-like plasticity in human motor cortex," European Journal of Neuroscience, 32:1215-1222 (2010).
Helmstaedter et al., "Cognitive outcome of antiepileptic treatment with levetiracetam verscarbamazepine monotherapy: a non-interventional surveillance trial," Epilepsy & Behavior, 18(1-2):74-80 (2010).
Helmstaedter et al., "Positive and negative psychotropic effects of levetiracetam," Epilepsy & Behavior, 13(3):535-541 (2008).
Helmstaedter et al., "The effects of levetiracetam on cognition: a non-interventional surveillance study," Epilepsy & Behavior, 13(4):642-649 (2008).
Helmstaedter, "'Real life' cohort study on levetiracetam verscarbamazepine monotherapy: a controlled surveillance study," Epilepsia, 50(S10):100, p. 465 (2009) (Abstract).
Helmstaedter, "'real life' cohort study on levetiracetam verscarbamazepine monotherapy—a controlled surveillance study on cognition," Epilepsia, 50(S6):47, p. 210 (2009) (Abstract).
Herholz et al., "Discrimination between Alzheimer dementia and controls by automated analysis of multicenter FDG PET," NeuroImage, 17:302-316 (2002).
Hermann et al., "Cognition across the lifespan: antiepileptic drugs, epilepsy, or both?" Epilepsy Behavior, 17:1-5 (2010).
Herranz et al., "Effectiveness and tolerability of levetiracetam in 43 children and adolescents with epilepsy," Revisa de neurologia, 37(11):1005-1008 (2003) (English Abstract only).
Herranz et al., "Levetiracetam: efficacy and tolerability in children and adolescents with epilepsy," Epilepsia, 44(S 8):152, p. 457 (2003) (Abstract).
Herranz et al.,"Effectiveness and safety of levetiracetam in 133 children with medication resistant epileptic seizures," Revista de neurologia, 43(7):393-397 (2006) (English Abstract only).
Higgins et al., "Comparative study of five antiepileptic drugs on a translational cognitive measure in the rat: relationship to antiepileptic property," Psychopharmacology, 207(4):513-527 (2010).

Himi et al., "Levetiracetam prevents attentional deficits induced by bilateral common artery occlusion in mice," Epilepsia, 48(S6):323, 3.203 (2007) (Abstract).
Himi et al., "Levetiracetam prevents the attention deficit induced by bilateral carotid artery occlusion in mice," Journal of Pharmacological Sciences, 109(S1):226P (2009) (English Abstract only).
Hlinak et al., "Kynurenic acid and 5,7-dichlorokynurenic acids improve social and object recognition in male rats," Psychopharmacology (Berl), 120(4):463-469 (1995).
Hlinak et al., "Oxiracetam prevented the scopolamine but not the diazepam induced memory deficits in mice," Behav. Brain Research, 133(2):395-399 (2002).
Huang et al., "Comparative cognitive effects of levetiracetam and topiramate in intractable epilepsy," Psychiatry and Clinical Neurosciences, 62(5):548-553 (2008).
Ioannidis et al., "Transient epileptic amnesia in a memory clinic setting: A report of three cases," Epilepsy and Behavior, 20(2):414-417 (2011).
Irizaary et al., "Incidence of new-onset seizures in mild to moderate Alzheimer disease," Arch. Neurol., 69(3):368-372 (2012).
Israel et al., "Drug therapy and memory training programs: A double-blind randomized trial of general practice patients with age-associated memory impairment," International Psychogeriatrics, 6(2):155-170 (1994).
Ito et al., "A case series of epilepsy-derived memory impairment resembling Alzheimer disease," Alzheimer Dis. Assoc. Disord., 23(4):406-409 (2009).
Ito et al., "The efficiency of donepezil in Alzheimer's Disease," J. Nippon Med Sch, 69(4): 379-382 (Japanese language, English Abstract).
Jelic et al., "Clinical trials in mild cognitive impairment: lessons for the future," J. Neurol. Neurosurg. Psychiatry., 77(4):429-438 (2006).
Jetter et al., "Epilepsy in the elderly," Seminars in Neurology, 28(3):336-341 (2008).
Junemann et al., "Cognitive performance in patients with focal and primary generalized epilepsy under levetiracetam or topiramate monotherapy: a prospective pseudo-randomized study," Epilepsia,50(S6):47, p. 209 (2009) (Abstract).
Kaindl et al., "Antiepileptic drugs and the developing brain," Cellular and Molecular Life Sciences, 63(4): 399-413 (2006).
Kalinin, "Suicidality and antiepileptic drugs. Is there a link?" Drug Safety, 30(2):123-142 (2007).
Kamada Kyousuke, "Are clinical features derived from evidences and experiences outside of Japan applicable to clinical practices in Japan? Comparisons of results among studies conducted in US, Europe, Asian Countries and Japan," Brain and nerve = Shinkei kenkyu no shinpo, 63(3):247-54 (2011) (English Abstract only).
Kasteleijn-Nolst Trenite et al., "On-line detection of transient neuropsychological disturbances during Eeg discharges in children with epilepsy," Dev. Med. Child Neurol., 32(1):46-50 (1990).
Kenda et al., "Discovery of 4-Substituted Pyrrolidone Butanamidesas New Agents with Significant Antiepileptic Activity," Journal of Medicinal Chemistry, 47(3):530-549 (2004).
Khan et al., "Topiramate attenuates exaggerated acoustic startle in an animal model of PTSD," Psychopharmacology 172:225-229 (2004).
Kilgore et al., "Inhibitors of class 1 histone deacetylases reverse contextual memory deficits in a mouse model of Alzheimer's disease," Neuropsychopharmacology, 35:870-880 (2010).
Kim et al., "Transient impairment of hippocampus-dependent learning and memory in relatively low-dose of acute radiation syndrome is associated with inhibition of hippocampal neurogenesis," J. Radiat. Res., 49:517-526 (2008).
Klatte et al., "The quality of life with levetiracetam in benign rolandic epilepsy," Epilepsia, 49 (S7):220, p. 2.108 (2008) (Abstract).
Klitgaard et al., "Evidence for a unique profile of levetiracetam in rodent models of seizures and epilepsy," Eur. J. Pharmacol., 353(2-3):191-206 (1998).
Klitgaard et al., "Use of epileptic animals for adverse effect testing," Epilepsy Research, 50(1-2):55-65 (2002).
Kobayashi et al. "Behavioral phenotypes of amyloid-based genetically modified mouse models of Alzheimer's disease," Genes Brain Behav., 4:173-196 (2005).

(56) References Cited

OTHER PUBLICATIONS

Koh et al., "Treatment strategies targeting excess hippocampal activity benefit aged rats with cognitive impairment," Neuropsychopharmacology, 35(4):1016-1025 (2010).
Kong et al., "Effect of antiepileptic drugs on cognitive functions and expressions of glutamate receptor 2 and synaptophysin of the hippocampin rats," Journal of Shandong University (Health Science), 48(7):14-18 (2010) (Chinese language, English Abstract).
Kooi et al., "Alterations in mental function and paroxysmal cerebral activity," AMA Arch Neurol. Psychiarty, 78(3):264-271 (1957).
Kopp et al., "Cognitive side affects of levetiracetam in monotherapy: comparison with carbamazepine and valproate," Epilepsia, 48(S3):39-40 (2007) (Abstract).
Kossoff et al., "A pilot study transitioning children onto levetiracetam monotherapy to improve language dysfunction associated with benign rolandic epilepsy," Epilepsy & Behavior, 11(4):514-517 (2007).
Krakow et al., "Effects of antiepileptic drugs on cortical plasticity and motor learning: A double blind, placebo-controlled transcranial magnetic stimulation study," Epilepsia, 46(8):212-213 (2005).
Lagae et al., "Clinical experience with levetiracetam in childhood epilepsy: an add-on and mono-therapy trial," Seizure, 14:66-71 (2005).
Lagae et al., "Effect of levetiracetam on behavior and alertness in children with refractory epilepsy," Epilepsia, 44(S9):92, p. 1.258 (2003) (Abstract).
Lagae, "Cognitive side effects of anti-epileptic drugs. The relevance in childhood epilepsy," Seizure, 5(4):235-241 (2006).
Lamberty et al., "Absence of negative impact of levetiracetam on cognitive function and memory in normal and amygdala-kindled rats," Epilepsy & Behavior, 1:333-342 (2000).
Lamberty et al., "Behavioural phenotyping reveals anxiety-like features of SV2A deficient mice," Behavioural Brain Research, 198(2):329-333 (2009).
Lamberty et al., "Cognitive performance is unaltered by levetiracetam (ucb L059) in the pilocarpine model of chronic epilepsy," Epilepsia, 39(S2):85 (1998) (Abstract).
Lamberty et al., "Lack of negative impact on cognitive function differentiates levetiracetam (UCB L059) from other antiepileptic drugs," Epilepsia, 39(S6):45, p. 2.053 (1998) (Abstract).
Larrabee, "Age-Associated Memory Impairment: Definition and psychometric characteristics," Aging, Neuropsychology, and Cognition, 3:118-131 (1996).
Lebrun et al., "Effects of S 18986-1, a novel cognitive enhancer, on memory performances in an object recognition task in rats," European Journal of Pharmacology, 401(2):205-212 (2000).
Lee et al., "Levetiracetam inhibits glutamate transmission through presynaptic PQ-type calcium channels on the granule cells of the dentate gyms," British J. Pharmacol., 158:1753-1762 (2009).
Leeman et al., "Cognitive effects of treatment of focal interictal discharges with levetiracetam," Epilepsia, 49(S7):136-137, p. 1.312 (2008) (Abstract).
Levetiracetam American journal of health-system pharmacy, 57:1484 (2000) (AHFS).
Levisohn et al., "Neurocognitive effects of adjunctive levetiracetam in children with partial-onset seizures: a randomized, double-blind, placebo-controlled, noninferiority trial," Epilepsia 50(11):2377-2389 (2009).
Li, Jinjin et al., "Patient Discharge Guidance, Internal Medicine Section," Zhejiang Science and Technology Publishing House, Jun. 2007 (Full-text English translation).
Liberzon et al., "Stress-restress: effects on ACTH and fast feedback," Psychoneuroendocrinology, 22:443-453 (1997).
Liedorp et al., "Prevalence and clinical significance of epileptiform EEG discharges in a large memory clinic cohort," Dement. Geriatr. Cogn. Disord., 29(5):432-437 (2010).
Lindholm, "Levetiracetam levels correlating with successful treatment of epilepsy, headaches, cognitive effects, and adverse reactions in pediatric age group," Epilepsia, 43(S7):60 (2002) (Abstract).

Lippa et al., "Levetiracetam: a practical option for seizure management in elderly patients with cognitive impairment," American Journal of Alzheimer's Disease & Other Dementias, 25(2):149-154 (2010).
Lippa et al., "Levetiracetam: seizure management for elderly patients with cognitive impairment," Neurology, 70(11, S1) Absp02-185 (2008) (Abstract).
Lopez-Gongora et al., "Cognitive function and quality of life after six months treatment with levetiracetam (LEV)," Epilepsia, 46(S 6):156, p. 136 (2005) (Abstract).
Loring et al., "Neuropsychological and behavioral effects of antiepilepsy drugs," Neuropsychol Rev, 17(4):413-425 (2007).
Loscher, "Valproate: a reappraisal of its pharmacodynamic properties and mechanisms of action," Progress in Neurobiology, 58:31-59 (1999).
Lukyanetz et al., "Selective blockade of N-type calcium channels by levetiracetam," Epilepsia, 43(1):9-18 (2002).
Lyseng-Williamson, "Levetiracetam: a review of its use in epilepsy," Drugs, 71(4):489-514 (2011).
López-Góngora et al., "Effect of levetiracetam on cognitive functions and quality of life: a one-year follow-up study," Epileptic Disord, 10(4):297-305 (2008).
Löscher et al., "Profile of ucb L059, a novel anticonvulsant drug, in models of partial and generalized epilepsy in mice and rats," Eur. J. Pharmacol., 232(2-3):147-158 (1993).
Maggini M, Vanacore N, Raschetti R (2006) Cholinesterase Inhibitors: Drugs Looking for a Disease? PLoS Med 3(4): e140. doi:10.1371journal.pmed.0030140.
Magnani et al., "Oxiracetam antagonizes the disruptive effects of scopolamine on memory in the radial maze," Psychopharmacology (Berl), 106(2):175-178 (1992).
Maguire et al., "Epilepsy (generalised)," Neurological disorders, Clinical evidence, 6(1201):1-14 (2009).
Maguire et al., "Epilepsy (partial)," Neurological disorders,Clinical evidence, 5(1214):1-42 (2011).
Maina et al., "Oxiracetam in the treatment of primary degenerative and multi-infarct dementia: a double-blind, placebo-controlled study," Neuropsychobiology, 21(3):141-145 (1989).
Malik et al., "Towards better brain management: Nootropics," Current Medicinal Chemistry, 14:123-131 (2007).
Malykh et al., "Piracetam and piracetam-like drugs: from basic science to novel clinical applications to CNS disorders," Drugs, 70(3):287-312 (2010).
Manthey et al., "Sulthiame but not levetiracetam exerts neurotoxic effect in the developing rat brain," Experimental Neurology, 193(2):497-503 (2005).
Maresova et al., "Pramiracetam and epileptic after-discharges in young rats after hypoxia," Act. Nerv. Super (Praha), 31(1):68-69 (1989).
Marini et al., "Placebo-controlled double-blind study of pramiracetam (CI-879) in the treatment of elderly subjects with memory impairment," Advances in Therapy 9(3):136-146 (1992).
Martella et al., "Seletracetam (ucb 44212) inhibits high-voltage-activated Ca2+ currents and intracellular Ca2+ increase in rat cortical neurons in vitro," Epilepsia, 50(4):702-710 (2009).
Martinez-Coria et al., "Memantine improves cognition and reduces Alzheimer's-like neuropathology in transgenic mice," Am J Pathol, 176 (11 pages) (2010).
Mauri et al., "Pramiracetam effects on scopolamine-induced amnesia in healthy volunteers," Arch. Gerontol. Geriatr., 18(2):133-139 (1994).
Meador et al., "Cognitive and behavioral effects of carbamazepine and levetiracetam in healthy volunteers: S09.002: 2:15 pm," Neurology, 66(S2) p. A72 (2006) (Abstract).
Meador et al., "Neurocognitive effects of brivaracetam, levetiracetam, and lorazepam," Epilepsia, 52(2):264-272 (2011).
Meador et al., "Neuropsychological and neurophysiologic effects of carbamazepine and levetiracetam," Neurology, 69(22):2076-2084 (2007).
Meador, "Cognitive and memory effects of the new antiepileptic drugs," Epilepsy Research, 68(1):63-67 (2006).
Meador, "Cognitive effects of levetiracetam verstopiramate," Epilepsy Currents, 8(3):64-65 (2008).

(56) References Cited

OTHER PUBLICATIONS

Mecarelli et al., "Clinical cognitive, and neurophysiologic correlates of short-term treatment with carbamazepine, oxcarbazepine, and levetiracetam in healthy volunteers," Annual Pharmacotherapy, 38(11):1816-1822 (2004).
Mechtler et al., "Efficacy of intravenolevetiracem in the treatment of statmigrainosus," Headache, 48(S1):S45-S46, S16 (2008) (Abstract).
Mendez et al., "Seizures in Alzheimer's disease: clinicopathologic study," J. Geriatr. Psychiatry Neurol., 7(4):230-233 (1994).
Meo et al., "Use of levetiracetam monotherapy in patients with post-traumatic epilepsy: Preliminary data," Epilepsia, 47(S4):165, p. 2135 (2006) (Abstract).
Merlini et al., "Trends in searching for new cognition enhancing drugs," Progress in Neuro-Psychopharmacology and Biological Psychiatry, 13: S61-S75 (1989).
Minervini et al., "Mild cognitive impairment, focal epilepsy and levetiracetam," Epilepsia, 49(S7):110, p. 256 (2007) (Abstract).
Mintz et al., "Double-blind, placebo-controlled, non-inferiority study to evaluate the cognitive and neuropsychological effects of levetiracetam 20-60 mgkgday as adjunctive treatment versplacebo in pediatric patients with partial-onset seizures," Epilepsia, 48(S6):356, p. 3.292 (2007) (Abstract).
Mintz et al., "The effects of levetiracetam on neuropsychological functioning in relation to "subclinical" spike production," Epilepsia, 47, S4, p. 112, 1.237 (2006) (Abstract).
Mintz et al., "The underrecognized epilepsy spectrum: the effects of levetiracetam on neuropsychological functioning in relation to subclinical spike production," Journal of Child Neurology, 24(7):807-815 (2009).
Mondadori et al., "Delayed emergence of effects of memory-enhancing drugs: implications for the dynamics of long-term memory," Proceedings of the National Academy of Science USA, 91(6):2041-2045 (1994).
Mondadori et al., "Elevated corticosteroid levels block the memory-improving effects of nootropics and cholinomimetics," Psychopharmacology (Berl), 108(1-2):11-15 (1992).
Mondadori et al., "The Effects of Nootropics on Memory: New Aspects for Basic Research," Pharmacopsychiatry, 22(S 2):102-106 (1989).
Mondadori et al., "The GABAB receptor antagonist CGP 36,742 and the nootropic oxiracetam facilitate the formation of long-term memory," Behav. Brain Research, 77(1-2):223-225 (1996).
Mondadori et al., "The pharmacology of the nootropics; new insights and new questions," Behavioural Brain Research, 59(1-2):1-9 (1993).
Mula et al., "Antiepileptic Drug-Induced Cognitive Adverse Effects Potential Mechanisms and Contributing Factors," CNS Drugs, 23(2):121-137 (2009).
Murphy et al., "Chronic exposure of rats to cognition enhancing drugs produces a neuroplastic response identical to that obtained by complex environment rearing," Neuropsychopharmacology, 31(1):90-100 (2006).
Murray et al., "The effect of pramiracetam (CI-879) on the acquisition of a radial arm maze task," Psychopharmacology (Berl), 89(3):378-381 (1986).
Muscas et al., "[Efficacy and tolerability of Levetiracetam in epileptic patients with acquired progressive cognitive impairment]," Bollettino—Lega Italiana contro l'Epilessia, 129-130:233-234 (2005) (full text English translation).
Nagarkatti et al., "Levetiracetam inhibits both ryanodine and IP3 receptor activated calcium induced calcium release in hippocampal neurons in culture," 436(3):289-293 (2008).
Nakamoto et al., "Nootropic nefiracetam inhibits proconvulsant action of peripheral-type benzodiazepines in epileptic mutant EL mice," Annals New York Academy of Science, 1025:135-139 (2004).
Neyens et al., "Cognitive effects of a new pyrrolidine derivative (levetiracetam) in patients with epilepsy," Prog. Neuro-Psychopharmacol. & Biol. Psychiat., 19(3):411-419 (1995).
Neyens et al., "Cognitive side effects of levetiracetam (UCB LO59) in epilepsy," Epilepsia, 35(S7):76 (1994) (Abstract).

Nghiemphu et al., "Levetiracetam monotherapy in patients with malignant glioma," Neuro-Oncology, p. 566, QL-11 (2007).
Nicholson, "Pharmacology of nootropics and metabolically active compounds in relation to their use in dementia," Psychopharmacology, 101(No. 2):147-159 (1990).
Nicolle et al., "In vitro autoradiography of ionotropic glutamate receptors in hippocampand striatum of aged Long-Evans rats: relationship to spatial learning," Neuroscience, 74(3):741-756 (1996).
Niespodziany et al., "Levetiracetam inhibits the high-voltage-activated Ca2+ current in pyramidal neurons of rat hippocampal slices," Neuroscience Letters, 306:5-8 (2001).
Nikolova et al., "Effects of ACE-inhibitors on learning and memory processes in rats," Folia Med. (Plovdiv), 42(1):47-51 (2000).
Nygaard et al., "Brivaracetam, but not ethosuximide, reverses memory impairments in an Alzheimer's disease mouse model," Alzheimer's Research & Therapy, 7:25 (2015) (12 pages).
Onuma Teiichi, "Cognitive Dysfunction and Antiepileptic Drugs," Brain and Nerve (Tokyo), 63( 4):379-383 (2011) (Abstract— Japanese and English translation).
Owens et al., "Pharmacology of Divalproex," Psychopharmacology Bulletin 37 Suppl 2:17-24. (2003).
Padwa et al., "Cyclization-cycloaddition casade of rhodium carbenoids using different carbonyl groups. Highlighting the position of interaction," J. Org. Chem., 65:5223-5232 (2000).
Palmer et al., "Correlation between behavioural adverse events and cognitive functions in epilepsy patients receiving levetiracetam," Epilepsia, 44(S8):172, p. 537 (2003) (Abstract).
Park et al., "Increased EEG current-source density in the high Beta frequency band induced by levetiracetam adjunctive therapy in refractory partial epilepsy," Journal of Clinical Neurology (Seoul, Korea) 5(4):178-185 (2009).
Parretti et al., "Neuropsychological results of long-term therapy with oxiracetam in patients with dementia of Alzheimer type and multi-infarct dementia in comparison with a control group," Neuropsychobiology, 22(2):97-100 (1989).
Pastor et al., "Tolerability and efficacy of the combination of piracetam and citicoline in acute ischemic stroke. A randomized comparative open study," p. e286, top right-hand column, paragraph 1 of Abstract of the 5th World Stroke Conference, Jan. 2004, Retrieved from the Internet: http:stroke.ahajournals.orgcontent356e276.full.pdf#page=1$view=Fith.
Patsalos, "Pharmacokinetic profile of levetiracetam: toward ideal characteristics," Pharmacol. Ther., 85(2):77-85 (2000).
Patsalos, "Clinical pharmacokinetics of levetiracetam," Clin. Pharmacokinet., 43(11):707-724 (2004).
Paulson et al., "Effect of levetiracetam on hippocampal protein expression and cell proliferation in rats," Epilepsy Research, 90(1-2):110-120 (2010).
Perini et al., "Use of valproate in treatment of behavioural and psychological disturbances of dementia," European Neuropsychopharmacology, 15:S565, p. 5.017 (Abstract).
Petersen et al., "Mild cognitive impairment, clinical characterization and outcome," Arch. Neurology, 56:303-308 (1999).
Petersen et al., "Vitamin E and Donepezil for the Treatment of Mild Cognitive Impairment. Alzheimer's Disease Cooperative Study Group," N. Engl. J. Med., 52:2379-2388 (2005).
Petkov et al., "Effect of CDP-choline on learning and memory processes in rodents," Methods Find Exp. Clin. Pharamcol., 14(8):593-605 (1992).
Piazzini et al., "Levetiracetam: an improvement of attention and of oral fluency in patients with partial epilepsy," Epilepsy Research, 68(3):181-188 (2005).
Pitsikas et al., "Effect of oxiracetam on scopolamine-induced amnesia in the rat in a spatial learning task," Pharmacology Biochemistry and Behavior, 43(3):949-951 (1992).
Platel et al., "Habituation of exploratory activity in mice: effects of combinations of piracetam and choline on memory processes," Pharmacol. Biochem. Behav., 21(2):209-212 (1984).
Poschel et al., "Pharmacologic therapeutic window of pramiracetam demonstrated in behavior, EEG, and single neuron firing rates," Experientia., 41(9):1153-1156 (1985).

(56) References Cited

OTHER PUBLICATIONS

Poschel et al., "Pharmacology of the cognition activator pramiracetam (CI-879)," Drugs under Experimental and Clinical Research, 9(12):853-872 (1983).
Preda et al., "Effects of acute doses of oxiracetam in the scopolamine model of human amnesia," Psychopharmacology (Berl), 110(4):421-426 (1993).
Provinciali et al., "Recognition impairment correlated with short bisynchronoepileptic discharges," 32(5):684-689 (1991).
Pugsley et al., "Some neurochemical properties of pramiracetam (C1-879) a new cognition enhancing agent," Drug Development Research, 3(5):407-420 (1983).
Quiske et al., "Add-on treatement with LEV and its influence on cognition," Epilepsia, 46(S6):311, p. 986 (2005).
Rao et al., "Effects of intrahippocampal aniracetam treatment on Y-maze avoidance learning performance and behavioral long-term potentiation in dentate gyrin rat," Neuroscience Letters, 298(3):183-186 (2001).
Rao et al., "Recurrent seizures in patients with dementia: frequency, seizure types, and treatment outcome," Epilepsy Behav., 14(1):118-120 (2008).
Ravagnan et al., "ESES: 4 cases treated with levetiracetam," Bollettino—Lega Italiana contro l'Epilessia, 138:77-78 (2008) (English Abstract only).
Rogawski, "Diverse mechanisms of antiepileptic drugs in the development pipeline," Epilepsy Research, 69:273-294 (2006).
Rogers et al., "Long-term efficacy and safety of donepezil in the treatment of Alzheimer's disease: an interim analysis of the results of a multicentre open label extension study," Eur. Neuropsych. 8:67-75 (1998).
Rosche, et al. "Different cognitive effects of inducing levetiracetam or topiramate into an antiepileptic pharmacotherapy in patients with therapy refractory epilepsy," Neurology, Psychiatry and Brain Research, 11:109-114 (2004).
Rozzini et al., "Treatment of cognitive impairment secondary to degenerative dementia. Effectiveness of oxiracetam therapy," Acta. Neurol. (Napoli), 15(1):44-52 (1993).
Rudakova et al., "Levetiracetam (keppra) in the treatment of different epileptic syndromes in adults," Zhurnal nevrologii i psikhiatrii imeni S.S. Korsakova Ministerstvo zdravookhraneniia i meditsinskoi promyshlennosti Rossiiskoi Federatsii, Vserossiiskoe obshchestvo nevrologov [i] Vserossiiskoe obshchestvo psikhiatrov, 109(10):25-29 (2009) (English Abstract only).
Rugino et al., "Levetiracetam in autistic children: an open-label study," Journal of Development and Behavioral Pediatrics, 23(4)225-230 (2002).
Ryzhkov et al., "Levetiracetam treatment in rare epileptic syndromes of early childhood: a case series," Epilepsia, 47(S3):180,p. 701 (2006) (Abstract).
Ryzhkov, "Advantages of levetiracetam as monotherapy in treating epileptic syndromes of early childhood, characterized by psychological disorders," European Journal of Neurology, 14(S1):90, p. 1224 (2007) (Abstract).
Sajatovic et al., "Adjunct extended-release valproate semisodium in late life schizophrenia," International Journal of Geriatric Psychiatry, 23:142-147 (2008).
Salas-Puig et al., "Self-reported memory problems in everyday activities in patients with epilepsy treated with antiepileptic drugs," Epilepsy & Behavior, 14(4):622-627 (2009).
Saletu et al., "Pharmaco—EEG and Brain Mapping in Cognitive Enhancing Drugs," Clin. Neuropharamacol., 13(S 2):575-576 (1990).
Salimov et al., "Effect of chronic piracetam on age-related changes of cross-maze exploration in mice," Pharmacol. Biochem. Behav., 52(3):637-640 (1995).
Sankar et al., "Mechanisms of action for the commonly used antiepileptic drugs: relevance to antiepileptic drug-associated neurobehavioral adverse effects," Journal of Child Neurology, 19 (S1):S6-S14 (2004).

Sansone et al., "Effects of oxiracetam, physostigmine, and their combination on active and passive avoidance learning in mice," Pharmacol. Biochem. Behav., 44(2):451-455 (1993).
Sara et al., "Piracetam facilitates retrieval but does not impair extinction of bar-pressing in rats," Psychopharmacology (Berl.), 61(1):71-75 (1979).
Sara, "Memory retrieval deficits: alleviation by etiracetam, a nootropic drug," Psychopharmacology, 68(3):235-241 (1980).
Sargentini-Maier et al., "Brivaracetam Disposition in Renal Impairment," J. Clin. Pharmacol., published online Jan. 10, 2012.
Sargentini-Maier et al., "Pharmacokinetics and metabolism of $^{14}$C-brivaracetam, a novel SV2A ligand, in healthy subjects," Drug Metab Dispos, 36(1):36-45 (2008).
Sargentini-Maier et al., "The pharmacokinetics, CNS pharmacodynamics and adverse event profile of brivaracetam after single increasing oral doses in healthy males," British Journal of Clinical Pharmacology, 63(6):680-688 (2007).
Sarter et al., "Behavioral screening for cognition enhancers: From indiscriminate to valid testing: Part I," Psychopharmacology, 107:144-159 (1992).
Scarmeas et al., "Seizures in Alzheimer disease: who, when, and how common?" Arch. Neurol., 66(8):992-997 (2009).
Scheff et al., "Hippocampal synaptic loss in early Alzheimer's disease and mild cognitive impairment," Neurobiology of Aging, 27:1372-1384 (2006).
Schmidt et al., "Strategies and new aspects in the pharmacology of drugs for the treatment of senile dementia," Drug Development Research, 14(3-4):251-262 (1988).
Schmitz et al., "Assessing the unmet treatment need in partial-onset epilepsy: looking beyond seizure control," Epilepsia, 51(11):2231-2240 (2010).
Schneider et al., "Validity and reliability of the Alzheimer's Disease Cooperative Study—Clinical Global Impression of Change," The Alzheimer's Disease Cooperative Study, Alzheimer Dis. Assoc. Disord., 11 Suppl. 2:S22-S32 (1997).
Schobel et al., "Differential targeting of the CA1 subfield of the hippocampal formation by schizophrenia and related psychotic disorders," Arch. Gen. Psychiatry, 66:938-946 (2009).
Schoenberg et al., "Results of a randomized double-blind placebo controlled cross-over study of the cognitive and mood effects of levetiracetam in healthy older adults," Epilepsia, 48(S6):339, p. 3.246 (2007) (Abstract).
Shannon et al., "Effects of antiepileptic drugs on attention as assessed by a five-choice serial reaction time task in rats," Epilepsy Behavior, 7:620-628 (2005).
Shannon et al., "Effects of antiepileptic drugs on learning as assessed by a repeated acquisition of response sequences task in rats," Epilepsy Behavior, 10(1):16-25 (2007).
Shannon et al., "Effects of antiepileptic drugs on working memory as assessed by spatial alternation performance in rats," Epilepsy Behavior, 5(6):857-865 (2004).
Shorvon et al., "Multicenter double-blind, randomized, placebo-controlled trial of levetiracetam as add-on therapy in patients with refractory partial seizures. European Levetiracetam Study Group," Epilepsia, 41(9):1179-1186 (2000).
Shorvon, "Pyrrolidone derivatives," Lancet, 358(9296):1885-1892 (2001).
Smith et al., "Age-associated memory impairment diagnoses: problems of reliability and concerns for terminology," Psychology and Aging, 6(4):551-558 (1991).
Smith et al., "Circuit-specific alterations in hippocampal synaptophysin immunoreactivity predict spatial learning impairment in aged rats," J. Neuroscience, 20(17):6587-6593 (2000).
Sohn et al., "Effect of levetiracetam on rapid motor learning in humans," Annals of Neurology, 50:S31-S32 (2001).
Sohn et al., "Effect of levetiracetam on rapid motor learning in humans," Archives of Neurology, 59:1909-1912 (2002).
Soussain et al., "CNS complications of radiotherapy and chemotherapy," Lancet 374:1639-1651 (2009).
Specchio et al., "Event-related potentials (erps) in the evaluation of the effect of levetiracetam and carbamazepine on cognitive func-

(56) References Cited

OTHER PUBLICATIONS tions in adult newly diagnosed epileptic patients. preliminary results of a randomized open trial," Epilepsia, 50(S4):98, T189 (2009) (Abstract).
Stepien et al., "Profile of anticonvulsant activity and neuroprotective effects of novel and potential antiepileptic drugs—an update," Pharmacological Reports, 57(6):719-733 (2005).
Sugaya et al., "Levetiracetam suppresses development of spontaneoEEG seizures and aberrant neurogenesis following kainate-induced statepilepticus," Brain Research, 1352:187-199 (2010).
Takahashi et al., "Case report of sodium valproate treatment of aggression associated with Alzheimer's disease," Brain and Nerve (Tokyo), 48(8):757-760 (1996) (English Abstract only).
Taylor et al., "Levetiracetam is associated with improved cognitive outcome for patients with intracranial hemorrhage," Neurocritical Care, 15:80-84 (2011).
The Oct. 10, 2013 Office Action issued by the Chinese Patent Office in a corresponding Chinese Application No. 201180014664.8 (Chinese Language and the full-text English translation).
Tozzi et al., "[Levetiracetam in children and adolescents: Generalised vs partial seizures]," Bollettino—Lega Italiana contro l'Epilessia, 133-134:257-258 (2006) (English Abstract only).
Tregellas et al., "Intrinsic Hippocampal Activity as a Biomarker for Cognition and Symptoms in Schizophrenia," Am. J. Psychiatry, 1-8 (2014).
UCB Keppra® Injectable Formulation Label Approved on Sep. 12, 2007.
UCB Keppra® XR Label Approved on Apr. 23, 2009.
Veauthier et al., "Impact of levetiracetam add-on therapy on different EEG occipital frequencies in epileptic patients," Seizure: the journal of the British Epilepsy Association,18(6):392-395 (2009).
Vecht et al., "Seizures in low- and high-grade gliomas: current management and future outlook," Expert Review Anticancer Therapy, 10(5):663-669 (2010).
Verloes et al., "Effects of nootropic drugs in a scopolamine-induced amnesia model in mice," Psychopharmacology, 95(2):226-230 (1988).
Vicenzini et al., "[Clinical and neuropsycological effects of carbamazepine, oxcarbazepine and levetiracetam in healthy volunteers]"—Bollettino—Lega Italiana contro l'Epilessia, 118:173-175 (2002) (Italian—English abstract only).
Villardita et al., "Clinical studies with oxiracetam in patients with dementia of Alzheimer type and multi-infarct dementia of mild to moderate degree," Neuropsychobiology, 25(1):24-28 (1992).
Von Rosenstiel, "Brivaracetam (UCB 34714)," Neurotherapeutics: The Journal of the American Society for Experimental NeuroTherapeutics, 84-87 (2007).
Von Stülpnagel et al., "Levetiracetam as add-on therapy in different subgroups of "benign" idiopathic focal epilepsies in childhood," Epilepsy & Behavior, 17(2):193-198 (2010).
Waegemans et al., "Clinical efficacy of piracetam in cognitive impairment: a meta-analysis," Dement. Geriatr. Cogn. Disord., 13(4):217-224 (2002).
Walden et al., "Levetiracetam and ethosuximide in the treatment of acute mania in an open study with an on-off-on design," Bipolar Disorders, 4(Suppl 1):114 Abstract only (1 page) (2002).
Walker et al., "Early experience with UCB L059 in refractory epilepsy," European Congress Proceedings, 35(S7):76 (1994) (Abstract).
Wang et al., "Effect of commonly used new antiepileptic drugs on cognition," Zhongguo Xinyao Yu Linchuang Zazhi, China 27(9):705-709 (2008) (English Abstract only).
Wang et al., "Magnetic resonance imaging of hippocampal subfields in posttraumatic stress disorder," Arch. Gen. Psychiatry, 67:296-303 (2010).
Wheless et al., "Levetiracetam in refractory pediatric epilepsy," Journal of Child Neurology, 17(6):413-415 (2002).
Wheless, "Levetiracetam in the treatment of childhood epilepsy," Neuropsychiatric Disease and Treatment, 3(4):409-421 (2007).
Wilby et al., "Clinical effectiveness, tolerability and cost-effectiveness of newer drugs for epilepsy in adults: a systematic review and economic evaluation," Health Technology Assessment, Executive Summary—Newer drugs for epilepsy in adult, 9(15) (2005).
Winnicka et al., "Piracetam—An old drug with novel properties," Acta Pol.Pharm., Drug Research, 62(5):405-409 (2005).
Witt et al., "The impact of antiepileptic drug treatment on attention and executive functions," Epilepsia, 51(S4):20 (2010) (Abstract).
Witt, "The effects of levetiracetam on cognition—a noninterventional surveillance study," Epilepsia, 50(S4):227 (2009) (Abstract).
Wojda et al., "Isobolographic characterization of interactions of levetiracetam with the varioantiepileptic drugs in the mouse 6Hz psychomotor seizure model," Epilepsy Research, 86(2-3):163-174 (2009).
Wolthuis et al., "Behavioural effects of etiracetam in rats," Pharmacology Biochemistry & Behavior, 15:247-255 (1981).
Wolthuis, "Experiments with UCB 6215, a drug which enhances acquisition in rats: its effects compared with those of metamphetamine," Eur. J. Pharmacol., 16(3):283-297 (1971).
Woon et al., "Hippocampal volume deficits associated with exposure to psychological trauma and posttraumatic stress disorder in adults: a meta-analysis," Prog Neuropsychopharmacol Biol Psychiatry, 34:1181-1188 (2010).
Wu et al., "Clinical efficacy and cognitive and neuropsycholoical effects of levetiracetam in epilepsy: an open-label multicenter study," Epilepsy & Behavior, 16(3):468-474 (2009) (Abstract).
Wu, "The effects of antiepileptic drugs on cognitive function," Erke Yaoxue Zazhi, China, 13(6):7-9 (2007) (English Abstract only).
Xie et al., "Observation for the effects of nicergoline for treating aging low-grade cognitive disorders," Chinese Community Physician, 11(3):20-21 (2009) (Chinese Language and English Abstract only).
Yaffe et al., "Post-Traumatic Stress Disorder and Risk of Dementia among U.S. Veterans," Arch. Gen. Psych., 678:608-613 (2010).
Yamada et al., "Prolongation of latencies for passive avoidance responses in rats treated with aniracetam or piracetam," Pharmacol. Biochem. Behav., 22(4):645-648 (1985).
Yang et al., "Adjunctive levetiracetam in children and adolescents aged 4-16 years with partial-onset seizures: A long-term, multicenter, noncomparative, open-label, follow-up study," Epilepsia, 50(S10):102, p. 471 (2009) (Abstract).
Yang et al., "Cyclophosphamide impairs hippocampus-dependent learning and memory in adult mice: Possible involvement of hippocampal neurogenesis in chemotherapy-induced memory deficits," Neurobiology of Learning and Memory, Epilepsia, 93:487-494 (2010).
Yang et al., "Therapeutic effect of levetiracetam for epilepsy combined with electrical statepilepticduring sleep in children," Shiyong Erke Linchuang Zazhi, 25(12):937-939 (2010) (English Abstract only).
Yassa et al., "Ultrahigh-resolution microstructural diffusion tensor imaging reveals perforant path degradation in aged humans in vivo," PNAS, 107:12687-12691 (2010).
Yehuda et al., "Longitudinal assessment of cognitive performance in Holocaust survivors with and without PTSD," Bio. Psych., 60:714-721 (2006).
Youngjohn et al., "Stability of everyday memory in age-associated impairment: A longitudinal study," Neuropsychology, 7(3);406-416 (1993).
Yuede et al., Anti-dementia drugs and hippocampal-dependent memory in rodents, Behav. Pharmacol., 18:347-363 (2007).
Zaccara et al., "Central nervosystem adverse effects of new antiepileptic drugs. A meta-analysis of placebo-controlled studies," Seizure, 17(5):405-421 (2008).
Zhao et al., "Effect of levetiracetam on visual-spatial memory impairment following statepilepticus," Epilepsia, 47(S4):201 (2006) (Abstract).
Zhou et al., "Cognitive and quality of life effects of levetiracetam as an add-on therapy for partial seizures," Epilepsia, 48(S7):70, p. 116 (2007) (Abstract).
Zhou et al., "Effect of levetiracetam on visual-spatial memory following statepilepticus," Epilepsy Research, 73(1):65-74 (2006).

(56) References Cited

OTHER PUBLICATIONS

Zhou et al., "Levetiracetam: an improvement of attention and of oral fluency in patients with partial epilepsy," Epilepsy & Behavior, 12:305-310 (2008).

Zhu et al., "Progress in the research of Alzheimer's disease and its drug therapies," Guangzhou Chemistry, 29(2):35-44 (2004) (Chinese Language and English Abstract only; machine English translation of full text; and English translation of paragraphs 1.2, 1.2.3 and 2.1.

Zou et al., "Effects of chronic treatment of levetiracetam on cognitive and motor recovery after experimental traumatic brain injury," Journal of Neurotrauma, 26:A67, p. 262 (2009) (Abstract).

Karakaya, et al., "Pharmacological Treatment of Mild Cognitive Impairment as a Prodromal Syndrome of Alzheimer's Disease," Current Neuropharmacology, 11(1):102-108 (2013).

Luciano et al., "Results of treatment changes in patients with apparently drug-resistant chronic epilepsy," Annals of Neurology, 62(4):375-381 (2007).

Philips, et al., "An observational assessment method for aging laboratory rats," The Journal of the American Association for Laboratory Animal Science, 49(6):792-799 (2010).

Chaisewikul et al., "Levetiracetam add-on for drug-resistant localization related (partial) epilepsy," Cochrane Collaboration, Issue 1, p. 1-25 (2010).

Ciesielski et al., "Neuropsychological and psychiatric impact of add-on titration of pregabalin versus levetiracetam: a comparative short-term study," Epilepsy & Behavior, 9(3):424-431 (2006).

Minervini et al., "Mild cognitive impairment, focal epilepsy and levetiracetam," Epilepsia, 48:(S7):110, p. 256 (2007) (Abstract).

Leppik, et al., "Extended-release antiepileptic drugs: a comparison of pharmacokinetic parameters relative to original immediate-release formulations," Epilepsia, 54(1):28-35 (2013).

Rouits, et al., "Pharmacokinetics of levetiracetam XR 500mg tablets," Epilepsy Research, 84(2-3):224-231 (2009).

Ulloa, et al., "Review of levetiracetam, with a focus on the extended release formulation, as adjuvant therapy in controlling partial-onset seizures," Neuropsychiatric Disease and Treatment, 5:467-476 (2009).

* cited by examiner

EXTENDED RELEASE PHARMACEUTICAL COMPOSITIONS OF LEVETIRACETAM

This application is a national stage application under 35 U.S.C. § 371 of International Application PCT/US2016/033567, filed on May 20, 2016, which is a continuation of U.S. patent application Ser. No. 15/160,424, filed May 20, 2016, and claims priority from and benefit of U.S. Provisional Patent Application 62/165,812, filed May 22, 2015, the contents and disclosures of which are incorporated herein by reference in their entirety.

FIELD OF THE INVENTION

This invention relates to novel extended release pharmaceutical compositions of levetiracetam and preparations and characterizations thereof. This invention further relates to using these extended release pharmaceutical compositions of levetiracetam for the treatment of cognitive impairment associated with central nervous system (CNS) disorders in a subject in need or at risk thereof.

BACKGROUND OF THE INVENTION

Cognitive ability may decline as a normal consequence of aging or as a consequence of a CNS disorder.

For example, a significant population of elderly adults experiences a decline in cognitive ability that exceeds what is typical in normal aging. Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and MCI is estimated to affect 5.5-7 million in the U.S. over the age of 65 (Plassman et al., 2008).

Cognitive impairment is also associated with other central nervous system (CNS) disorders, such as dementia, Alzheimer's Disease (AD), prodromal AD, post traumatic stress disorder (PTSD), schizophrenia, bipolar disorder (e.g., mania), amyotrophic lateral sclerosis (ALS), cancer-therapy-related cognitive impairment, mental retardation, Parkinson's disease (PD), autism, compulsive behavior, and substance addiction.

There is, therefore, a need for effective treatment of cognitive impairment associated with central nervous system (CNS) disorders and to improve cognitive function in patients diagnosed with, for example, age-related cognitive impairment, MCI, amnestic MCI, AAMI, ARCD, dementia, Alzheimer's Disease (AD), prodromal AD, post traumatic stress disorder (PTSD), schizophrenia, bipolar disorder (e.g., mania), amyotrophic lateral sclerosis, cancer-therapy-related cognitive impairment, mental retardation, Parkinson's disease (PD), autism, compulsive behavior, and substance addiction, and similar central nervous system (CNS) disorders associated with cognitive impairment or at risk of developing them.

Levetiracetam is a widely used antiepileptic drug. Its International Union of Pure and Applied Chemistry (IUPAC) name is (2S)-2-(2-oxopyrrolidin-1-yl) butanamide) and its chemical structure is shown in Formula I.

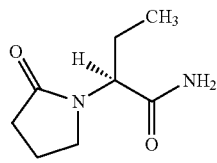

Formula I

Levetiracetam is indicated as adjunctive therapy in the treatment of partial onset seizures, or myoclonic seizures, or primary generalized tonic-clonic seizures. It is recommended that such treatments should be initiated with a daily dose of 1000 mg/day. Additional dosing increments may be given to a maximum recommended daily dose of 3000 mg. Levetiracetam is currently available as immediate and extended release formulations for oral administration. Extended release dosage form of levetiracetam is available in strengths of 500 mg, 750 mg, and 1000 mg for once daily usage. Immediate release dosage form of levetiracetam is available in strengths of 250 mg, 500 mg, 750 mg, and 1000 mg for twice daily usage.

International Application Nos. PCT/US09/05647, PCT/US12/24556, and PCT/US14/29170 disclose that levetiracetam, when administered at a dose lower than the therapeutic doses for treating epilepsy, can treat cognitive impairment associated with central nervous system (CNS) disorders in a subject in need or at risk thereof.

The currently commercially available extended release dosage forms of levetiracetam comprise 500 mg, 750 mg, and 1000 mg of levetiracetam. Such extended release dosage forms are not suitable for treating cognitive impairment. There is, therefore, a need for novel extended release compositions of levetiracetam for treating cognitive impairment.

SUMMARY OF THE INVENTION

In one aspect, the present invention provides an extended release pharmaceutical composition comprising: a) 220 mg of levetiracetam; b) 280 mg-350 mg of hydroxypropyl methylcellulose; c) 1.2 mg-1.4 mg of colloidal silicon dioxide; d) 92.8 mg-119.2 mg of silicified microcrystalline cellulose; and e) 6.0 mg-6.7 mg of magnesium stearate. In another aspect, the present invention provides an extended release pharmaceutical composition comprising: a) 220 mg of levetiracetam; b) 280 mg of hydroxypropyl methylcellulose; c) 1.2 mg of colloidal silicon dioxide; d) 92.8 mg of silicified microcrystalline cellulose; and e) 6.0 mg of magnesium stearate. In another aspect, the present invention provides an extended release pharmaceutical composition comprising: a) 220 mg of levetiracetam; b) 347.5 mg of hydroxypropyl methylcellulose; c) 1.4 mg of colloidal silicon dioxide; d) 119.2 mg of silicified microcrystalline cellulose; and e) 6.7 mg of magnesium stearate. In certain embodiments of these aspects of the invention, the hydroxypropyl methylcellulose is Methocel™ K15M CR or Methocel™ K100M Premium CR. In certain embodiments of these aspects of the invention, the hydroxypropyl methylcellulose is Methocel™ K15M CR. In certain embodiments of these aspects of the invention, the silicified microcrystalline cellulose is ProSolv™ HD90.

In another aspect, the present invention provides an extended release pharmaceutical composition comprising: a) 190 mg of levetiracetam; b) 300 mg of hydroxypropyl methylcellulose; c) 1.2 mg of colloidal silicon dioxide; d) 102.8 mg of silicified microcrystalline cellulose; and e) 6 mg of magnesium stearate. In another aspect, the present invention provides an extended release pharmaceutical composition comprising: a) 190 mg of levetiracetam; b) 300 mg of hydroxypropyl methylcellulose; c) 1.2 mg of colloidal silicon dioxide; d) 102.8 mg of anhydrous dicalcium phosphate; and e) 6 mg of magnesium stearate. In certain embodiments of these aspects of the invention, the hydroxypropyl methylcellulose is Methocel™ K15M CR or Methocel™ K100M Premium CR. In certain embodiments of these aspects of the invention, the hydroxypropyl methylcellulose is Methocel™ K15M CR. In certain embodiments of these aspects of the invention, the silicified microcrystalline cellulose is ProSolv™ HD90.

In certain embodiments of the invention, the extended release pharmaceutical composition of the invention is formulated for once daily administration.

In certain embodiments of the invention, the extended release pharmaceutical composition of the invention is formulated for one-unit-dosage-form-once-daily administration.

In certain embodiments of the invention, the extended release pharmaceutical composition of the invention is in the form of a tablet. In some embodiments, the extended release pharmaceutical composition of the invention is in a tablet form and is formulated for one-tablet-once-daily administration.

In certain embodiments of the invention, the extended release pharmaceutical composition of the invention is formulated for oral administration.

In certain embodiments of the invention, the extended release pharmaceutical composition of the invention does not comprise a hydrophobic rate controlling polymer.

In certain embodiments of the invention, the extended release pharmaceutical composition of the invention does not comprise a functional coating.

In another aspect, this invention provides methods of improving cognition in a subject suffering from cognitive impairment or at risk thereof by administering the extended release pharmaceutical compositions of the invention. In certain embodiments, the subject suffers from cognitive impairment associated with a central nervous system (CNS) disorder, or at risk thereof. In certain embodiments, the cognitive impairment is associated with age-related cognitive impairment. In certain embodiments, the age-related cognitive impairment is Mild Cognitive Impairment. In certain embodiments, the Mild Cognitive Impairment is amnestic Mild Cognitive Impairment. In certain embodiments, the cognitive impairment is associated with dementia, Alzheimer's disease, schizophrenia, amyotrophic lateral sclerosis, post traumatic stress disorder, cancer therapy, bipolar disorder mental retardation, Parkinson's disease, autism, compulsive behavior, or substance addiction.

In another aspect, this invention provides methods of treating mild cognitive impairment due to Alzheimer's disease in a human subject in need thereof by administering the extended release pharmaceutical compositions of the invention.

In another aspect, this invention provides methods of treating amnestic mild cognitive impairment due to Alzheimer's disease in a human subject in need thereof by administering the extended release pharmaceutical compositions of the invention.

In another aspect, this invention provides methods of slowing the progression of mild cognitive impairment due to Alzheimer's disease in a human subject in need thereof by administering the extended release pharmaceutical compositions of the invention.

In another aspect, this invention provides methods of slowing the progression of amnestic mild cognitive impairment due to Alzheimer's disease in a human subject in need thereof by administering the extended release pharmaceutical compositions of the invention.

DETAILED DESCRIPTION OF THE INVENTION

Figure 1:
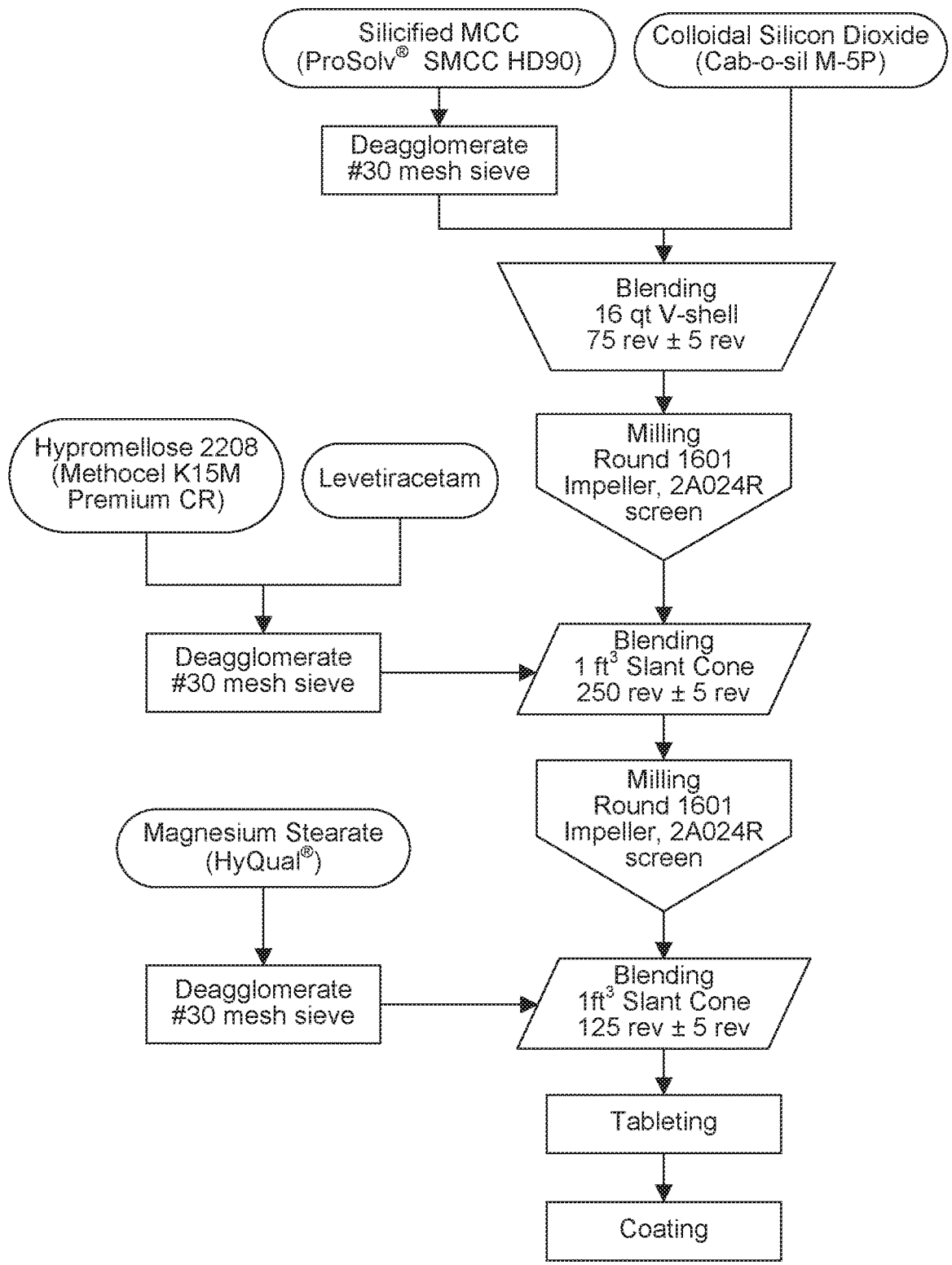
FIG. 1 is a flow diagram of one embodiment of a process for manufacturing extended release compositions of levetiracetam (e.g., 190 mg and 220 mg tablets listed in Tables 1 and 3).

This invention provides novel extended release pharmaceutical compositions of levetiracetam. This invention also provides methods of using these extended release pharmaceutical compositions of levetiracetam for treating cognitive impairment or improving cognitive function associated with central nervous system (CNS) disorders in a subject in need or at risk thereof. This invention also provides using these extended release pharmaceutical compositions of levetiracetam in the manufacture of medicaments for treating cognitive impairment or improving cognitive function associated with central nervous system (CNS) disorders in a subject in need or at risk thereof.

In order that the invention herein described may be fully understood, the following details description is set forth.

Unless otherwise defined herein, scientific and technical terms used in this application shall have the meanings that are commonly understood by those of ordinary skill in the art to which this invention belongs. Generally, nomenclature used in connection with, and techniques of, cell and tissue culture, molecular biology, cell biology, cancer biology, neurobiology, neurochemistry, virology, immunology, microbiology, genetics, protein and nucleic acid chemistry, chemistry, and pharmacology described herein, are those well known and commonly used in the art. Each embodiment of the inventions described herein may be taken alone or in combination with one or more other embodiments of the inventions.

The methods and techniques of the present invention are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

In order to further define the invention, the following terms and definitions are provided herein.

Definitions

The term "extended release", ""extended release form", or "extended release dosage form" is widely recognized in the art of pharmaceutical sciences as systems that maintains therapeutic blood or plasma or tissue levels of a drug for an extended period. An extended release dosage form potentially provides greater effectiveness in the treatment of chronic diseases or conditions; greater convenience; reduces side effects and provides higher levels of patient compliance or therapeutic performance due to a simplified dosage schedule, compared with those of immediate-release drugs. Extended release pharmaceutical products are formulated to release the active ingredient gradually and predictably over an extended time period, such as a 24-hour period.

The term "extended release", "extended release form", or "extended release dosage form" is used herein to refer to a controlled release of levetiracetam from a dosage form to an environment over (throughout or during) an extended period of time, e.g., twenty-four hours. An extended release dosage form will release drug at substantially constant rate over an extended period of time or a substantially constant amount of drug will be released incrementally over an extended period of time. The term "extended release" used herein includes the terms "controlled release", "prolonged release", "sustained release", "slow release", or "modified release" as these terms are used in the pharmaceutical sciences.

The term "active ingredient" "active pharmaceutical ingredient" or "API" as used herein is defined as a substance which has a therapeutic effect, such as levetiracetam.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care, speed of processing, reasoning and problem solving and social cognition.

In humans, cognitive function may be measured, for example and without limitation, by measuring neuronal injury, measuring change in Entorhinal Cortex thickness using structural MIll (e.g., for measuring neuronal injury); the clinical global impression of change scale (CIBIC-plus scale); the Mini Mental State Exam (MMSE); the Neuropsychiatric Inventory (NPI); the Clinical Dementia Rating Scale (CDR) (global, memory box); the Cambridge Neuropsychological Test Automated Battery (CANTAB); the Sandoz Clinical Assessment-Geriatric (SCAG); the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test; or the explicit 3-alternative forced choice task; or MATRICS consensus neuropsychological test battery; or ADAS-Cog 13 item-scale; Wechsler Logical Memory I and II; BSP—O; Neuropsychological tests (Trails A and B, BNT, SR, CFT, R—O, Paired-associates), other MRI measures, DTI, resting fMRI, and the GDS. See Folstein et al., *J Psychiatric Res* 12: 189-98, (1975);

Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later? Schizophr. Bull. 37, 1209-1217.

In animal model systems, cognitive function may be measured in various conventional ways known in the art, including using a Morris Water Maze (MWM), Barnes circular maze, elevated radial arm maze, T maze or any other mazes in which the animals use spatial information. Cognitive function can be assessed by reversal learning, extradimensional set shifting, conditional discrimination learning and assessments of reward expectancy. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Promoting" cognitive function refers to affecting impaired cognitive function so that it more closely resembles the function of a normal, unimpaired subject. Cognitive function may be promoted to any detectable degree, but in humans preferably is promoted sufficiently to allow an impaired subject to carry out daily activities of normal life a level of proficiency as close as possible to a normal, unimpaired subject or an age-matched normal, unimpaired subject.

In some cases, "promoting" cognitive function in a subject affected by age-related cognitive refers to affecting impaired cognitive function so that it more closely resembles the function of an aged-matched normal, unimpaired subject, or the function of a young adult subject. Cognitive function of that subject may be promoted to any detectable degree, but in humans preferably is promoted sufficiently to allow an impaired subject to carry out daily activities of normal life at a level of proficiency as close as possible to a normal, unimpaired subject or a young adult subject or an age-matched normal, unimpaired subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Cognitive impairment" refers to cognitive function in subjects that is not as robust as that expected in a normal, unimpaired subject. In some cases, cognitive function is reduced by about 5%, about 10%, about 30%, or more, compared to cognitive function expected in a normal, unimpaired subject. In some cases, "cognitive impairment" in subjects affected by aged-related cognitive impairment refers to cognitive function in subjects that is not as robust as that expected in an aged-matched normal, unimpaired subject, or the function of a young adult subject (i.e. subjects with mean scores for a given age in a cognitive test).

"Treating" a condition or patient refers to taking steps to obtain beneficial or desired results, including clinical results. Beneficial or desired clinical results include, but are not limited to, improving cognitive function, delaying or slowing the progression of cognitive impairment, reducing the rate of decline of cognitive function, preventing or slowing the progression of the disease or disorder, or alleviation, amelioration, or slowing the progression, of one or more symptoms associated of cognitive impairment associated with CNS disorders, such as age-related cognitive impairment, Mild Cognitive Impairment (MCI), amnestic MCI, dementia, Alzheimer's Disease (AD), prodromal AD, PTSD, schizophrenia or bipolar disorder (in particular, mania), amyotrophic lateral sclerosis (ALS) or cancer therapy-related cognitive impairment. Treating age-related cognitive impairment further comprises slowing the conversion of age-related cognitive impairment (including, but not limited to MCI, ARCD and AAMI) into dementia (e.g., AD).

"Treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. Treatment of cognitive impairment in humans may improve cognitive function to any detectable degree, but is preferably improved sufficiently to allow the impaired subject to carry out daily activities of normal life at the same level of proficiency as a normal, unimpaired subject. In some cases, "treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. In some cases, "treating cognitive impairment" in a subject affecting by age-related cognitive impairment refers to takings steps to improve cognitive function in the subject so that the subject's cognitive function, after treatment of cognitive impairment, more closely resembles the function of an age-matched normal, unimpaired subject, or the function of a young adult subject. In some cases, "treating cognitive impairment" in a subject refers to taking steps to delay or slow the progression of cognitive impairment in a subject with cognitive impairment. In some cases, "treating cognitive impairment" in a subject refers to taking steps to reduce the rate of decline of cognitive function in a subject with cognitive impairment.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents which are known with respect to structure, and those which are not known with respect to structure.

Description of Compositions of the Invention

This invention provides extended release compositions of levetiracetam. The compositions of this invention can be used for improving cognition in patients who suffer from cognitive impairment associated with central nervous system (CNS) disorders in a subject in need or at risk thereof. The compositions of this invention is administered once a day (i.e., once every 24 hours) for improving cognition.

In one aspect, the invention provides extended release pharmaceutical compositions comprising: a) 220 mg of levetiracetam; b) 280 mg to 350 mg of hydroxypropyl methylcellulose (or hypromellose); c) 1.2 mg to 1.4 mg of colloidal silicon dioxide; d) 92.8 mg-119.2 mg of silicified microcrystalline cellulose; and e) 6.0 mg to 6.7 mg of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 220 mg of levetiracetam; b) 280 mg of hydroxypropyl methylcellulose (or hypromellose); c) 1.2 mg of colloidal silicon dioxide; d) 92.8 mg of silicified microcrystalline cellulose; and e) 6.0 mg of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 220 mg of levetiracetam; b) 347.5 mg of hydroxypropyl methylcellulose (or hypromellose); c) 1.4 mg of colloidal silicon dioxide; d) 119.2 mg of silicified microcrystalline cellulose; and e) 6.7 mg of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 220 mg of levetiracetam; b) 280 mg of hydroxypropyl methylcellulose (or hypromellose) Methocel™ K15M CR; c) 1.2 mg of colloidal silicon dioxide; d) 92.8 mg of silicified microcrystalline cellulose ProSolv™ HD90; and e) 6.0 mg of magnesium stearate (e.g., HyQual®). In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 220 mg of levetiracetam; b) 347.5 mg of hydroxypropyl methylcellulose (or hypromellose) Methocel™ K15M CR; c) 1.4 mg of colloidal silicon dioxide; d) 119.2 mg of silicified microcrystalline cellulose ProSolv™ HD90; and e) 6.7 mg of magnesium stearate (e.g., HyQual®). In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 190 mg of levetiracetam; b) 300 mg of hydroxypropyl methylcellulose (or hypromellose); c) 1.2 mg of colloidal silicon dioxide; d) 102.8 mg of silicified microcrystalline cellulose; and e) 6 mg of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 190 mg of levetiracetam; b) 300 mg of hydroxypropyl methylcellulose (or hypromellose); c) 1.2 mg of colloidal silicon dioxide; d) 102.8 mg of anhydrous dicalcium phosphate; and e) 6 mg of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the magnesium stearate is HyQual®. In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 190 mg of levetiracetam; b) 300 mg of hydroxypropyl methylcellulose (or hypromellose) Methocel™ K15M CR; c) 1.2 mg of colloidal silicon dioxide; d) 102.8 mg of silicified microcrystalline cellulose ProSolv™ HD90; and e) 6 mg of magnesium stearate (e.g., HyQual®). In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 190 mg of levetiracetam; b) 300 mg of hydroxypropyl methylcellulose (or hypromellose) Methocel™ K100M Premium CR; c) 1.2 mg of colloidal silicon dioxide; d) 102.8 mg of silicified microcrystalline cellulose ProSolv™ HD90; and e) 6 mg of magnesium stearate (e.g., HyQual®). In some embodiments, the extended release pharmaceutical composition is in a solid form. In some embodiments, the extended release pharmaceutical composition is in the form of a tablet or capsule.

In another aspect, the invention provides extended release pharmaceutical compositions comprising: a) 190 mg of levetiracetam; b) 300 mg of hydroxypropyl methylcellulose (or hypromellose) Methocel™ K100M Premium CR; c) 1.2 mg of colloidal silicon dioxide; d) 102.8 mg of anhydrous dicalcium phosphate; and e) 6 mg of magnesium stearate (e.g., HyQual®). In some embodiments, the extended release pharmaceutical composition is in a solid form. In some embodiments, the extended release pharmaceutical composition is in the form of a tablet or capsule.

In another aspect, the invention provides extended release pharmaceutical compositions comprising 100-350 mg of levetiracetam, a matrix-forming polymer, a glidant, a diluent, and a lubricant. In some embodiments, the matrix-forming polymer is water soluble. In some embodiments, the diluent is water soluble. In some embodiments, the amount of levetiracetam in the extended release pharmaceutical compositions is 125-250 mg of levetiracetam. In some embodiments, the percentage of the matrix-forming polymer in the extended release pharmaceutical compositions is any range between 45% w/w-70% w/w, such as 45%, 46%, 47%, 48%, 49%, 50%, 55%, 60%, 65%, or 70% w/w.

In another aspect, the invention provides extended release pharmaceutical compositions comprising: a) 30-40% w/w (e.g., 31.7-36.7% w/w) of levetiracetam; b) 45-55% w/w (e.g., 46.7-50% w/w) of hydroxypropyl methylcellulose (or hypromellose); c) 0.01-5% w/w of colloidal silicon dioxide (e.g., 0.2% w/w); d) 15-20% w/w (15.5-17.1% w/w) of silicified microcrystalline cellulose; and e) 0.01-5% w/w of magnesium stearate (e.g., 0.96-1% w/w). In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 36.7% w/w of levetiracetam; b) 46.7% w/w of hydroxypropyl methylcellulose (or hypromellose); c) 0.2% w/w of colloidal silicon dioxide; d) 15.5% w/w of silicified microcrystalline cellulose; and e) 1% w/w of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose); c) 0.2% w/w mg of colloidal silicon dioxide; d) 17.1% w/w of silicified microcrystalline cellulose; and e) 0.96% w/w of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 695 mg. In some embodiments, the extended release composition comprises 125-250 mg of levetiracetam.

In another aspect, the invention provides extended release pharmaceutical compositions comprising: a) 36.7% w/w of levetiracetam; b) 46.7% w/w of hydroxypropyl methylcellulose (or hypromellose) Methocel™ K15M CR; c) 0.2% w/w of colloidal silicon dioxide; d) 15.5% w/w of silicified microcrystalline cellulose ProSolv™ HD90; and e) 1% w/w of magnesium stearate (e.g., HyQual®). In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of dhydroxypropyl methylcellulose (or hypromellose) Methocel™ K15M CR; c) 0.2% w/w of colloidal silicon dioxide; d) 17.1% w/w of silicified microcrystalline cellulose ProSolv™ HD90; and e) 0.96% w/w of magnesium stearate (e.g., HyQual®). In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 695 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose); c) 0.2% w/w of colloidal silicon dioxide; d) 17.1% w/w of silicified microcrystalline cellulose; and e) 1% w/w of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the silicified microcrystalline cellulose is ProSolv™ HD90. In some embodiments, the magnesium stearate is HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose); c) 0.2% w/w of colloidal silicon dioxide; d) 17.1% w/w of anhydrous dicalcium phosphate; and e) 1% w/w of magnesium stearate. In some embodiments, the hydroxypropyl methylcellulose (or hypromellose) is Methocel™ K15M CR. In some embodiments, the hydroxypropyl methylcellulose (or hypromellose) is Methocel™ K100M Premium CR. In some embodiments, the magnesium stearate is HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose) Methocel™ K15M CR; c) 0.2% w/w of colloidal silicon dioxide; d) 17.1% w/w of silicified microcrystalline cellulose ProSolv™ HD90; and e) 1% w/w of magnesium stearate (e.g., HyQual®). In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose) Methocel™ K100M Premium CR; c) 0.2% w/w of colloidal silicon dioxide; d) 17.1% w/w of silicified microcrystalline cellulose ProSolv™ HD90; and e) 1% w/w of magnesium stearate (e.g., HyQual®). In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In another aspect, the invention provides extended release pharmaceutical compositions comprising: a) 31.7% w/w of levetiracetam; b) 50% w/w of hydroxypropyl methylcellulose (or hypromellose) Methocel™ K100M Premium CR; c) 0.2% w/w of colloidal silicon dioxide; d) 17.1% w/w of anhydrous dicalcium phosphate; and e) 1% w/w of magnesium stearate HyQual®. In some embodiments, the extended release pharmaceutical composition is in a solid form. In some embodiments, the extended release pharmaceutical composition is in the form of a tablet or capsule. In some embodiments, the total weight of the extended release pharmaceutical composition is 250 mg-1000 mg. In a particular embodiment, the total weight of the extended release pharmaceutical composition is 600 mg. In some embodiments, the extended release composition comprises 125-250 mg of levetiracetam.

In some embodiments, the invention uses hydroxypropyl methylcellulose (or hypromellose) as a rate controlling polymer or a matrix forming polymer in the extended release compositions. In some embodiments, hydroxypropyl methylcellulose (or hypromellose) can be used together with other rate controlling polymers or matrix forming polymers in the compositions of this invention. In some embodiments, hydroxypropyl methylcellulose can be replaced by other rate controlling polymers or matrix forming polymers in the compositions of this invention. In some embodiments, the rate controlling polymers or matrix forming polymers that can replace hydroxypropyl methylcellulose or be used together with hydroxypropyl methylcellulose have similar properties or characteristics as hydroxypropyl methylcellulose. Examples of these rate controlling polymers or matrix forming polymers include, without being limited to, cellulose, non-cellulose polysaccharide, polyvinyl polymer, hydrogel, monolithic polymer, or mixtures thereof. In some embodiments, hydroxypropyl methylcellulose, hydroxyethyl cellulose, hydroxypropyl cellulose, methylcellulose, sodium carboxymethyl cellulose, sodium alginate, carbomer, xanthan gum, guar gum, locust bean gum, carob gum, arabic gum, sterculia gum, polyvinyl pyrrolidone, polyvinyl acetate, polyvinyl alcohol, polyethylene oxide, or a mixture thereof can be used as a rate controlling polymer or matrix forming polymer in the compositions of the invention. In some embodiments, the hydroxypropyl methylcellulose (or hypromellose) in the compositions of the present invention may be selected from the group consisting of Methocel™ K4M, K15M, K100M, E4M, E10M, K4M CR, K15M CR, K100M CR, E4M CR, E10M CR, K4M Premium, K15M Premium, K100M Premium, E4M Premium, E10M Premium, K4M Premium CR, K15M Premium CR, K100M Premium CR, E4M Premium CR, E10M Premium CR, and K100 Premium LV.

In some embodiments, the invention uses colloidal silicon dioxide as a glidant in the extended release compositions. In some embodiments, colloidal silicon dioxide can be used together with other glidants in the compositions of this invention. In some embodiments, colloidal silicon dioxide can be replaced by other glidants in the compositions of this invention. In some embodiments, the glidant that can replace colloidal silicon dioxide or that can be used together with colloidal silicon dioxide have similar properties or characteristics as colloidal silicon dioxide. Examples of these glidants include, without being limited to, cornstarch, talc, calcium silicate, magnesium silicate, aluminum silicate, silicon hydrogel or a mixture thereof.

In some embodiments, the invention uses silicified microcrystalline cellulose as a diluent in the extended release compositions. In some embodiments, silicified microcrystalline cellulose can be used together with other diluents in the compositions of this invention. In some embodiments, silicified microcrystalline cellulose can be replaced by other diluents in the compositions of this invention. In some embodiments, the diluent that can replace silicified microcrystalline cellulose or that can be used together with silicified microcrystalline cellulose have similar properties or characteristics as silicified microcrystalline cellulose, such as water solubility. Examples of these diluents (or water soluble diluents) include, without being limited to, microcrystalline cellulose, lactose, mannitol, xylitol, dextrose, sucrose, sorbitol, compressible sugar, powdered cellulose, cornstarch, pregelatinized starch, dextrate, dextran, dextrin, dextrose, maltodextrin, calcium carbonate, polyethylene oxide, and a mixture thereof.

In some embodiments, the invention uses magnesium stearate as a lubricant in the extended release compositions. In some embodiments, magnesium stearate can be used together with other lubricants in the compositions of this invention. In some embodiments, magnesium stearate can be replaced by other lubricants in the compositions of this invention. In some embodiments, the lubricant that can replace magnesium stearate or that can be used together with magnesium stearate have similar properties or characteristics as magnesium stearate. Examples of these lubricants include, without being limited to, calcium stearate, sodium stearyl fumerate, glyceryl palmitostearate, glyceryl stearate, mineral oil, stearic acid, zinc stearate and a mixture thereof.

The compositions described herein can further contain pharmaceutically acceptable excipient(s) and may contain other agents that serve to enhance and/or complement the effectiveness of the levetiracetam, or to enhance or improve the extended release profile or pharmacokinetic profile of the levetiracetam.

In some embodiments, the pharmaceutical composition of the present invention is the formulations in Table 1. In one embodiment, the pharmaceutical composition of the present invention is the 190 mg Tablet A formulation.

In some embodiments, the pharmaceutical composition of the present invention is the formulations in Table 3. In one embodiment, the pharmaceutical composition of the present invention is the 220 mg Tablet D formulation.

In some embodiments, the extended release levetiracetam compositions are formulated for once daily administration. For example, the extended release compositions comprise 190 mg of levetiracetam and provide a daily dosage of 190 mg when administered once a day (i.e., every twenty-four hours). The extended release compositions comprise 220 mg of levetiracetam and provide a daily dosage of 220 mg when administered once a day (i.e., every twenty-four hours). In some embodiments, the extended release levetiracetam compositions are formulated for one-unit-dosage-form-once-daily administration. In some embodiments, the extended release levetiracetam compositions are formulated for one-tablet-once-daily administration. For example, subjects who suffer from cognitive impairment will take the extended release composition of the invention (e.g., Tablets A, B, and C in Table 1 or Tablets D and E in Table 3) one-tablet-once-a-day. Each tablet is an extended release dosage form comprising 190 mg or 220 mg of levetiracetam.

In some embodiments, the extended release levetiracetam compositions are administered in the morning.

In some embodiments, the extended release levetiracetam compositions are in a solid form, for example, tablets, capsules, mini-tablets, mini tablets in a capsule, dragrees, pills, lozenges, granules, films or dissolvable films. In some embodiments, the compositions of the present invention are in the form of a tablet. In some embodiments, the tablet is a homogeneous mixture.

In some embodiments, the extended release levetiracetam compositions are formulated for oral administration. In some embodiments, the extended release pharmaceutical compositions are formulated in a solid form for oral administration. In some embodiments, the extended release levetiracetam compositions are oral tablets. In some embodiments, the extended release levetiracetam compositions are oral capsules. In some embodiments, the extended release levetiracetam compositions are formulated for injection or sublingual administration. In some embodiments, the extended release levetiracetam compositions are formulated for administration in the form of a patch or a pump.

In some embodiments, the pharmaceutical compositions of the invention do not comprise a hydrophobic rate controlling polymer.

In some embodiments, the pharmaceutical compositions of the invention do not comprise a functional coating.

Description of Methods of the Invention

The methods of this invention comprise administration of the extended release compositions of levetiracetam for treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism, compulsive behavior, and substance addiction.

In some embodiments, treatment comprises improving cognitive function in patients suffering from or at risk for cognitive impairment associated with a CNS disorder, such as age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism, compulsive behavior, and substance addiction. In certain embodiments, treatment comprises slowing or delaying the progression of the CNS disorder. In certain embodiments, treatment comprises preventing, slowing, or delaying the progression of cognitive impairment associated with the CNS disorder. In certain embodiments, treatment comprises reducing the rate of decline of cognitive function associated with the CNS disorder. In certain embodiments, treatment comprises alleviation, amelioration or slowing the progression, of one or more symptoms associated with the CNS disorder, such as cognitive impairment.

Methods of Assessing Cognitive Impairment

Animal models serve as an important resource for developing and evaluating treatments for cognitive impairment associated with CNS disorders. Features that characterize cognitive impairment in animal models typically extend to cognitive impairment in humans. Efficacy in such animal models is, thus, expected to be predictive of efficacy in humans. The extent of cognitive impairment in an animal model for a CNS disorder, and the efficacy of a method of treatment for said CNS disorder may be tested and confirmed with the use of a variety of cognitive tests.

A Radial Arm Maze (RAM) behavioral task is one example of a cognitive test, specifically testing spacial memory (Chappell et al. *Neuropharmacology* 37: 481-487, 1998). The RAM apparatus consists of, e.g., eight equidistantly spaced arms. A maze arm projects from each facet of a center platform. A food well is located at the distal end of each arm. Food is used as a reward. Blocks can be positioned to prevent entry to any arm. Numerous extra maze cues surrounding the apparatus may also be provided. After habituation and training phases, spatial memory of the subjects may be tested in the RAM under control or test compound-treated conditions. As a part of the test, subjects are pretreated before trials with a vehicle control or one of a range of dosages of the test compound. At the beginning of each trial, a subset of the arms of the eight-arm maze is blocked. Subjects are allowed to obtain food on the unblocked arms to which access is permitted during this initial "information phase" of the trial. Subjects are then removed from the maze for a delay period, e.g., a 60 second delay, a 15 minute delay, a one-hour delay, a two-hour delay, a six hour delay, a 24 hour delay, or longer) between the information phase and the subsequent "retention test," during which the barriers on the maze are removed, thus allowing access to all eight arms. After the delay period, subjects are placed back onto the center platform (with the barriers to the previously blocked arms removed) and allowed to obtain the remaining food rewards during this retention test phase of the trial. The identity and configuration of the blocked arms vary across trials. The number of "errors" the subjects make during the retention test phase is tracked. An error occurs in the trial if the subjects entered an arm from which food had already been retrieved in the pre-delay component of the trial, or if it re-visits an arm in the post-delay session that had already been visited. A fewer number of errors would indicate better spatial memory. The number of errors made by the test subject, under various test compound treatment regimes, can then be compared for efficacy of the test compound in treating cognitive impairment associated with CNS disorders.

Another cognitive test that may be used to assess the effects of a test compound on the cognitive impairment of a CNS disorder model animal is the Morris water maze. A water maze is a pool surrounded with a novel set of patterns relative to the maze. The training protocol for the water maze may be based on a modified water maze task that has been shown to be hippocampal-dependent (de Hoz et al., *Eur. J Neurosci.*, 22:745-54, 2005; Steele and Morris, *Hippocampus* 9:118-36, 1999). The subject is trained to locate a submerged escape platform hidden underneath the surface of the pool. During the training trial, a subject is released in the maze (pool) from random starting positions around the perimeter of the pool. The starting position varies from trial to trial. If the subject does not locate the escape platform within a set time, the experimenter guides and places the subject on the platform to "teach" the location of the platform. After a delay period following the last training trial, a retention test in the absence of the escape platform is given to assess spatial memory. The subject's level of preference for the location of the (now absent) escape platform, as measured by, e.g., the time spent in that location or the number of crossings of that location made by the mouse, indicates better spatial memory, i.e., treatment of cognitive impairment. The preference for the location of the escape platform under different treatment conditions, can then be compared for efficacy of the test compound in treating cognitive impairment associated with CNS disorders.

There are various tests known in the art for assessing cognitive function in humans, for example and without limitation, the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or MATRICS consensus neuropsychological test battery which includes tests of working memory, speed of processing, attention, verbal learning, visual learning, reasoning and problem solving and social cognition. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994, or MATRICS consensus neuropsychological test battery which includes tests of working memory, speed of processing, attention, verbal learning, visual learning, reasoning and problem solving and social cognition. Another example of a cognitive test in humans is the explicit 3-alternative forced choice task. In this test, subjects are presented with color photographs of common objects consisting of a mix of three types of image pairs: similar pairs, identical pairs and unrelated foils. The second of the pair of similar objects is referred to as the "lure". These image pairs are fully randomized and presented individually as a series of images. Subjects are instructed to make a judgment as to whether the objects seen are new, old or similar. A "similar" response to the presentation of a lure stimulus indicates successful memory retrieval by the subject. By contrast, calling the lure stimulus "old" or "new" indicates that correct memory retrieval does not occur.

In addition to assessing cognitive performance, the progression of age-related cognitive impairment and dementia, as well as the conversion of age-related cognitive impairment into dementia, may be monitored by assessing surrogate changes in the brain of the subject. Surrogate changes include, without limitation, changes in regional brain volumes, perforant path degradation, and changes seen in brain function through resting state fMRI (R-fMRI) and fluorodeoxyglucose positron emission tomography (FDG-PET). Examples of regional brain volumes useful in monitoring the progression of age-related cognitive impairment and dementia include reduction of hippocampal volume and reduction in volume or thickness of entorhinal cortex. These volumes may be measured in a subject by, for example, MRI. Aisen et al., Alzheimer's & Dementia 6:239-246 (2010). Perforant path degradation has been shown to be linked to age, as well as reduced cognitive function. For example, older adults with more perforant path degradation tend to perform worse in hippocampus-dependent memory tests. Perforant path degradation may be monitored in subjects through ultrahighresolution diffusion tensor imaging (DTI). Yassa et al., PNAS 107:12687-12691 (2010). Resting-state fMRI (R-fMRI) involves imaging the brain during rest, and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, particularly those areas whose connectivity increase or decrease with age, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. Aisen et al., Alzheimer's & Dementia 6:239-246 (2010), Herholz et al., NeuroImage 17:302-316 (2002).

Age-Related Cognitive Impairment

This invention provides methods for treating age-related cognitive impairment or the risk thereof using the extended release levetiracetam compositions of the invention. In certain embodiments, treatment comprises improving cognitive function in patients with age-related cognitive impairment. In certain embodiments, treatment comprises slowing or delaying the progression of age-related cognitive impairment. In certain embodiments, treatment comprises reducing the rate of decline of cognitive function associated with age-related cognitive impairment. In certain embodiments, treatment comprises preventing or slowing the progression, of age-related cognitive impairment. In certain embodiments, treatment comprises alleviation, amelioration or slowing the progression, of one or more symptoms associated with age-related cognitive impairment. In certain embodiments, treatment of age-related cognitive impairment comprises slowing the conversion of age-related cognitive impairment (including, but not limited to MCI, ARCD and AAMI) into dementia (e.g., AD). The methods and compositions may be used for human patients in clinical applications in the treating age-related cognitive impairment in conditions such as MCI, ARCD and AAMI or for the risk thereof. The dose of the composition and dosage interval for the method is, as described herein, one that is safe and efficacious in those applications.

In some embodiments, a subject to be treated by the methods and compositions of this invention exhibits age-related cognitive impairment or is at risk of such impairment. In some embodiments, the age-related cognitive impairment includes, without limitation, Age-Associated Memory Impairment (AAMI), Mild Cognitive Impairment (MCI) and Age-related Cognitive Decline (ARCD).

Animal models serve as an important resource for developing and evaluating treatments for such age-related cognitive impairments. Features that characterize age-related cognitive impairment in animal models typically extend to age-related cognitive impairment in humans. Efficacy in such animal models is, thus, expected to be predictive of efficacy in humans.

Various animal models of age-related cognitive impairment are known in the art. For example, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Gallagher et al. *Behav. Neurosci.* 107:618-626, (1993); Rapp and Gallagher, *Proc. Natl. Acad. Sci.* 93: 9926-9930, (1996); Nicolle et al., *Neuroscience* 74: 741-756, (1996); Nicolle et al., *J. Neurosci.* 19: 9604-9610, (1999); International Patent Publication WO2007/019312 and International Patent Publication WO 2004/048551. Such an animal model of age-related cognitive impairment may be used to assay the effectiveness of the methods and compositions this invention in treating age-related cognitive impairment.

The efficacy of the methods and compositions of this invention in treating age-related cognitive impairment may be assessed using a variety of cognitive tests, including the Morris water maze and the radial arm maze, as discussed above.

Dementia

This invention also provides methods for treating dementia using the extended release levetiracetam compositions of the invention. In certain embodiments, treatment comprises improving cognitive function in patients with dementia. In certain embodiments, treatment comprises slowing or delaying the progression of dementia. In certain embodiments, treatment comprises reducing the rate of decline of cognitive function associated with dementia. In certain embodiments, treatment comprises preventing or slowing the progression, of dementia. In certain embodiments, treatment comprises alleviation, amelioration, or slowing the progression of one or more symptoms associated with dementia. In certain embodiments, the symptom to be treated is cognitive impairment. In certain embodiments, the dementia is Alzheimer's disease (AD), vascular dementia, dementia with Lewy bodies, or frontotemporal dementia. The methods and compositions may be used for human patients in clinical applications in treating dementia. The dose of the composition and dosage interval for the method is, as described herein, one that is safe and efficacious in those applications.

Animal models serve as an important resource for developing and evaluating treatments for dementia. Features that characterize dementia in animal models typically extend to dementia in humans. Thus, efficacy in such animal models is expected to be predictive of efficacy in humans. Various animal models of dementia are known in the art, such as the PDAPP, Tg2576, APP23, TgCRND8, J20, hPS2 Tg, and APP+PS1 transgenic mice. Sankaranarayanan, *Curr. Top. Medicinal Chem.* 6: 609-627, 2006; Kobayashi et al. *Genes Brain Behav.* 4: 173-196. 2005; Ashe and Zahns, Neuron. 66: 631-45, 2010. Such animal models of dementia may be used to assay the effectiveness of the methods and compositions of this invention of the invention in treating dementia.

The efficacy of the methods and compositions of this invention in treating dementia, or cognitive impairment associated with dementia, may be assessed in animals models of dementia, as well as human subjects with dementia, using a variety of cognitive tests known in the art, as discussed above.

Post Traumatic Stress Disorder

This invention also provides methods for treating post traumatic stress disorder (PTSD) using the extended release levetiracetam compositions of the invention. In certain embodiments, treatment comprises improving cognitive function in patients with PTSD. In certain embodiments, treatment comprises slowing or delaying the progression of PTSD. In certain embodiments, treatment comprises reducing the rate of decline of cognitive function associated with PTSD. In certain embodiments, treatment comprises preventing or slowing the progression, of PTSD. In certain embodiments, treatment comprises alleviation, amelioration, or slowing the progression of one or more symptoms associated with PTSD. In certain embodiments, the symptom to be treated is cognitive impairment. The methods and compositions may be used for human patients in clinical applications in treating PTSD. The dose of the composition and dosage interval for the method is, as described herein, one that is safe and efficacious in those applications.

Patients with PTSD (and, to a lesser degree trauma-exposed patients without PTSD) have smaller hippocampal volumes (Woon et al., *Prog. Neuro-Psychopharm. & Biological Psych.* 34, 1181-1188; Wang et al., *Arch. Gen. Psychiatry* 67:296-303, 2010). PTSD is also associated with impaired cognitive performance. Older individuals with PTSD have greater declines in cognitive performance relative to control patients (Yehuda et al., *Bio. Psych.* 60: 714-721, 2006) and have a greater likelihood of developing dementia (Yaffe et al., *Arch. Gen. Psych.* 678: 608-613, 2010).

Animal models serve as an important resource for developing and evaluating treatments for PTSD. Features that characterize PTSD in animal models typically extend to PTSD in humans. Thus, efficacy in such animal models is expected to be predictive of efficacy in humans. Various animal models of PTSD are known in the art.

One rat model of PTSD is Time-dependent sensitization (TDS). TDS involves exposure of the animal to a severely stressful event followed by a situational reminder of the prior stress. The following is an example of TDS. Rats are placed in a restrainer, then placed in a swim tank and made to swim for a period of time, e.g., 20 min. Following this, each rat is then immediately exposed to a gaseous anesthetic until loss of consciousness, and finally dried. The animals are left undisturbed for a number of days, e.g., one week. The rats are then exposed to a "restress" session consisting of an initial stressor, e.g., a swimming session in the swim tank (Liberzon et al., *Psychoneuroendocrinology* 22: 443-453, 1997; Harvery et al., *Psychopharmacology* 175:494-502, 2004). TDS results in an enhancement of the acoustic startle response (ASR) in the rat, which is comparable to the exaggerated acoustic startle that is a prominent symptom of PTSD (Khan and Liberzon, Psychopharmacology 172: 225-229, 2004). Such animal models of PTSD may be used to assay the effectiveness of the methods and compositions of this invention of the invention in treating PTSD.

The efficacy of the methods and compositions of this invention in treating PTSD, or cognitive impairment associated with PTSD, may also be assessed in animals models of PTSD, as well as human subjects with PTSD, using a variety of cognitive tests known in the art, as discussed above.

Schizophrenia

This invention provides methods for treating schizophrenia or bipolar disorder (in particular, mania) using the extended release levetiracetam compositions of the invention. In certain embodiments, treatment comprises improving cognitive function in patients with schizophrenia. In certain embodiments, treatment comprises slowing or delaying the progression of schizophrenia. In certain embodiments, treatment comprises reducing the rate of decline of cognitive function associated with schizophrenia. In certain embodiments, treatment comprises preventing or slowing the progression of schizophrenia or bipolar disorder (in particular, mania). Schizophrenia is characterized by a wide spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. In certain embodiments, treatment comprises alleviation, amelioration or slowing the progression of one or more positive and/or negative symptoms, as well as cognitive impairment, associated with schizophrenia. Further, there are a number of other psychiatric diseases such as schizotypical and schizoaffective disorder, other acute- and chronic psychoses and bipolar disorder (in particular, mania), which have an overlapping symptomatology with schizophrenia. In some embodiments, treatment comprises alleviation, amelioration or slowing the progression of one or more symptoms, as well as cognitive impairment, associated with bipolar disorder (in particular, mania). The methods and compositions may be used for human patients in clinical applications in treating schizophrenia or bipolar disorder (in particular, mania). The dose of the composition and dosage interval for the method is, as described herein, one that is safe and efficacious in those applications.

Cognitive impairments are associated with schizophrenia. They precede the onset of psychosis and are present in non-affected relatives. The cognitive impairments associated with schizophrenia constitute a good predictor for functional outcome and are a core feature of the disorder. Cognitive features in schizophrenia reflect dysfunction in frontal cortical and hippocampal circuits. Patients with schizophrenia also present hippocampal pathologies such as reductions in hippocampal volume, reductions in neuronal size and dysfunctional hyperactivity. An imbalance in excitation and inhibition in these brain regions has also been documented in schizophrenic patients suggesting that drugs targeting inhibitory mechanisms could be therapeutic. See, e.g., Guidotti et al., *Psychopharmacology* 180: 191-205, 2005; Zierhut, *Psych. Res. Neuroimag.* 183:187-194, 2010; Wood et al., *Neurolmage* 52:62-63, 2010; Vinkers et al., *Expert Opin. Investig. Drugs* 19:1217-1233, 2009; Young et al., *Pharmacol. Ther.* 122:150-202, 2009.

Animal models serve as an important resource for developing and evaluating treatments for schizophrenia. Features that characterize schizophrenia in animal models typically extend to schizophrenia in humans. Thus, efficacy in such animal models is expected to be predictive of efficacy in humans. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., *PNAS,* 99: 17095-17100, 2002). Another animal model of schizophrenia is methylaoxymethanol acetate (MAM)-treatment in rats. Pregnant female rats are administered MAM (20 mg/kg, intraperitoneal) on gestational day 17. MAM-treatment recapitulate a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning. (see Lodge et al., J. Neurosci., 29:2344-2354, 2009). Such animal models of schizophrenia may be used to assay the effectiveness of the methods and compositions of the invention in treating schizophrenia or bipolar disorder (in particular, mania).

MAM-treated rats display a significantly enhanced locomotor response (or aberrant locomotor activity) to low dose D-amphetamine administration. The MAM-treated rats also display a significantly greater number of spontaneously firing ventral tegmental dopamine (DA) neurons. These results are believed to be a consequence of excessive hippocampal activity because in MAM-treated rats, the ventral hippocampus (vHipp) inactivation (e.g., by intra-vHipp administration of a sodium channel blocker, tetrodotoxin (TTX), to MAM rats) completely reversed the elevated DA neuron population activity and also normalized the augmented amphetamine-induced locomotor behavior. The correlation of hippocampal dysfunction and the hyper-responsivity of the DA system is believed to underlie the augmented response to amphetamine in MAM-treated animals and psychosis in schizophrenia patients. See Lodge D. J. et al. *Neurobiology of Disease* (2007), 27(42), 11424-11430. The use of MAM-treated rats in the above study may be suitable for use to assay the effectiveness of the methods and compositions of the present invention in treating schizophrenia or bipolar disorder (in particular, mania). For example, the methods and compositions of this invention maybe evaluated, using MAM-treated animals, for their effects on the central hippocampus (vHipp) regulation, on the elevated DA neuron population activity and on the hyperactive locomotor response to amphetamine in the MAM-treated animals.

In MAM-treated rats, hippocampal (HPC) dysfunction leads to dopamine system hyperactivity. A benzodiazepine-positive allosteric modulator (PAM), selective for the α5 subunit of the $GABA_A$ receptor, SH-053-2'F—R—$CH_3$, is tested for its effects on the output of the hippocampal (HPC). The effect of SH-053-2'F—R—$CH_3$ on the hyperactive locomotor response to amphetamine in MAM-treated animals is also examined. The α5GABAAR PAM reduces the number of spontaneously active DA neurons in the ventral tegmental area (VTA) of MAM rats to levels observed in saline-treated rats (control group), both when administered systemically and when directly infused into the ventral HPC. Moreover, HPC neurons in both saline-treated and MAM-treated animals show diminished cortical-evoked responses following the α5GABAAR PAM treatment. In addition, the increased locomotor response to amphetamine observed in MAM-treated rats is reduced following the α5$GABA_AR$ PAM treatment. See Gill K. M et al. *Neuropsychopharmacology* (2011), 1-9. The use of MAM-treated rats in the above study may be suitable for use in the present invention to assay the effectiveness of the methods and compositions of the invention in treating schizophrenia or bipolar disorder (in particular, mania). For example, the methods and compositions of this invention maybe evaluated, using MAM-treated animals, for their effects on the output of the hippocampal (HPC) and on the hyperactive locomotor response to amphetamine in the MAM-treated animals.

Administration of MAM to pregnant rats on embryonic day 15 (E15) severely impairs spatial memory or the ability to learn the spatial location of four items on an eight-arm radial maze in the offspring. In addition, embryonic day 17 (E17) MAM-treated rats are able to reach the level of performance of control rats at the initial stages of training, but are unable to process and retrieve spatial information when a 30-min delay is interposed, indicating a significant impairment in working memory. See Gourevitch R. et al. (2004). *Behav. Pharmacol,* 15, 287-292. Such animal models of schizophrenia may be used to assay the effectiveness of the methods and compositions of the invention in treating schizophrenia or bipolar disorder (in particular, mania).

Apomorphine-induced climbing (AIC) and stereotype (AIS) in mice is another animal model useful in this invention. Agents are administered to mice at a desired dose level (e.g., via intraperitoneal administration). Subsequently, e.g., thirty minutes later, experimental mice are challenges with apomorphine (e.g., with 1 mg/kg sc). Five minutes after the apomorphine injection, the sniffing-licking-gnawing syndrome (stereotyped behavior) and climbing behavior induced by apomorphine are scored and recorded for each animal. Readings can be repeated every 5 min during a 30-min test session. Scores for each animal are totaled over the 30-min test session for each syndrome (stereotyped behavior and climbing). If an effect reached at least of 50% inhibition, and $ID_{50}$ value (95% confidence interval) is calculated using a nonlinear least squares calculation with inverse prediction. Mean climbing and stereotype scores can be expressed as a percent of control values observed in vehible treated (e.g., saline-treated) mice that receive apomorphine. See Grauer S. M. et al. *Psychopharmacology* (2009) 204, 37-48. This mice model may be used to assay the effectiveness of the methods and compositions of the invention in treating schizophrenia or bipolar disorder (in particular, mania).

The efficacy of the methods and compositions of this invention in treating schizophrenia may also be assessed in animal models of schizophrenia or bipolar disorder (in particular, mania), as well as human subjects with schizophrenia, using a variety of cognitive tests known in the art, as discussed above.

Amyotrophic Lateral Sclerosis (ALS)

This invention additionally provides methods for treating ALS using the extended release levetiracetam compositions of the invention. In certain embodiments, treatment comprises improving cognitive function in patients with ALS. In certain embodiments, treatment comprises slowing or delaying the progression of ALS. In certain embodiments, treatment comprises reducing the rate of decline of cognitive function associated with ALS. In certain embodiments, treatment comprises preventing or slowing the progression, of ALS. In certain embodiments, treatment comprises alleviation, amelioration or slowing the progression, of one or more symptoms associated with ALS. In certain embodiments, the symptom to be treated is cognitive impairment. The methods and compositions may be used for human patients in clinical applications in treating ALS. The dose of the composition and dosage interval for the method is, as described herein, one that is safe and efficacious in those applications.

In addition to the degeneration of motor neurons, ALS is characterized by neuronal degeneration in the entorhinal cortex and hippocampus, memory deficits, and neuronal hyperexcitability in different brain areas such as the cortex.

The efficacy of the methods and compositions of this invention in treating ALS, or cognitive impairment associated with ALS, may also be assessed in animal models of ALS, as well as human subjects with ALS, using a variety of cognitive tests known in the art, as discussed above.

Cancer Therapy-Related Cognitive Impairment

This invention additionally provides methods for treating cancer therapy-related cognitive impairment using the extended release levetiracetam compositions of the invention. In certain embodiments, treatment comprises improving cognitive function in patients with cancer therapy-related cognitive impairment. In certain embodiments, treatment comprises slowing or delaying the progression of cancer therapy-related cognitive impairment. In certain embodiments, treatment comprises reducing the rate of decline of cognitive function associated with cancer therapy-related cognitive impairment. In certain embodiments, treatment comprises preventing or slowing the progression, of cancer therapy-related cognitive impairment. In certain embodiments, treatment comprises alleviation, amelioration or slowing the progression, of one or more symptoms associated with cancer therapy-related cognitive impairment. The methods and compositions may be used for human patients in clinical applications in treating cancer therapy-related cognitive impairment. The dose of the composition and dosage interval for the method is, as described herein, one that is safe and efficacious in those applications.

Therapies that are used in cancer treatment, including chemotherapy, radiation, or combinations thereof, can cause cognitive impairment in patients, in such functions as memory, learning and attention. Cytotoxicity and other adverse side-effects on the brain of cancer therapies are the basis for this form of cognitive impairment, which can persist for decades. (Dietrich et al., Oncologist 13:1285-95, 2008; Soussain et al., Lancet 374:1639-51, 2009).

Cognitive impairment following cancer therapies reflects dysfunction in frontal cortical and hippocampal circuits that are essential for normal cognition. In animal models, exposure to either chemotherapy or radiation adversely affects performance on tests of cognition specifically dependent on these brain systems, especially the hippocampus (Kim et al., J. Radiat. Res. 49:517-526, 2008; Yang et al., Neurobiol. Learning and Mem. 93:487-494, 2010). Thus, drugs targeting these cortical and hippocampal systems could be neuroprotective in patients receiving cancer therapies and efficacious in treating symptoms of cognitive impairment that may last beyond the interventions used as cancer therapies.

Animal models serve as an important resource for developing and evaluating treatments for cancer therapy-related cognitive impairment. Features that characterize cancer therapy-related cognitive impairment in animal models typically extend to cancer therapy-related cognitive impairment in humans. Thus, efficacy in such animal models is expected to be predictive of efficacy in humans. Various animal models of cancer therapy-related cognitive impairment are known in the art.

Examples of animal models of cancer therapy-related cognitive impairment include treating animals with antineoplastic agents such as cyclophosphamide (CYP) or with radiation, e.g., $^{60}$Co gamma-rays. (Kim et al., *J. Radiat. Res.* 49:517-526, 2008; Yang et al., Neurobiol. *Learning and Mem.* 93:487-494, 2010). The cognitive function of animal models of cancer therapy-related cognitive impairment may then be tested with cognitive tests to assay the effectiveness of the methods and compositions of the invention in treating cancer therapy-related cognitive impairment. The efficacy of the methods and compositions of this invention in treating cancer therapy-related cognitive impairment, as well as human subjects with cancer therapy-related cognitive impairment, using a variety of cognitive tests known in the art, as discussed above.

Parkinson's Disease (PD)

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

Parkinson's disease, the etiology of which is unknown, belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics. Nonetheless, it is believed that the inappropriate loss of synaptic stability may lead to the disruption of neuronal circuits and to brain diseases. Whether as the result of genetics, drug use, the aging process, viral infections, or other various causes, dysfunction in neuronal communication is considered the underlying cause for many neurologic diseases, such as PD (Myrrhe van Spronsen and Casper C. Hoogenraad. *Curr Neurol. Neurosci. Rep.* 2010, 10, 207-214).

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

This invention provides methods for treating PD using the extended release levetiracetam composition of the invention. In certain embodiments, treatment comprises preventing or slowing the progression of PD. In certain embodiments, treatment comprises alleviation, amelioration, or slowing the progression of one or more symptoms associated with PD. In certain embodiments, the symptom to be treated is cognitive impairment. For example, methods and compositions of the disclosure can be used to improve the motor/cognitive impairments symptomatic of Parkinson's disease. Moreover, methods and compositions of the disclosure may be useful for treating the memory impairment symptomatic of Parkinson's disease.

There are a number of animal models for PD. Exemplary animal models for PD include the reserpine model, the methamphetamine model, the 6-hydroxydopamine (6-OHDA) model, the 1-methyl-4-phenyl-1,2,3,6-tetrahydropyridine (MPTP) model, the paraquat (PQ)-Maneb model, the rotenone model, the 3-nitrotyrosine model and genetic models using transgenic mice. Transgenic models include mice that over express α-synuclein, express human mutant forms of α-synuclein, or mice that express LRKK2 mutations. See review of these models by Ranjita B. et al. (Ranjita B. et al. *BioEssays* 2002, 24, 308-318). Additional information regarding these animal models is readily available from Jackson Laboratories (see also http://research.jax.org/grs/parkinsons.html), as well as in numerous publications disclosing the use of these validated models.

The efficacy of the methods and compositions of this invention in treating PD, or cognitive impairment associated with PD, may be assessed in any of the above animal models of PD, as well as human subjects with PD, using a variety of cognitive tests known in the art, as discussed above.

Autism

"Autism"; as used herein, refers to an autism spectrum disorder characterized by a neural development disorder leading to impaired social interaction and communication by restricted and repetitive behavior. "Autism Spectrum Disorder" refers to a group of developmental disabilities that includes: autism; Asperger syndrome; pervasive developmental disorder not otherwise specified (PDD-NOS or atypical autism); Rett syndrome; and childhood disintegrative disorder.

Autism is a neurodevelopmental disorder characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities. Autism is a disabling neurological disorder that affects thousands of Americans and encompasses a number of subtypes, with various putative causes and few documented ameliorative treatments. The disorders of the autistic spectrum may be present at birth, or may have later onset, for example, at ages two or three. There are no clear cut biological markers for autism. Diagnosis of the disorder is made by considering the degree to which the child matches the behavioral syndrome, which is characterized by poor communicative abilities, peculiarities in social and cognitive capacities, and maladaptive behavioral patterns. The dysfunction in neuronal communication is considered one of the underlying causes for autism (Myrrhe van Spronsen and Casper C. Hoogenraad, Curr. Neurol. Neurosci. Rep. 2010, 10, 207-214).

This invention provides methods for treating autism using the extended release levetiracetam composition of the invention. In certain embodiments, treatment comprises preventing or slowing the progression of autism. In certain embodiments, treatment comprises alleviation, amelioration, or slowing the progression of one or more symptoms associated with autism. In certain embodiments, the symptom to be treated is cognitive deficit. For example, methods and compositions of the disclosure can be used to improve the motor/cognitive deficits symptomatic of autism.

Mental Retardation

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, Curr. Neurol. Neurosei. Rep. 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

The present invention contemplates the treatment of mild mental retardation, moderate mental retardation, severe mental retardation, profound mental retardation, and mental retardation severity unspecified. Such mental retardation may be, but is not required to be, associated with chromosomal changes, (for example Down Syndrome due to trisomy 21), heredity, pregnancy and perinatal problems, and other severe mental disorders. This invention provides methods for treating mental retardation using the extended release levetiracetam composition of the invention. In certain embodiments, treatment comprises preventing or slowing the progression of mental retardation. In certain embodiments, treatment comprises alleviation, amelioration, or slowing the progression of one or more symptoms associated with mental retardation. In certain embodiments, the symptom to be treated is cognitive deficit/impairment. For example, methods and compositions of the disclosure can be used to improve the motor/cognitive impairments symptomatic of mental retardation.

Several animal models have been developed for mental retardation. For example, a knockout mouse model has been developed for Fragile X syndrome. Fragile X syndrome is a common form of mental retardation caused by the absence of the FMR1 protein, FMRP. Two homologs of FMRP have been identified, FXR1P and FXR2P. FXR2P shows high expression in brain and testis, like FMRP. Both Fxr2 and Fmr1 knockout mice, and Fmr1/Fxr2 double knockout mice are believed to be useful models for mental retardation such as Fragile X syndrome. See, Bontekoe C. J. M. et al. Hum. Mol. Genet. 2002, 11 (5): 487-498. The efficacy of the methods and compositions of this invention in treating mental retardation, or cognitive deficit/impairment associated with mental retardation, may be assessed in the these mouse models and other animal models developed for mental retardation, as well as human subjects with mental retardation, using a variety of cognitive tests known in the art, as discussed above.

Compulsive Behavior (Obsessive Compulsive Disorder)

Obsessive compulsive disorder ("CCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD) is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000)

diagnostic criteria that include characteristics of obsessions and compulsions. Characteristics of obsession include: (1) recurrent and persistent thoughts, impulses, or images that are experienced as intrusive and that cause marked anxiety or distress; (2) the thoughts, impulses, or images are not simply excessive worries about real-life problems; and (3) the person attempts to ignore or suppress such thoughts, impulses, or images, or to neutralize them with some other thought or action. The person recognizes that the obsessional thoughts, impulses, or images are a product of his or her own mind, and are not based in reality. Characteristics of compulsion include: (1) repetitive behaviors or mental acts that the person feels driven to perform in response to an obsession, or according to rules that must be applied rigidly; (2) the behaviors or mental acts are aimed at preventing or reducing distress or preventing some dreaded event or situation; however, these behaviors or mental acts are not actually connected to the issue, or they are excessive.

Individuals with OCD typically perform tasks (or compulsion) to seek relief from obsession-related anxiety. Repetitive behaviors such as handwashing, counting, checking, or cleaning are often performed with the hope of preventing obsessive thoughts or making them go away. Performing these "rituals," however, only provides temporary relief. People with OCD may also be diagnosed with a spectrum of other mental disorders, such as generalized anxiety disorder, anorexia nervosa, panic attack, or schizophrenia.

The dysfunction in neuronal communication is considered one of the underlying causes for obsession disorder (Myrrhe van Spronsen and Casper C. Hoogenraad, *Curr. Neurol. Neurosci. Rep.* 2010, 10, 207-214), Studies suggest that OCD may be related to abnormal levels of a neurotransmitter called serotonin. The first-line treatment of OCD consists of behavioral therapy, cognitive therapy, and medications. Medications for treatment include serotonin reuptake inhibitors (SRIs) such as paroxetine (Seroxat™, Paxil®, Xetanor™, ParoMerck™, Rexetin™), sertraline (Zoloft®, Stimuloton™), fluoxetine (Prozac®, Bioxetin™), escitalopram (Lexapro®), and fluvoxamine (Luvox®) as well as the tricyclic antidepressants, in particular clomipramine (Anafranil®). Benzodiazepines are also used in treatment. As much as 40 to 60% of the patients, however, fail to adequately respond to the SRI therapy and an even greater proportion of patients fail to experience complete remission of their symptoms.

This invention provides methods for treating OCD using the extended release levetiracetam composition of the invention. In certain embodiments, treatment comprises preventing or slowing the progression of OCD. In certain embodiments, treatment comprises alleviation, amelioration, or slowing the progression of one or more symptoms associated with OCD. In certain embodiments, the symptom to be treated is cognitive deficit. For example, methods and compositions of the disclosure can be used to treat the cognitive deficits in OCD, and/or to improve cognitive function in patients with OCD. A quinpirole-sensitized rat model has been developed for OCD. The compulsive checking behavior of the quinpirole-sensitized rats is subject to interruption, which is an attribute characteristic of OCD compulsions. The efficacy of the methods and compositions of this invention in treating OCD, or cognitive deficits associated with OCD, may be assessed in this rat model and other animal models developed for OCD, as well as human subjects with OCD, using a variety of cognitive tests known in the art, as discussed above.

Substance Addiction

Substance addiction e.g., drug substance addiction, alcohol substance addiction) is a mental disorder. The substance addiction is not triggered instantaneously upon exposure to substnace of abuse. Rather, it involves multiple, complex neural adaptations that develop with different time courses ranging from hours to days to months (Kauer J. A. *Nat. Rev. Neurosci.* 2007, 8, 844-858). The path to substance addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g, alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize substance addictions to other controlled substances. The craving for alcohol, as well as other controlled substances, often is as strong as the need for food or water. Thus, an alcoholic may continue to drink despite serious family, health and/or legal ramifications.

Recent work exploring the effects of abusing alcohol, central stimulants, and opiates on the central nervous system (CNS) have demonstrated a variety of adverse effects related to mental health, including substance-induced impairments in cognition. See, Nyberg F. *Cognitive Impairments in Drug Addicts*, Chapter 9. In several laboratories and clinics substantial damages of brain function are seen to result from these drugs. Among the harmful effects of the abusing drugs on brain are those contributing to accelerated obsolescence. An observation that has received special attention during recent years is that chronic drug users display pronounced impairment in brain areas associated with executive and memory function. A remarked neuroadaptation caused by addictive drugs, such as alcohol, central stimulants and opiates involves diminished neurogenesis in the subgranular zone (SGZ) of the hippocampus. Indeed, it has been proposed that decreased adult neurogenesis in the SGZ could modify the hippocampal function in such a way that it contributes to relapse and a maintained addictive behavior. It also raises the possibility that decreased neurogenesis may contribute to cognitive deficits elicited by these abusing drugs.

This invention provides methods for treating substance addiction using the extended release levetiracetam composition of the invention. In certain embodiments, treatment comprises preventing or slowing the progression of substance addiction. In certain embodiments, treatment comprises alleviation, amelioration, or slowing the progression of one or more symptoms associated with substance addiction. In certain embodiments, the symptom to be treated is cognitive impairment. For example, methods and compositions of the disclosure can be used to treat the cognitive impairment and/or to improve cognitive function in patients with substance addiction.

Several animal models have been developed to study substance addiction. For example, a genetically selected Marchigian Sardinian alcohol-preferring (msP) rat models is developed to study the neurobiology of alcoholism. See, Ciccocioppo R. et al. *Substance addiction Biology* 2006, 11, 339-355. The efficacy of the methods and compositions of this invention in treating substance addiction, or cognitive impairment associated with substance addiction, may also be assessed in animal models of substance addiction, as well as human subjects with substance addiction, using a variety of cognitive tests known in the art, as discussed above.

Appropriate methods of administering the extended release compositions of the invention will also depend, for example, on the age of the subject, whether the subject is active or inactive at the time of administering, whether the subject is cognitively impaired at the time of administering, or the extent of the impairment. In some embodiments, the extended release levetiracetam composition of the invention is administered orally, e.g., to a subject by ingestion. In some embodiments, the orally administered composition is administered using a device for extended release.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This invention will be better understood from the Experimental Details which follow. However, one skilled in the art will readily appreciate that the specific methods and results discussed are merely illustrative of the invention as described more fully in the embodiments which follow thereafter.

EXAMPLES

Example 1: A Process for Making Extended Release Compositions Comprising 190 mg of Levetiracetam

TABLE 1

| Ingredient | Functionality | Tablet A (Mg/Tablet) | Tablet B (Mg/Tablet) | Tablet C (Mg/Tablet) |
| --- | --- | --- | --- | --- |
| Levetiracetam Base | API | 190.0 | 190.0 | 190.0 |
| Hypromellose (Methocel ™ K15M CR) | Matrix Former | 300.0 | — | — |
| Hypromellose (Methocel ™ K100M Premium CR) | Matrix Former | — | 300.0 | 300.0 |
| Colloidal Silicon Dioxide | Glidant | 1.2 | 1.2 | 1.2 |
| Silicified Microcrystalline Cellulose ProSolv ™ HD90 | Diluent | 102.8 | 102.8 | — |
| Encompress, Anhydrous dicalcium phosphate | Diluent | — | — | 102.8 |
| Magnesium Stearate | Lubricant | 6.0 | 6.0 | 6.0 |
| Total | | 600 | 600 | 600 |

Figure 9:
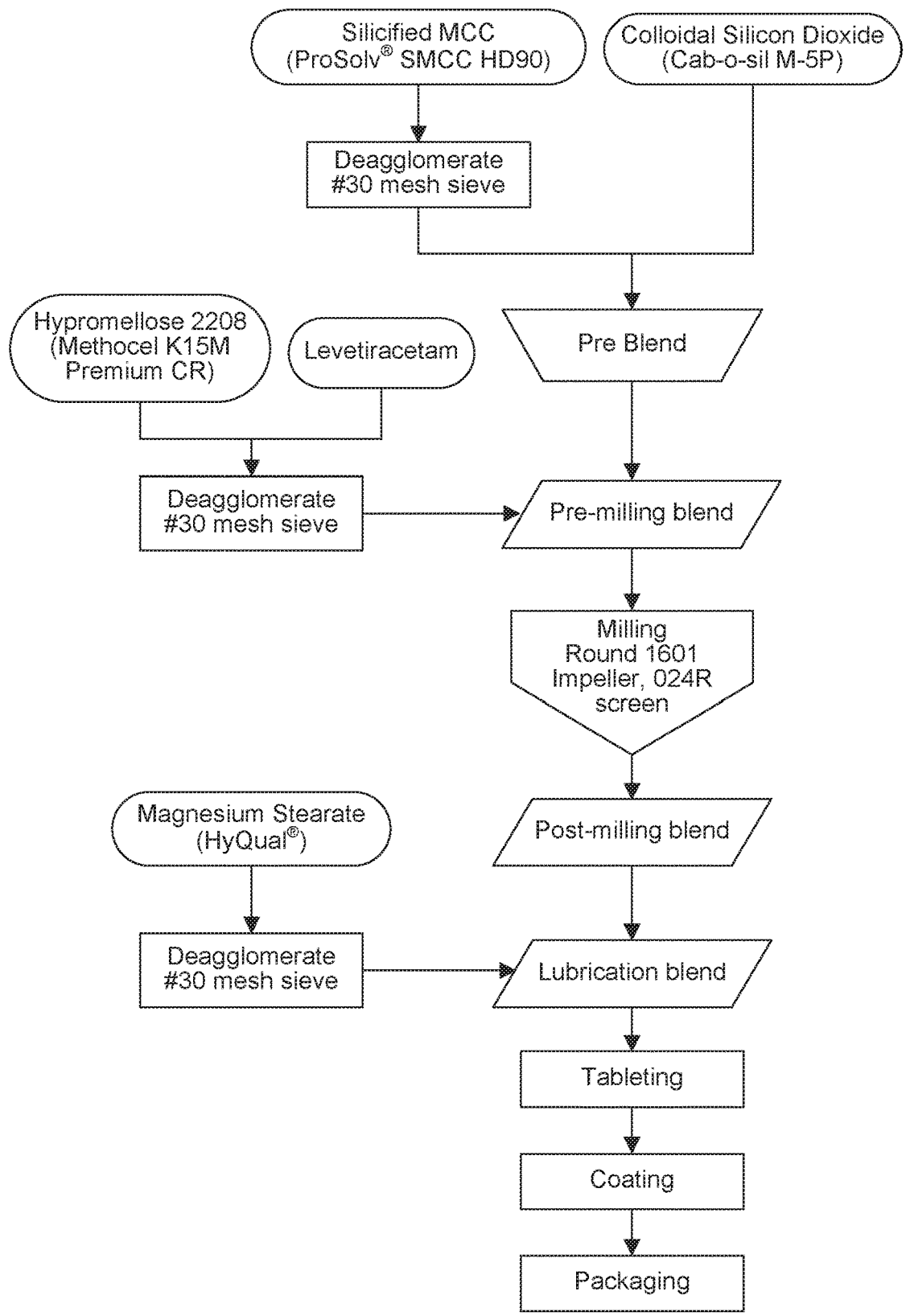
FIG. 9 is a flow diagram of another embodiment of a process for manufacturing extended release compositions of levetiracetam (e.g., 190 mg and 220 mg tablets listed in Tables 1 and 3).

Three extended release tablets A, B, and C comprising 190 mg of levetiracetam as shown in Table 1 are manufactured following the process exemplified in the flow diagram of FIG. 1. The process exemplified in the flow diagram of FIG. 9 could also be used. In brief, Silicified Microcrystalline Cellulose ProSolv™ SMCC HD90 (or Encompress, Anhydrous dicalcium phosphate) is sifted through deagglomerate #30 U.S. mesh sieve, and then blended with Colloidal Silicon Dioxide (16 qt V-shell blender; 75 rev±5 rev). The blended sample then goes through Round 1601 Impeller (2A024R screen). 190 mg of levetiracetam and hypromellose 2208 (Methocel™ K15M Premium CR) (or Methocel™ K100M Premium CR) are also sifted through deagglomerate #30 U.S. mesh sieve, and then blended in a 1 ft³ Slant Cone Blender (250 rev±5 rev) with the ground Silicified Microcrystalline Cellulose ProSolv™ HD90 and Colloidal Silicon Dioxide. This blended sample then goes through Round 1601 Impeller (2A024R screen) and then is blended in a 1 ft³ Slant Cone Blender (125 rev±5 rev) with sieved Magnesium Stearate (HyQual®) (sieved through deagglomerate #30 U.S. mesh sieve). The blended samples are compressed into tablets. Optionally, the tablets are further film coated with a hypromellose-based (HPMC-based) coating, such as Opadry® complete film coating system.

Example 2: Dissolution Profile of Extended Release Compositions Comprising 190 mg of Levetiracetam Table 2 below shows the dissolution profile for the 190 mg levetiracetam extended release Tablet A of Table 1.

TABLE 2

| Test | Results (Time: Percentages of dissolution) |
| --- | --- |
| Dissolution | 1 hr: 29% |
| | 3 hr: 51% |
| | 12 hr: 92% |

When extended release Tablet A is placed in variety of EtOH concentrations in 0.1N HCL, no dose dumping is observed.

Example 3: A Process for Making Extended Release Compositions Comprising 220 mg of Levetiracetam

TABLE 3

| Ingredient | Functionality | Tablet D (Mg/Tablet) | Tablet E (Mg/Tablet) |
| --- | --- | --- | --- |
| Levetiracetam | API | 220.0 | 220.0 |
| Hypromellose (Methocel ™ K15M CR) | Matrix Former | 280.0 | 347.5 |
| Colloidal Silicon Dioxide | Glidant | 1.2 | 1.4 |
| Silicified Microcrystalline Cellulose ProSolv ™ HD90 | Diluent | 92.8 | 119.2 |
| Magnesium Stearate | Lubricant | 6.0 | 6.7 |
| Total | | 600 | 695 |

Two extended release tablets D and E comprising 220 mg of levetiracetam as shown in Table 3 are manufactured following the process exemplified in the flow diagram of FIG. 1. The process exemplified in the flow diagram of FIG. 9 could also be used. In brief, Silicified Microcrystalline Cellulose ProSolv™ SMCC HD90 (or Encompress, Anhydrous dicalcium phosphate) is sifted through deagglomerate #30 U.S. mesh sieve, and then blended with Colloidal Silicon Dioxide (16 qt V-shell blender; 75 rev±5 rev). The blended sample then goes through Round 1601 Impeller (2A024R screen). 220 mg of levetiracetam and hypromellose 2208 (Methocel™ K15M Premium CR) (or Methocel™ K100M Premium CR) are also sifted through deagglomerate #30 U.S. mesh sieve, and then blended in a 1 ft$^3$ Slant Cone Blender (250 rev±5 rev) with the ground Silicified Microcrystalline Cellulose ProSolv™ HD90 and Colloidal Silicon Dioxide. This blended sample then goes through Round 1601 Impeller (2A024R screen) and then is blended in a 1 ft$^3$ Slant Cone Blender (125 rev±5 rev) with sieved Magnesium Stearate (HyQual®) (sieved through deagglomerate #30 U.S. mesh sieve). The blended samples are compressed into tablets. Optionally, the tablets are further film coated with a hypromellose-based (HPMC-based) coating, such as Opadry® complete film coating system.

Example 4: Dissolution Profile of Extended Release Compositions Comprising 220 mg of Levetiracetam Table 4 below shows the dissolution profile for the 220 mg levetiracetam extended release Tablet D of Table 3.

TABLE 4

| Test | Results (Time: Percentages of dissolution) |
|---|---|
| Dissolution | 1 hr: 28% |
|  | 3 hr: 49% |
|  | 12 hr: 91% |

When extended release Tablet D is placed in variety of EtOH concentrations in 0.1N HCL, no dose dumping is observed.

Example 5: Evaluation of Extended Release Compositions of 190 mg Levetiracetam on Pharmacokinetics in Dogs Overview The purpose of this study is to collect samples for investigating the pharmacokinetics of novel extended release formulations of levetiracetam (190 mg) in male dogs following oral administration. Table 1 provides a description of the three formulations utilized in this study (190 mg Tablets A, B, and C).

Animals

Thirty non-naïve male purebred beagle dogs from the Covance Stock colony are used in these studies. The animals are acclimated to study conditions for approximately three days prior to dose administration. At dosing, the animals weigh 8.4 to 12.8 kg and are 1 to 2 years of age. All animals are housed in individual, stainless steel cages during acclimation and the test period, except during periods of commingling in accordance with Covance SOPs. Certified Harlan Teklad 2021, 21% Protein Dog Diet is provided ad libitum unless otherwise specified for dose administration. Water is provided fresh daily, ad libitum. Environmental controls for the animal room are set to maintain a temperature of 68 to 79° F., a relative humidity of 50±20%, and a 12-hour light/12-hour dark cycle. As necessary, the 12-hour dark cycle is interrupted to accommodate study procedures.

Study Design

Five groups of dogs (N=6 per group) are utilized in this study. An immediate release 250 mg levetiracetam (LEV IR) tablet is administered as a 250 mg oral BID regimen (a total dose of 500). An extended release 500 mg levetiracetam tablet (LEV XR) is administered as a single oral dose of 500 mg. Tablets A, B, and C are administered as single oral doses of 190 mg. Plasma pharmacokinetic samples are collected at pre-dose, 0.25, 0.5, 1, 2, 4, 6, 8, 12, 13 (collecting only LEV IR), 18, 24, and 48 hours post dose. For LEV IR, the 12-hour blood sample is collected just prior to administration of the second dose.

TABLE 5

Overview of Study Design

| Group | Number of Male Animals | Test Article | Dose Route | Target Dose Level (mg/tablet) |
|---|---|---|---|---|
| 1 | 6 | LEV-IR | Oral Tablet | 250 |
| 2 | 6 | LEV-XR | Oral Tablet | 500 |
| 3 | 6 | Tablet A | Oral Tablet | 190 |
| 4 | 6 | Tablet B | Oral Tablet | 190 |
| 5 | 6 | Tablet C | Oral Tablet | 190 |

IR Immediate release.
XR Extended release.
Notes:
Animals in Group 1 receive two 250 mg tablets, approximately 12 hours apart (500 mg total dose). Animals in Groups 2 through 5 receive a single tablet.

Analytical Methods

Sample analysis is performed using a Covance-owned generic method and analog internal standard. The method is adjusted as appropriate for the specific test article used on study. Data collection and chromatographic interpretation is performed in Analyst and the Laboratory Information Management System (LIMS) used on study is Watson.

Absorption and Plasma Levels

Figure 2:
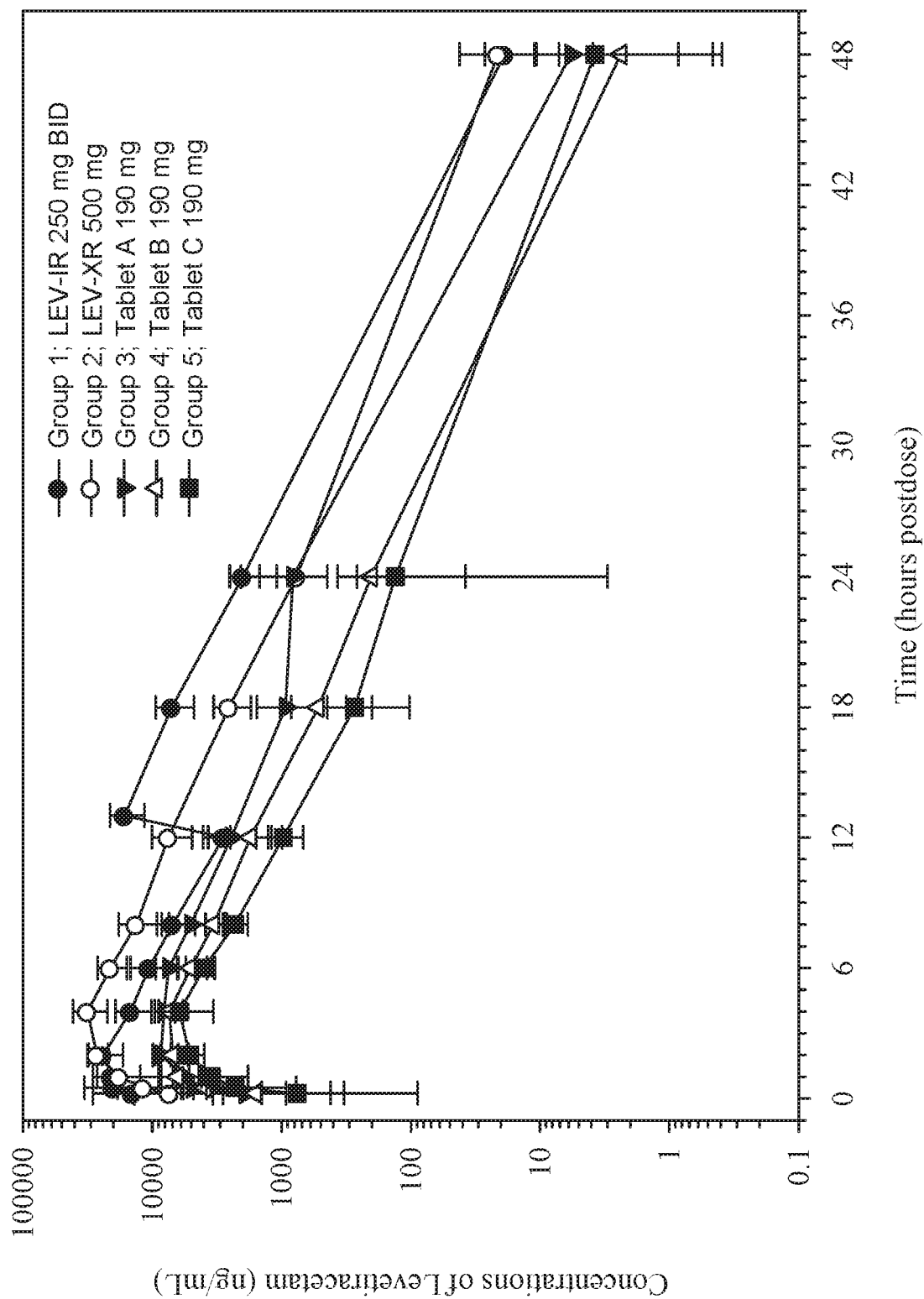
FIG. 2 shows the mean concentrations of different levetiracetam formulations in plasma following oral administration to male dogs. The tested levetiracetam formulations are: an immediate release 250 mg levetiracetam (LEV-IR) tablet being administered as 250 mg oral BID (twice daily) regimen (total dose of 500 mg); an extended release 500 mg levetiracetam tablet (LEV-XR) being administered as a single oral dose of 500 mg; the 190 mg Tablets A, B, and C of Table 1 being administered as single oral doses of 190 mg. Plasma pharmacokinetic samples are collected at pre-dose (i.e., 0), 0.25, 0.5, 1, 2, 4, 6, 8, 12, 13 (LEV-IR 250 mg BID only), 18, 24, and 48 hours post dose. For LEV-IR 250 mg BID, the 12-hour blood sample is collected just prior to administration of the second dose.

LEV IR vs. LEV XR: LEV IR is administered as a 250 mg oral BID regimen (total daily dose of 500 mg). LEV XR is administered as a single oral dose of 500 mg. Based on mean plasma C. and $AUC_{0-inf}$, the overall exposure of dogs to levetiracetam is similar with both formulations (FIG. 2, Table 6). The plasma $T_{max}$ is earlier with the IR formulation (range 0.25-2.00 h; mean 1.00 h) than with the XR formulation (range 2.00-4.00 h; mean 3.33 h). The apparent elimination half-life of levetiracetam in plasma averages 3.50±0.273 h and 4.23±0.590 h with the LEV IR and LEV XR formulations, respectively.

190 mg Tablets A, B, and C: 190 mg Tablets A, B, and C of Table 1 are administered as single oral doses of 190 mg. The highest exposure to levetiracetam is achieved with Tablet A (FIG. 2, Table 6); plasma $C_{max}$ and $AUC_{0-inf}$ averaged 8650±1440 ng/mL and 90000±27200 ng·h/mL, respectively. The plasma $T_{max}$ generally range from 2.00 to 4.00 hours. The apparent elimination half-life of levetiracetam in plasma average 4.15±1.26 h.

TABLE 6

Pharmacokinetic parameters in plasma collected from male dogs following oral administration of levetiracetam

| Animal Number | Group | $C_{max}$ (ng/mL) | $C_{max}/D$ ((ng/mL)/mg) | $T_{max}$ (h) | $AUC_{0-t}$ (h · ng/mL) | $AUC_{0-inf}$ (h · ng/mL) | $AUC_{0-inf}/D$ ((h · ng/mL)/mg) | $t_{1/2}$ (h) |
|---|---|---|---|---|---|---|---|---|
| 250 mg BID (LEV-IR) | | | | | | | | |
| 112515 | 1 | 29200 | 58.4 | 0.50 | 247000 | 247000 | 493 | 3.32 |
| 113624 | 1 | 23200 | 46.4 | 0.25 | 237000 | 237000 | 474 | 3.45 |
| 113626 | 1 | 31400 | 62.8 | 0.25 | 302000 | 302000 | 604 | 3.44 |
| 113648 | 1 | 38100 | 76.2 | 2.00 | 277000 | 277000 | 554 | 3.15 |
| 113627 | 1 | 24300 | 48.6 | 2.00 | 280000 | 280000 | 560 | 3.83 |
| 113614 | 1 | 24500 | 49.0 | 1.00 | 214000 | 214000 | 428 | 3.82 |
| | Mean | 28500 | 56.9 | 1.00 | 259000 | 259000 | 519 | 3.50 |
| | SD | 5710 | 11.4 | 0.822 | 32400 | 32400 | 64.8 | 0.273 |
| 500 mg (LEV-XR) | | | | | | | | |
| 113637 | 2 | 36900 | 73.8 | 4.00 | 218000 | 218000 | 436 | 3.73 |
| 113643 | 2 | 25000 | 50.0 | 2.00 | 265000 | 265000 | 531 | 5.19 |
| 113646 | 2 | 31600 | 63.2 | 4.00 | 302000 | 302000 | 604 | 4.16 |
| 112513 | 2 | 35400 | 70.8 | 2.00 | 317000 | 317000 | 634 | 3.74 |
| 113638 | 2 | 24900 | 49.8 | 4.00 | 230000 | 230000 | 460 | 4.69 |
| 113615 | 2 | 44300 | 88.6 | 4.00 | 287000 | 287000 | 574 | 3.89 |
| | Mean | 33000 | 66.0 | 3.33 | 270000 | 270000 | 540 | 4.23 |
| | SD | 7490 | 15.0 | 1.03 | 39600 | 39600 | 79.1 | 0.590 |
| 190 mg (Tablet A) | | | | | | | | |
| 112417 | 3 | 9900 | 52.1 | 2.00 | 122000 | 122000 | 644 | 3.51 |
| 113636 | 3 | 10100 | 53.2 | 4.00 | 108000 | 108000 | 571 | 3.94 |
| 113616 | 3 | 7740 | 40.7 | 2.00 | 125000 | NR | NR | NR |
| 113613 | 3 | 7310 | 38.5 | 2.00 | 53100 | 53100 | 280 | 6.36 |
| 113618 | 3 | 7000 | 36.8 | 2.00 | 75600 | 75600 | 398 | 3.23 |
| 112516 | 3 | 9820 | 51.7 | 4.00 | 90600 | 90600 | 477 | 3.69 |
| | Mean | 8650 | 45.5 | 2.67 | 95900 | 90000 | 474 | 4.15 |
| | SD | 1440 | 7.58 | 1.03 | 28200 | 27200 | 143 | 1.26 |

$AUC_{0-t}$ Area under the plasma concentration-time curve up to the last sampling time with measurable concentrations.
$AUC_{0-inf}$ Area under the plasma concentration-time curve up to infinity.
$AUC_{0-inf}/D$ Dose adjusted area under the plasma concentration-time curve up to infinity.
$C_{max}$ Maximum plasma concentration.
$C_{max}/D$ Dose adjusted maximum plasma concentration.
h Hours.
IR Immediate release.
NR Not reported.
SD Standard deviation.
$T_{max}$ Time to maximum concentration.
$t_{1/2}$ Observed elimination half-life.
XR Extended release.

The highest overall exposure of levetiracetam in dogs is achieved with the LEV XR and LEV IR formulations. Of the 190 mg Tablets A, B, and C, the highest overall exposure of levetiracetam in dogs is achieved with the 190 mg Tablet A. Based on the mean dose-adjusted plasma $C_{max}$ and $AUC_{0-inf}$ values, the levetiracetam exposure achieved with the 190 mg Tablet A is approximately 69% and 88%, respectively, of the exposure achieved with the LEV XR formulation, and 80% and 91%, respectively, of the exposure achieved with the LEV IR formulation.

Example 6: Evaluation of Extended Release Compositions of 220 mg Levetiracetam on Pharmacokinetics in Dogs Overview The purpose of this study is to collect samples for investigating the pharmacokinetics of novel extended release formulations of levetiracetam (220 mg) in male dogs following oral administration. Table 3 provides a description of the two formulations utilized in this study (220 mg Tablets D and E).

Animals

Eighteen non-naïve male purebred beagle dogs from the Covance Stock colony are used in these studies. The animals are acclimated to study conditions for approximately three days prior to dose administration. At dosing, the animals weigh 7.6 to 11.7 kg and are approximately 1 year of age. All animals are housed in individual, stainless steel cages during acclimation and the test period, except during periods of commingling in accordance with Covance SOPs. Certified Harlan Teklad 2021, 21% Protein Dog Diet is provided ad libitum unless otherwise specified for dose administration. Water is provided fresh daily, ad libitum. Environmental controls for the animal room are set to maintain a temperature of 68 to 79° F., a relative humidity of 50±20%, and a 12-hour light/12-hour dark cycle. As necessary, the 12-hour dark cycle is interrupted to accommodate study procedures.

Study Design

Three groups of dogs (N=6 per group) are utilized in this study. LEV XR is administered as a single oral dose of 500 mg. 220 mg Tablets D and E are administered as single oral doses of 220 mg. Plasma pharmacokinetic samples are collected at pre-dose (i.e., 0), 0.25, 0.5, 1, 2, 4, 6, 8, 12, 18, 24, and 48 hours post dose. See Table 7.

TABLE 7

Overview of Study Design

| Group | Number of Male Animals | Test Article | Dose Route | Target Dose Level (mg/tablet) |
|---|---|---|---|---|
| 1 | 6 | LEV-XR | Oral Tablet | 500 |
| 2 | 6 | Tablet D | Oral Tablet | 220 |
| 3 | 6 | Tablet E | Oral Tablet | 220 |

XR Extended Release.
Note:
Animals received a single tablet.

Analytical Methods

Sample analysis is performed using a Covance-owned generic method and analog internal standard. The method is adjusted as appropriate for the specific test article used on study. Data collection and chromatographic interpretation are performed in Analyst and the Laboratory Information Management System (LIMS) used on study is Watson.

Absorption and Plasma Levels

Figure 3:
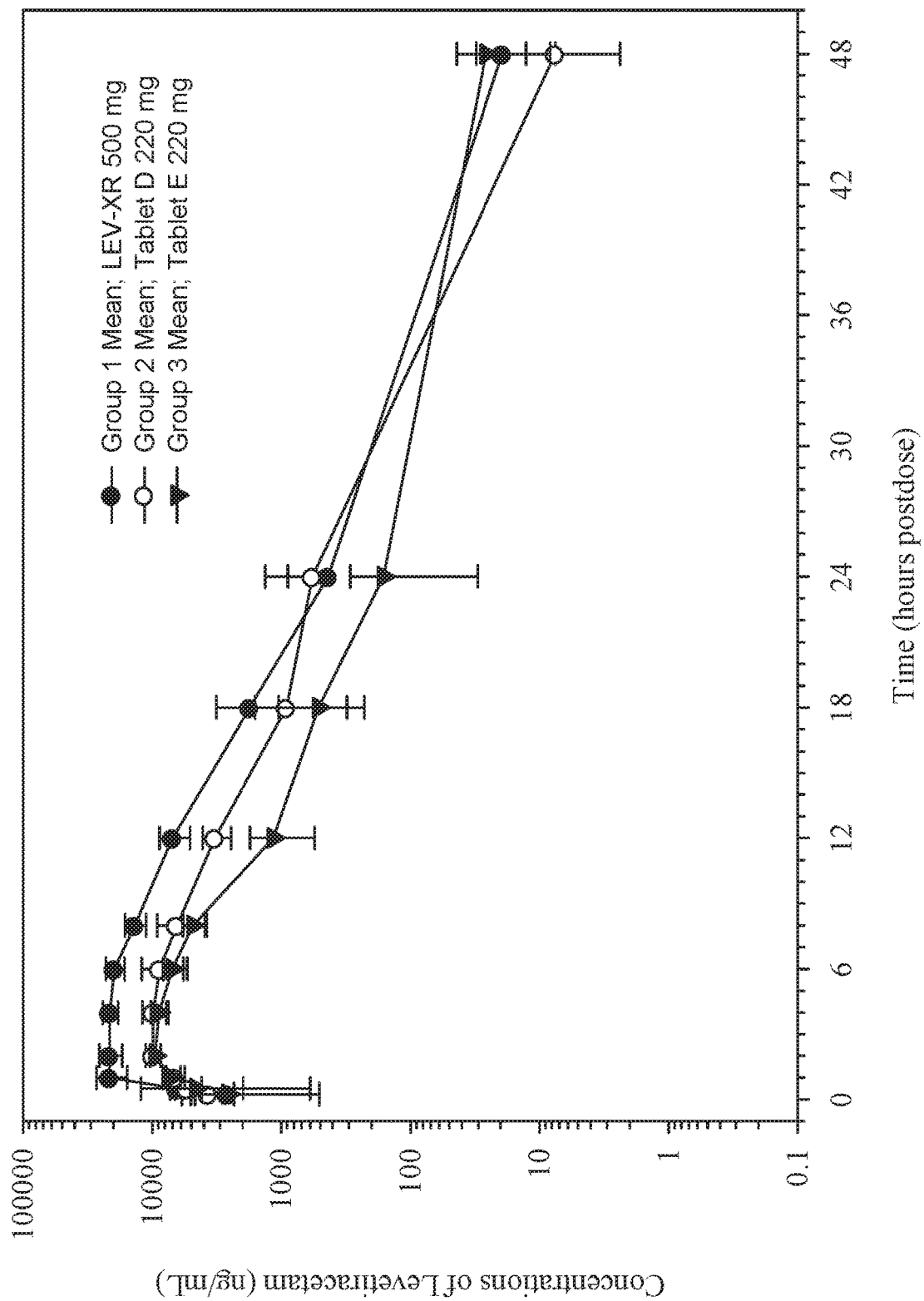
FIG. 3 shows the mean concentrations of different levetiracetam formulations in plasma following oral administration to male dogs. The tested levetiracetam formulations are: an extended release 500 mg levetiracetam tablet (LEV-XR) being administered as a single oral dose of 500 mg; the 220 mg Tablets D and E of Table 3 being administered as single oral doses of 220 mg.

LEV-XR is administered as a single oral tablet dose of 500 mg; the 220 mg Tablets D and E are each administered as single oral tablet doses of 220 mg. Based on mean dose-adjusted plasma $C_{max}$ and $AUC_{0-t}$, the overall exposure of dogs to levetiracetam is similar with the LEV-XR and the 220 mg Tablet D formulations (FIG. 3, Table 8).

LEV XR vs 220 mg Tablets

The plasma $C_{max}$ and $AUC_{0-inf}$ for the 220 mg Tablet D average 10900±2540 ng/mL and 110000±23000 ng·h/mL, respectively. The plasma $T_{max}$ generally ranges from 2.00 to 6.00 hours. The apparent elimination half-life of levetiracetam in plasma averages 4.41±0.06 h. The mean dose-adjusted plasma $C_{max}$ values are 46.6±7.37 and 49.3±11.5 ng/mL for the LEV-XR and the 220 mg Tablet D respectively. The dose-adjusted plasma $AUC_{0-t}$ values are 452±67.2 and 499±104 ng·h/mL for the LEV-XR and the 220 mg Tablet D, respectively.

The plasma $T_{max}$ is similar for LEV XR and the 220 mg Tablet D (LEV-XR: range 1.0-3.6 h; mean 1.6 h; the 220 mg Tablet D: range 2.0-6.0 h; mean 2.7 h). The apparent elimination half-life of levetiracetam in plasma averages 5.16±1.44 h and 4.41±0.614 h with the LEV-XR and the 220 mg Tablet D formulations, respectively.

TABLE 8

Pharmacokinetic parameters in plasma collected from male dogs following oral administration of Levetiracetam

| Group | Dose (mg) | Subject No. | $C_{max}$ (ng/mL) | $C_{max}$/D (ng/mL)/mg | $T_{max}$ (h) | $AUC_{0-t}$ (ng·h/mL) | $AUC_{0-t}$/D (ng·h/mL)/mg | $AUC_{0-inf}$ (ng·h/mL) | $t_{1/2}$ (h) |
|---|---|---|---|---|---|---|---|---|---|
| colspan=10 | | | | 500 mg (LEV-XR) | | | | | |
| 1 | 500 | 113637 | 25600 | 51.2 | 1.0 | 259000 | 518 | 259000 | 3.75 |
| 1 | 500 | 113638 | 23700 | 47.4 | 3.6 | 201000 | 402 | 201000 | 7.17 |
| 1 | 500 | 113639 | 28800 | 57.6 | 1.0 | 263000 | 526 | 263000 | 5.21 |
| 1 | 500 | 113641 | 19500 | 39.0 | 1.0 | 192000 | 384 | 192000 | 6.35 |
| 1 | 500 | 113642 | 19100 | 38.2 | 2.0 | 195000 | 390 | 196000 | 5.01 |
| 1 | 500 | 113647 | 23100 | 46.2 | 1.0 | 247000 | 494 | 247000 | 3.44 |
| | | N | 6 | 6 | 6 | 6 | 6 | 6 | 6 |
| | | Mean | 23300 | 46.6 | 1.6 | 226000 | 452 | 226000 | 5.16 |
| | | SD | 3680 | 7.37 | 1.1 | 33500 | 67.2 | 33400 | 1.44 |
| | | CV % | 15.8 | 15.8 | 66.1 | 14.8 | 14.9 | 14.8 | 28.0 |
| colspan=10 | | | | 220 mg (Tablet D) | | | | | |
| 2 | 220 | 113700 | 15300 | 69.5 | 6.0 | 142000 | 645 | 142000 | 4.65 |
| 2 | 220 | 113814 | 10400 | 47.3 | 2.0 | 108000 | 491 | 108000 | 3.91 |
| 2 | 220 | 113817 | 11400 | 51.8 | 2.0 | 130000 | 591 | NR | NR |
| 2 | 220 | 113832 | 10000 | 45.5 | 2.0 | 104000 | 473 | 104000 | 3.74 |
| 2 | 220 | 114110 | 10500 | 47.7 | 2.0 | 96100 | 437 | 96200 | 5.27 |
| 2 | 220 | 114111 | 7520 | 34.2 | 2.0 | 79000 | 359 | 79000 | 4.50 |
| | | N | 6 | 6 | 6 | 6 | 6 | 5 | 5 |
| | | Mean | 10900 | 49.3 | 2.7 | 110000 | 499 | 106000 | 4.41 |
| | | SD | 2540 | 11.5 | 1.6 | 23000 | 104 | 23200 | 0.614 |
| | | CV % | 23.4 | 23.4 | 61.2 | 20.9 | 20.8 | 21.9 | 13.9 |

$AUC_{0-t}$ Area under the plasma concentration-time curve up to the last sampling time with measurable concentrations.
$AUC_{0-inf}$ Area under the plasma concentration-time curve up to infinity.
$AUC_{0-inf}$/D Dose adjusted area under the plasma concentration-time curve up to infinity.
$C_{max}$ Maximum plasma concentration.
$C_{max}$/D Dose adjusted maximum plasma concentration.
CV % Coefficient of variation.
h Hours.
N Number of animals.
NR Not reported due to ill-defined terminal phase.
SD Standard deviation.
$T_{max}$ Time to maximum concentration.
$t_{1/2}$ Observed elimination half-life.

Based on the mean dose-adjusted plasma $C_{max}$ and $AUC_{0-t}$ values, the levetiracetam exposure achieved with the 220 mg Tablet D formulation is approximately 107% and 110%, respectively, of the exposure achieved with the LEV-XR formulation.

Example 7: Phase I Food Effect Study of Extended Release Compositions of 190 mg and 220 mg Levetiracetam This example describes a two-group, single-dose, two-period, two-way crossover, food-effect study of two extended release levetiracetam formulations, i.e., the 190 mg Tablet A of Table 1 and the 220 mg Tablet D of Table 3.

Objective

The objective of this study is to assess the effect of food on the rate and extent of absorption of two extended release levetiracetam formulations, i.e., the 190 mg Tablet A of Table 1 and the 220 mg Tablet D of Table 3.

Figure 6:
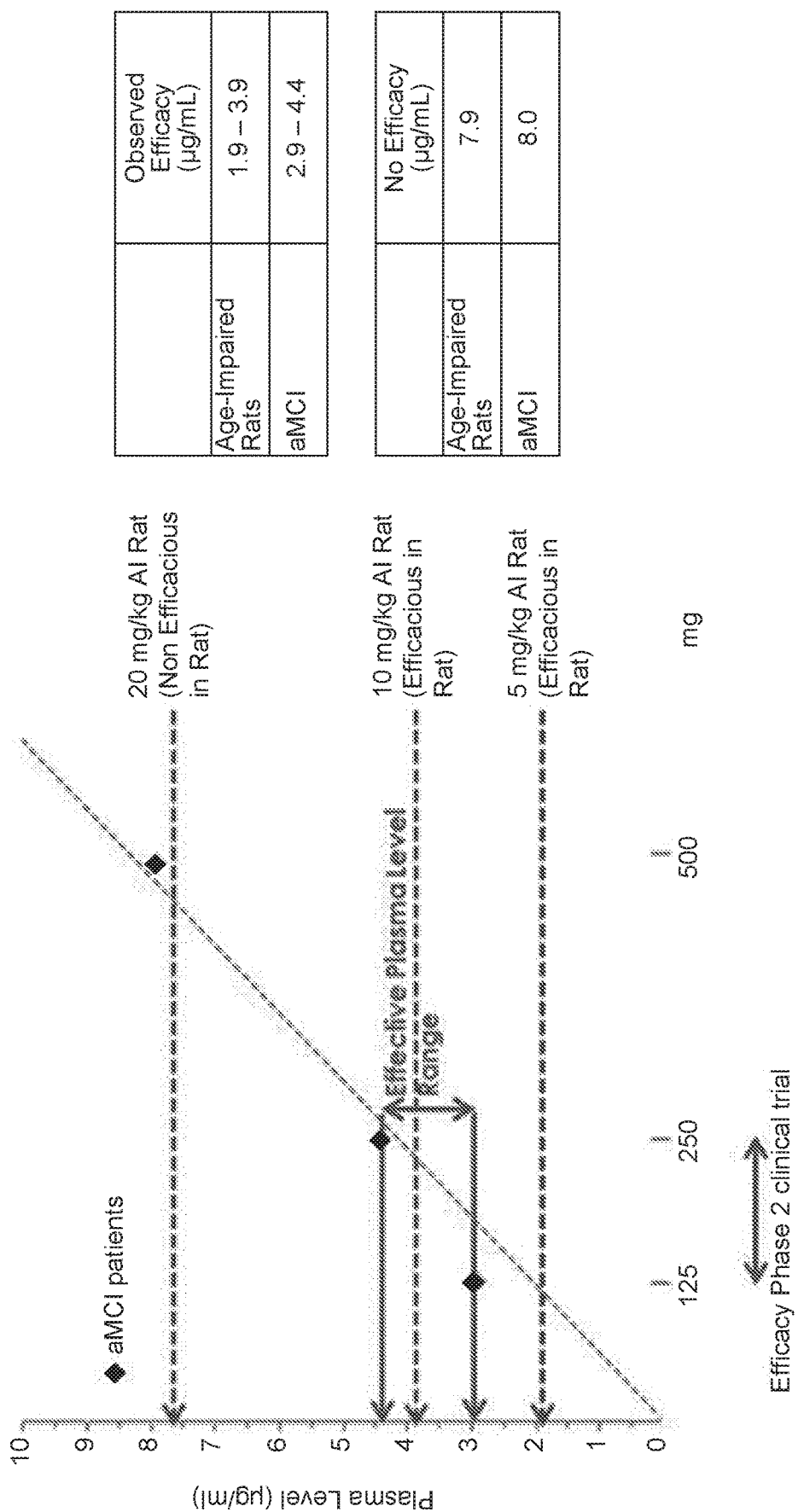
FIG. 6 shows the effective plasma level ranges based on Aged-Impaired rat studies and phase II study in aMCI patients. The acceptable range goal for the Phase I food effect study of the extended release formulations is established based on the effective plasma level range in aged-impaired rats and in aMCI patients, i.e., between 1.9 and 4.4 µg/ml. The preferred range goal for the Phase I food effect study of the extended release formulations is established based on the effective plasma level range in aMCI patients, i.e., between 2.9 and 4.4 µg/ml.

Steady state formulation goals: The preferred range goal is established based on aMCI phase II human study: between 2.9 and 4.4 µg/mL. The acceptable range goal is established based on Aged-Impaired (AI) rats and aMCI phase II human study: between 1.9 and 4.4 µg/mL. See FIG. 6.

Study Design

This is an open label, randomized, two-group, single-dose, two-period crossover, food-effect study. Fifty-six (56) healthy subjects are enrolled. Subjects who successfully complete the screening process check into the research center the evening before first dose. Subjects who continue to meet inclusion/exclusion criteria the morning of dose are assigned a subject number, based on the order in which they successfully complete the required screening process and procedures. Dosing days are separated by a washout period of at least 7 days.

Subjects are randomly assigned to one of two groups:

Group 1: Subjects (n=28) received extended-release Tablet A of Table 1 (190 mg).

Treatment A: Tablet A

Dose=1×190 mg tablet, orally administered under fasted conditions

Treatment B: Tablet A

Dose=1×190 mg tablet, orally administered under fed conditions

Group 2: Subjects (n=28) received extended-release Tablet D of Table 3 (220 mg).

Treatment A: Tablet D

Dose=1×220 mg tablet, orally administered under fasted conditions

Treatment B: Tablet D

Dose=1×220 mg tablet, orally administered under fed conditions

Fed treatment: Following an overnight fast of at least 10 hours, subjects began consuming a Food and Drug Administration (FDA) standard high-calorie, high-fat breakfast meal 30 minutes prior to administration of the study drug.

Fasted treatment: Subjects are dosed after an overnight fast of at least 10 hours.

Each drug administration is separated by a washout period of at least 7 days.

Each dose is orally administered along with approximately 240 mL (8 fl. oz.) of room temperature water. After dosing, no food is allowed until 4 hours postdose. Except for the 240 mL of room temperature water provided with the dose, no water might be consumed for 1 hour prior through 1 hour after dose. Water consumption followed the guidelines in Section 5.4.2. With the exception of the FDA standard high-calorie, high-fat breakfast meal served during the fed treatment period, meals are the same and scheduled at approximately the same times relative to dose for each study period.

Subjects who withdraw from the study are not replaced.

Clinical Procedures Summary

During each study period, 6 mL blood samples are obtained prior to each dosing and following each dose at selected times through 24 hours post-dose. A total of 34 pharmacokinetic blood samples are to be collected from each subject, 17 samples in each study period. In addition, blood is drawn and urine is collected for clinical laboratory testing at screening and study exit.

In each study period, subjects are admitted to the study unit in the evening prior to the scheduled dose. Subjects are confined to the research center during each study period until completion of the 24-hour blood collection and other study procedures.

Procedures for Collecting Samples for Pharmacokinetic Analysis

Blood samples (1×6 mL) are collected in vacutainer tubes containing $K_2$-EDTA as a preservative at pre-dose (0) and at 1.0, 2.0, 3.0, 4.0, 4.5, 5.0, 5.5, 6.0, 6.5, 7.0, 8.0, 9.0, 10, 12, 18, and 24 hours after dosing.

Bioanalytical Summary

Plasma samples are analyzed for levetiracetam using a validated LC-MS-MS procedure. The method is validated for a range of 0.0500 to 30.0 µg/mL for levetiracetam, based on the analysis of 0.200 mL of human EDTA plasma. Data are stored in Watson Laboratory Information Management System (LIMS; Version 7.2.0.03, Thermo Fisher Scientific).

Pharmacokinetic Analysis

Data are analyzed by noncompartmental methods in Win-Nonlin. Concentration-time data that are below the limit of quantification (BLQ) are treated as zero in the data summarization and descriptive statistics. In the pharmacokinetic analysis, BLQ concentrations are treated as zero from time-zero up to the time at which the first quantifiable concentration is observed; embedded and/or terminal BLQ concentrations are treated as "missing". Actual sample times are used for all pharmacokinetic and statistical analyses.

The following pharmacokinetic parameters are calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$). Additionally, $C_{max}$, $AUC_{last}$, and $AUC_{inf}$ are dose-normalized.

Analysis of variance (ANOVA) and the Schuirmann's two one-sided t-test procedures at the 5% significance level are applied to the log-transformed pharmacokinetic exposure parameters, $C_{max}$, $AUC_{last}$, and $AUC_{inf}$. The 90% confidence interval for the ratio of the geometric means (Test/Reference) is calculated. A lack of food effect is declared if the lower and upper confidence intervals of the log-transformed parameters are within 80% to 125% (190 mg Tablet A Fed vs. 190 mg Tablet A Fasted; 220 mg Tablet D Fed vs. 220 mg Tablet D Fasted). Additionally, the dose-normalized $C_{max}$, $AUC_{last}$, and $AUC_{inf}$ are compared within fasted and fed conditions to determine dose-proportionality. Dose-proportionality is concluded if the lower and upper confidence intervals of the dose-normalized, log-transformed parameters are within 80% to 125% (220 mg Tablet D Fasted vs. 190 mg Tablet A Fasted; 220 mg Tablet D Fed vs. 190 mg Tablet A Fed)

Results

Figure 4:
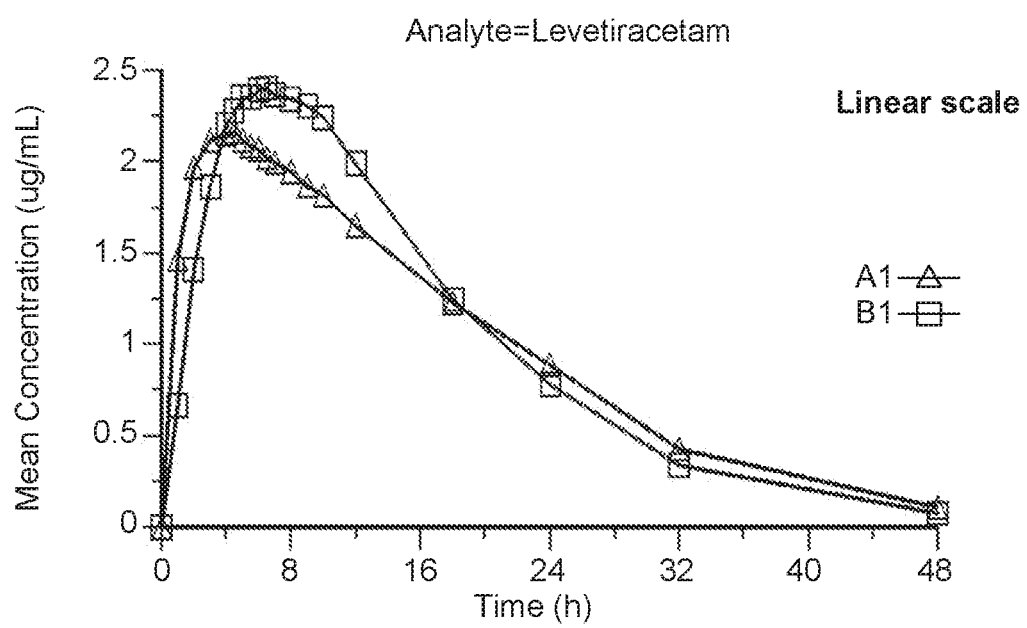
FIG. 4 shows the mean levetiracetam concentration-time profiles after administration of the 190 mg Tablet A of Table 1 under Fasted Conditions (Group 1/Treatment A: A1) and the 190 mg Tablet A of Table 1 under Fed Conditions (Group 1/Treatment B: B1).
Figure 4:
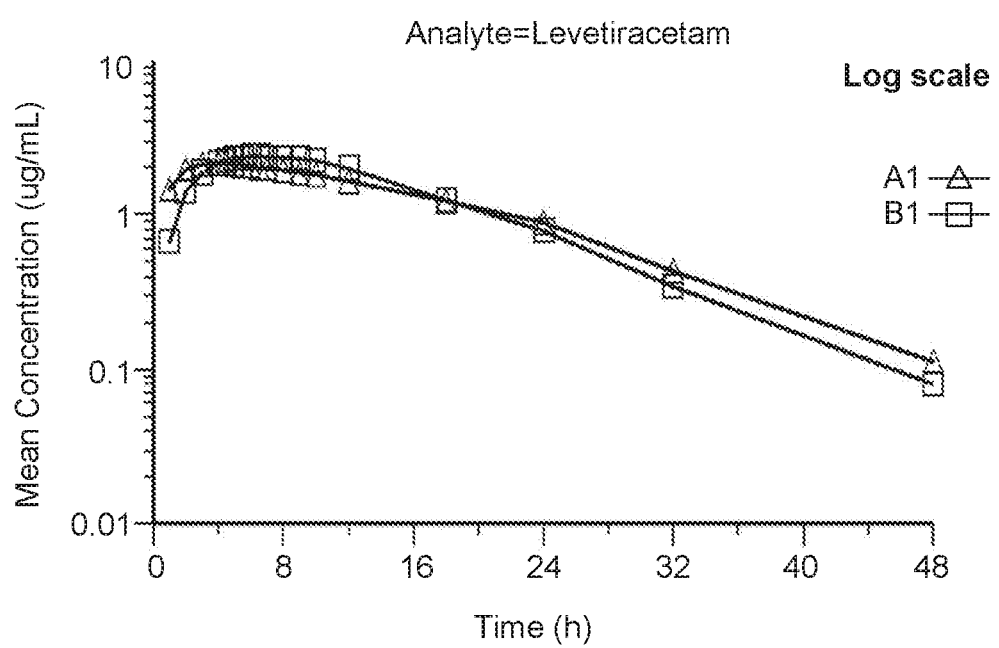
Figure 5:
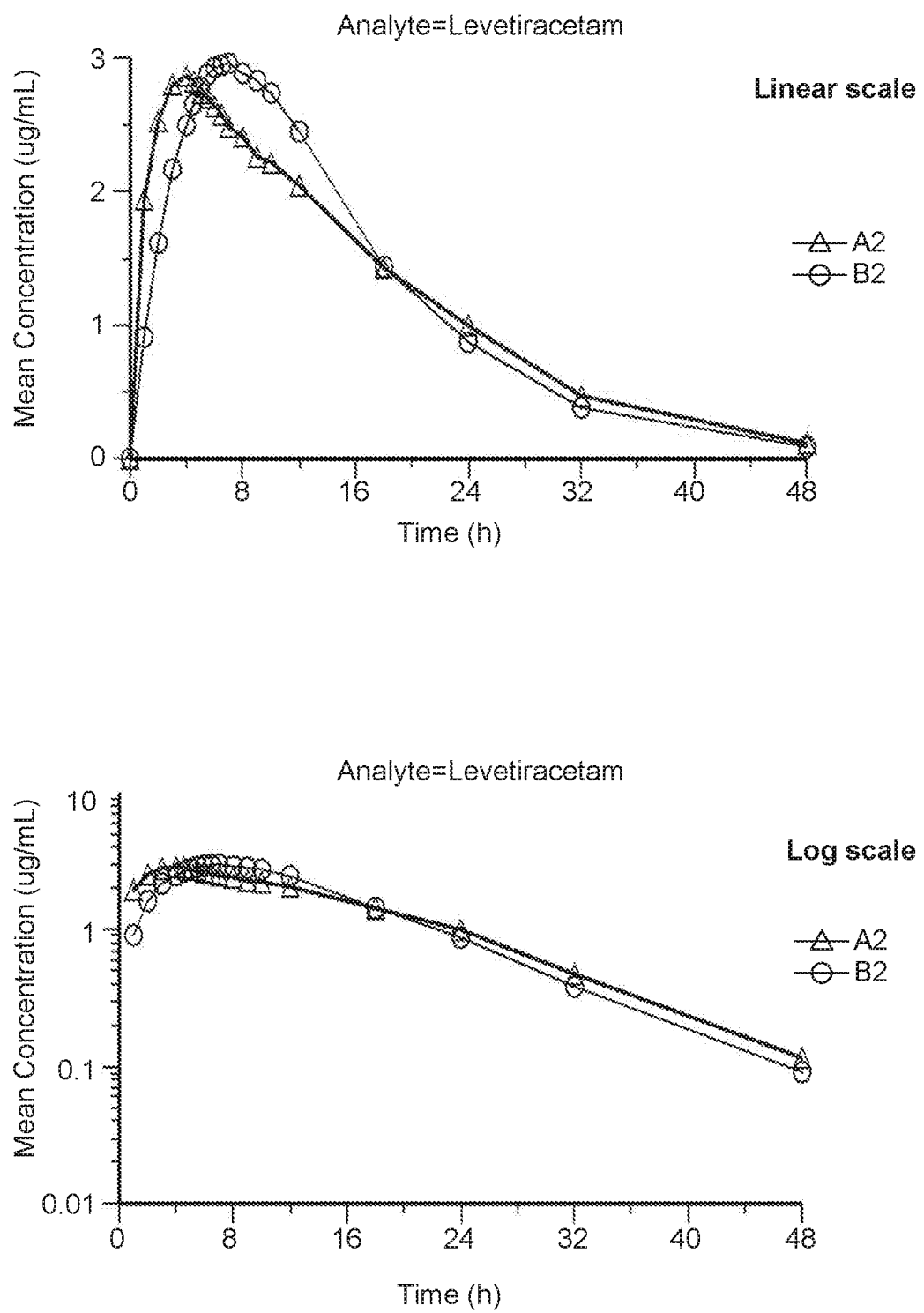
FIG. 5 shows the mean levetiracetam concentration-time profiles after administration of the 220 mg Tablet D of Table 3 under Fasted Conditions (Group 2/Treatment A: A2) and the 220 mg Tablet D of Table 3 under Fed Conditions (Group 2/Treatment B: B2).

Data from 55 subjects for Group 1 and 54 subjects for Group 2 are included in the pharmacokinetic and statistical analyses. Mean concentration-time data are shown in Tables 9 and 10 and in FIGS. 4 and 5. Results of the pharmacokinetic and statistical analyses are shown below in Tables 9-15.

Conclusions

Food-Effect:

The 90% confidence intervals for the log-transformed exposure parameters $C_{max}$, $AUC_{last}$, and $AUC_{inf}$ are within the 80% to 125% range for the 190 mg and 220 mg doses. The presence of food does not alter the pharmacokinetics of the 190 mg and 220 mg levetiracetam doses.

Dose Proportionality:

The 90% confidence intervals for the dose-normalized log-transformed exposure parameters $C_{max}/D$, $AUC_{last}/D$, and $AUC_{inf}/D$ are within the 80% to 125% range for fed and fasted conditions. Levetiracetam exposure, as measured by $C_{max}/D$, $AUC_{last}/D$, and $AUC_{inf}/D$, increase proportionately from 190 mg (Tablet A) to 220 mg (Tablet D).

Steady State Modeling

Figure 7:
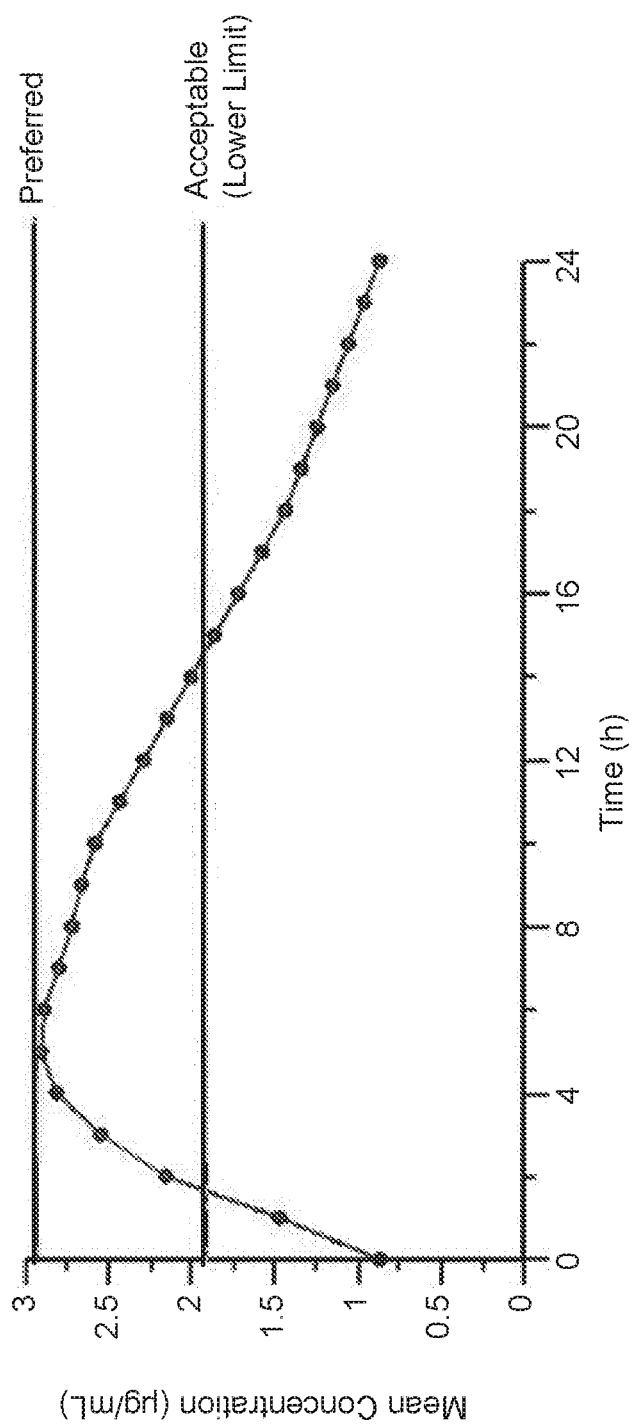
FIG. 7 shows the steady state modeling of the PK profile of the 190 mg Tablet A of Table 1, indicating that this tablet meets the acceptable range goal, i.e., between 1.9 and 4.4 µg/ml.

According to the steady state modeling of PK profile for the 190 mg Tablet A, it meets the acceptable range goal, i.e., between 1.9 and 4.4 µg/ml. See FIG. 7.

Figure 8:
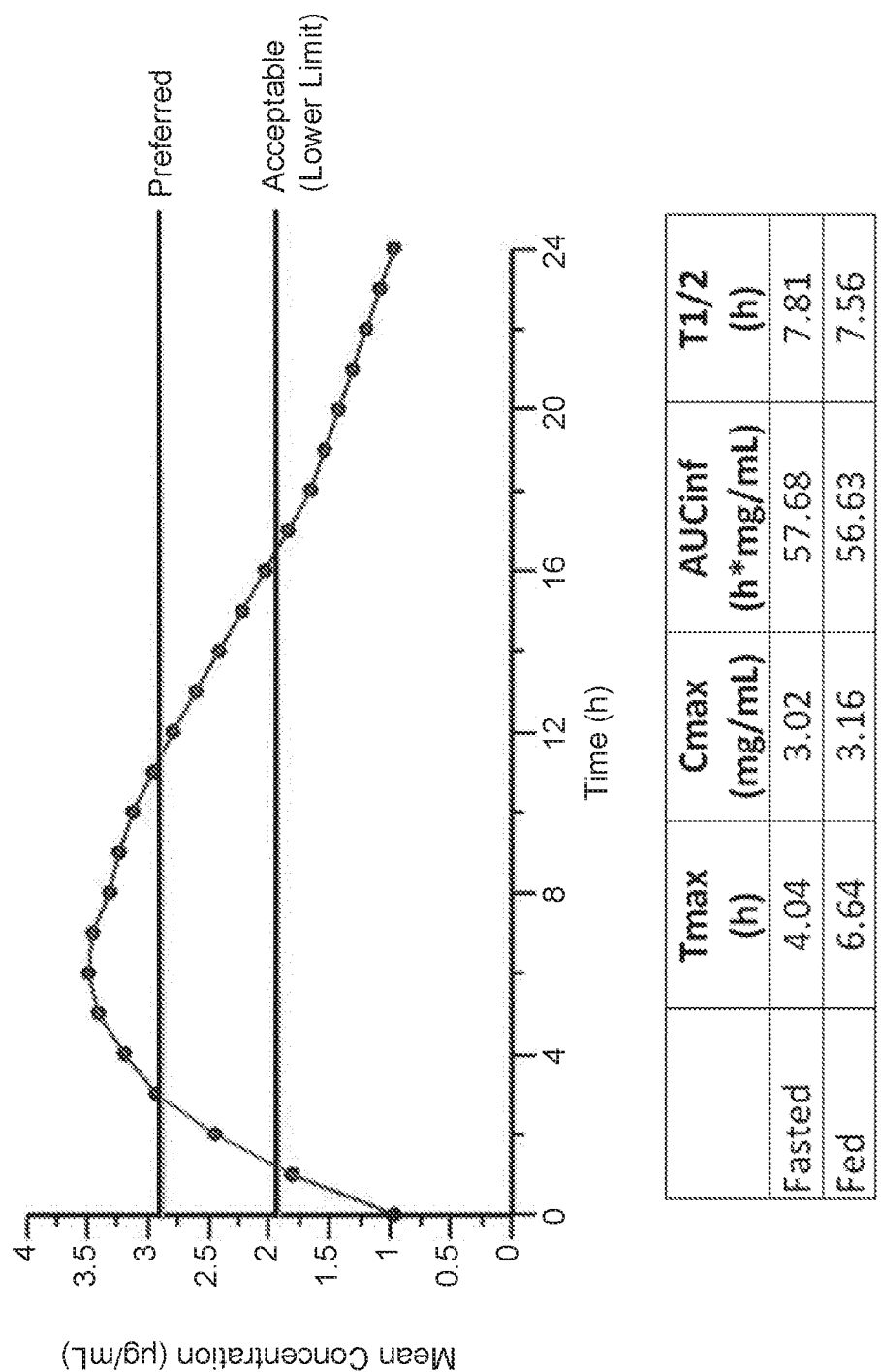
FIG. 8 shows the steady state modeling of the PK profile of the 220 mg Tablet D of Table 3, indicating that this tablet meets the preferred range goal, i.e., between 2.9 and 4.4 µg/ml.

According to the steady state modeling of PK profile for the 220 mg Tablet D, it meets the preferred range goal, i.e., between 2.9 and 4.4 µg/ml. See FIG. 8.

TABLE 9

Levetiracetam Concentration-Time Data after Administration of Extended-Release Tablet A, 190 mg under Fasted Conditions (Group 1/Treatment A) and Extended-Release Tablet A, 190 mg under Fed Conditions (Group 1/Treatment B)

| | Group 1/Treatment A: 190 mg Tablet A, Fasted | | | | Group 1/Treatment B: 190 mg Tablet A, Fed | | | |
|---|---|---|---|---|---|---|---|---|
| Time (h) | n | Mean (µg/mL) | SD (µg/mL) | CV (%) | n | Mean (µg/mL) | SD (µg/mL) | CV (%) |
| 0.00 | 28 | 0.00 | 0.00 | NC | 27 | 0.00 | 0.00 | NC |
| 1.00 | 28 | 1.46 | 0.450 | 30.76 | 27 | 0.665 | 0.351 | 52.82 |
| 2.00 | 28 | 1.96 | 0.535 | 27.21 | 27 | 1.41 | 0.454 | 32.20 |
| 3.00 | 28 | 2.11 | 0.548 | 25.93 | 27 | 1.86 | 0.391 | 21.03 |
| 4.00 | 28 | 2.15 | 0.569 | 26.53 | 27 | 2.19 | 0.443 | 20.25 |
| 4.50 | 28 | 2.16 | 0.549 | 25.42 | 27 | 2.27 | 0.469 | 20.70 |
| 5.00 | 28 | 2.11 | 0.508 | 24.08 | 27 | 2.34 | 0.500 | 21.35 |
| 5.50 | 28 | 2.08 | 0.497 | 23.91 | 27 | 2.34 | 0.519 | 22.15 |
| 6.00 | 28 | 2.06 | 0.445 | 21.61 | 27 | 2.38 | 0.514 | 21.58 |
| 6.50 | 28 | 2.02 | 0.445 | 22.07 | 27 | 2.39 | 0.516 | 21.57 |
| 7.00 | 28 | 1.99 | 0.437 | 21.97 | 27 | 2.36 | 0.472 | 20.04 |
| 8.00 | 28 | 1.94 | 0.451 | 23.20 | 27 | 2.34 | 0.517 | 22.13 |
| 9.00 | 28 | 1.86 | 0.440 | 23.64 | 27 | 2.30 | 0.543 | 23.64 |
| 10.00 | 28 | 1.81 | 0.464 | 25.58 | 27 | 2.24 | 0.568 | 25.41 |
| 12.00 | 28 | 1.65 | 0.402 | 24.42 | 27 | 1.98 | 0.471 | 23.74 |
| 18.00 | 28 | 1.23 | 0.339 | 27.62 | 27 | 1.24 | 0.306 | 24.63 |
| 24.00 | 28 | 0.888 | 0.272 | 30.68 | 27 | 0.783 | 0.212 | 27.07 |
| 32.00 | 28 | 0.431 | 0.140 | 32.52 | 27 | 0.342 | 0.0991 | 29.00 |
| 48.00 | 27 | 0.112 | 0.0517 | 46.22 | 27 | 0.0798 | 0.0442 | 55.39 |

Note:
Plasma samples analyzed using a bioanalytical method with a validated range 0.0500 to 30.0 µg/mL; concentrations reported in µg/mL to 3 significant figures; concentrations below limit of quantification set to zero (0.00 µg/mL) in the data summarization
NC = Not calculated

TABLE 10

Levetiracetam Concentration-Time Data after Administration of Extended-Release Tablet D, 220 mg under Fasted Conditions (Group 2/Treatment A) and Extended-Release Tablet D, 220 mg under Fed Conditions (Group 2/Treatment B)

| | Group 2/Treatment A: 220 mg Tablet D, Fasted | | | | Group 2/Treatment B: 220 mg Tablet D, Fed | | | |
|---|---|---|---|---|---|---|---|---|
| Time (h) | n | Mean (µg/mL) | SD (µg/mL) | CV (%) | n | Mean (µg/mL) | SD (µg/mL) | CV (%) |
| 0.00 | 26 | 0.00 | 0.00 | NC | 28 | 0.00 | 0.00 | NC |
| 1.00 | 26 | 1.94 | 0.619 | 31.91 | 28 | 0.911 | 0.681 | 74.77 |
| 2.00 | 26 | 2.53 | 0.645 | 25.53 | 28 | 1.61 | 0.636 | 39.41 |
| 3.00 | 26 | 2.80 | 0.618 | 22.08 | 28 | 2.16 | 0.560 | 25.89 |
| 4.00 | 26 | 2.86 | 0.596 | 20.83 | 28 | 2.49 | 0.558 | 22.36 |
| 4.50 | 26 | 2.83 | 0.553 | 19.57 | 28 | 2.65 | 0.506 | 19.07 |
| 5.00 | 26 | 2.73 | 0.501 | 18.33 | 28 | 2.78 | 0.454 | 16.35 |
| 5.50 | 26 | 2.70 | 0.499 | 18.47 | 28 | 2.87 | 0.474 | 16.49 |
| 6.00 | 26 | 2.64 | 0.487 | 18.44 | 28 | 2.93 | 0.448 | 15.32 |
| 6.50 | 26 | 2.58 | 0.444 | 17.23 | 28 | 2.94 | 0.532 | 18.07 |
| 7.00 | 26 | 2.48 | 0.444 | 17.88 | 28 | 2.96 | 0.471 | 15.92 |
| 8.00 | 26 | 2.41 | 0.444 | 18.44 | 28 | 2.88 | 0.456 | 15.82 |
| 9.00 | 26 | 2.26 | 0.428 | 18.93 | 28 | 2.83 | 0.523 | 18.47 |
| 10.00 | 26 | 2.22 | 0.409 | 18.45 | 28 | 2.74 | 0.587 | 21.45 |
| 12.00 | 26 | 2.04 | 0.382 | 18.68 | 28 | 2.45 | 0.678 | 27.69 |
| 18.00 | 26 | 1.43 | 0.299 | 20.95 | 28 | 1.44 | 0.373 | 25.90 |
| 24.00 | 26 | 0.998 | 0.243 | 24.39 | 28 | 0.873 | 0.261 | 29.87 |
| 32.00 | 26 | 0.472 | 0.138 | 29.17 | 28 | 0.382 | 0.139 | 36.41 |
| 48.00 | 26 | 0.116 | 0.0442 | 38.18 | 28 | 0.0913 | 0.0557 | 61.00 |

Note:
Plasma samples analyzed using a bioanalytical method with a validated range 0.0500 to 30.0 µg/mL; concentrations reported in µg/mL to 3 significant figures; concentrations below limit of quantification set to zero (0.00 µg/mL) in the data summarization
NC = Not calculated

TABLE 11

Pharmacokinetic Parameters of Levetiracetam

| | Group 1/Treatment A: 190 mg Tablet A, Fasted | | | | Group 1/Treatment B: 190 mg Tablet A, Fed | | | |
|---|---|---|---|---|---|---|---|---|
| Parameter | n | Mean | SD | CV % | n | Mean | SD | CV % |
| $T_{max}$ (h) | 28 | 4.39 | 2.05 | 46.71 | 27 | 6.93 | 1.97 | 28.50 |
| $C_{max}$ (µg/mL) | 28 | 2.31 | 0.505 | 21.83 | 27 | 2.53 | 0.528 | 20.86 |
| Cmax/D (µg/mL/mg) | 28 | 0.0122 | 0.00266 | 21.83 | 27 | 0.0133 | 0.00278 | 20.86 |
| $AUC_{last}$ (h * µg/mL) | 28 | 46.40 | 11.44 | 24.66 | 27 | 46.53 | 9.352 | 20.10 |
| AUClast/D (h * µg/mL/mg) | 28 | 0.2442 | 0.06024 | 24.66 | 27 | 0.2449 | 0.04922 | 20.10 |
| $AUC_{inf}$ (h * µg/mL) | 28 | 47.93 | 11.63 | 24.25 | 27 | 47.81 | 9.451 | 19.77 |

TABLE 11-continued

Pharmacokinetic Parameters of Levetiracetam

| Parameter | n | Mean | SD | CV % | n | Mean | SD | CV % |
|---|---|---|---|---|---|---|---|---|
| AUCinf/D (h * µg/mL/mg) | 28 | 0.2523 | 0.06119 | 24.25 | 27 | 0.2516 | 0.04974 | 19.77 |
| $AUC_{Extrap}$ (%) | 28 | 3.29 | 2.52 | 76.75 | 27 | 2.72 | 1.40 | 51.57 |
| $\lambda_z$ ($h^{-1}$) | 28 | 0.0873 | 0.0114 | 13.11 | 27 | 0.0911 | 0.0096 | 10.50 |
| $T_{1/2}$ (h) | 28 | 8.09 | 1.17 | 14.50 | 27 | 7.70 | 0.88 | 11.39 |
| $T_{last}$ (h) | 28 | 46.82 | 4.19 | 8.94 | 27 | 45.64 | 5.80 | 12.70 |
| $C_{last}$ (µg/mL) | 28 | 0.125 | 0.0661 | 52.74 | 27 | 0.115 | 0.0605 | 52.46 |

| | Group 2/Treatment A: 220 mg Tablet D, Fasted | | | | Group 2/Treatment B: 220 mg Tablet D, Fed | | | |
|---|---|---|---|---|---|---|---|---|
| Parameter | n | Mean | SD | CV % | n | Mean | SD | CV % |
| $T_{max}$ (h) | 26 | 4.04 | 1.25 | 30.91 | 28 | 6.64 | 1.83 | 27.55 |
| $C_{max}$ (µg/mL) | 26 | 3.02 | 0.569 | 18.88 | 28 | 3.16 | 0.623 | 19.73 |
| Cmax/D (µg/mL/mg) | 26 | 0.0137 | 0.00259 | 18.88 | 28 | 0.0143 | 0.00283 | 19.73 |
| $AUC_{last}$ (h * µg/mL) | 26 | 56.33 | 10.42 | 18.49 | 28 | 55.27 | 10.35 | 18.72 |
| AUClast/D (h * µg/mL/mg) | 26 | 0.2560 | 0.04734 | 18.49 | 28 | 0.2512 | 0.04702 | 18.72 |
| $AUC_{inf}$ (h * µg/mL) | 26 | 57.68 | 10.67 | 18.50 | 28 | 56.63 | 10.53 | 18.59 |
| AUCinf/D (h * µg/mL/mg) | 26 | 0.2622 | 0.04850 | 18.50 | 28 | 0.2574 | 0.04784 | 18.59 |
| $AUC_{Extrap}$ (%) | 26 | 2.35 | 1.10 | 47.03 | 28 | 2.42 | 1.19 | 48.97 |
| $\lambda_z$ ($h^{-1}$) | 26 | 0.0905 | 0.0123 | 13.63 | 28 | 0.0933 | 0.0126 | 13.50 |
| $T_{1/2}$ (h) | 26 | 7.81 | 1.14 | 14.59 | 28 | 7.56 | 1.01 | 13.32 |
| $T_{last}$ (h) | 26 | 48.01 | 0.06 | 0.13 | 28 | 45.73 | 5.71 | 12.48 |
| $C_{last}$ (µg/mL) | 26 | 0.116 | 0.0442 | 38.18 | 28 | 0.124 | 0.0640 | 51.46 |

TABLE 12

Statistical Analysis of the Natural Log-Transformed Systemic Exposure Parameters of Levetiracetam Comparing Extended-Release Tablet A, 190 mg under Fed Conditions (Treatment B1) to Extended-Release Tablet A, 190 mg under Fasted Conditions (Treatment A1) in Group 1

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $ln(C_{max})$ | 2.4777 | 2.2968 | 107.88 | 103.32 | 112.63 | 1.0000 | 9.29 |
| $ln(AUC_{last})$ | 45.6972 | 45.6427 | 100.12 | 95.44 | 105.02 | 1.0000 | 10.31 |
| $ln(AUC_{inf})$ | 46.9703 | 47.0059 | 99.92 | 95.38 | 104.68 | 1.0000 | 10.02 |

[a]Geometric Mean for 190 mg Tablet A, Fed (Test-B1) and 190 mg Tablet A, Fasted (Ref-A1) based on Least Squares Mean of log-transformed parameter values
[b]Ratio(%) = Geometric Mean (Test)/Geometric Mean (Ref)
[c]90% Confidence Interval

TABLE 13

Statistical Analysis of the Natural Log-Transformed Systemic Exposure Parameters of Levetiracetam Comparing Extended-Release Tablet D, 220 mg under Fed Conditions (Treatment B2) to Extended-Release Tablet D, 220 mg under Fasted Conditions (Treatment A2) in Group 2

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $ln(C_{max})$ | 3.1117 | 2.9660 | 104.91 | 100.32 | 109.72 | 1.0000 | 9.43 |
| $ln(AUC_{last})$ | 54.5598 | 55.6286 | 98.08 | 94.03 | 102.30 | 1.0000 | 8.86 |
| $ln(AUC_{inf})$ | 55.9406 | 56.9747 | 98.18 | 94.21 | 102.33 | 1.0000 | 8.71 |

[a]Geometric Mean for 220 mg Tablet D, Fed (Test-B2) and 220 mg Tablet D, Fasted (Ref-A2) based on Least Squares Mean of log-transformed parameter values
[b]Ratio(%) = Geometric Mean (Test)/Geometric Mean (Ref)
[c]90% Confidence Interval

TABLE 14

Statistical Analysis of the Natural Log-Transformed Systemic Exposure Dose-Normalized Parameters of Levetiracetam Comparing Extended-Release Tablet D, 220 mg under Fasted Conditions (Treatment A2) to Extended-Release Tablet A, 190 mg under Fasted Conditions (Treatment A1)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max}/D)$ | 0.0135 | 0.0119 | 113.39 | 102.88 | 124.98 | 0.9825 | 21.58 |
| $\ln(AUC_{last}/D)$ | 0.2518 | 0.2371 | 106.22 | 95.98 | 117.54 | 0.9754 | 22.49 |
| $\ln(AUC_{inf}/D)$ | 0.2579 | 0.2452 | 105.17 | 95.21 | 116.16 | 0.9789 | 22.07 |

[a]Geometric Mean for 190 mg Tablet A, Fasted (Test-A2) and 220 mg Tablet D, Fasted (Ref-A1) based on Least Squares Mean of log-transformed parameter values
[b]Ratio(%) = Geometric Mean (Test)/Geometric Mean (Ref)
[c]90% Confidence Interval

TABLE 15

Statistical Analysis of the Natural Log-Transformed Systemic Exposure Dose-Normalized Parameters of Levetiracetam Comparing Extended-Release Tablet D, 220 mg under Fed Conditions (Treatment B2) to Extended-Release Tablet D, 190 mg under Fed Conditions (Treatment B1)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max}/D)$ | 0.0141 | 0.0130 | 108.14 | 98.72 | 118.47 | 0.9906 | 20.41 |
| $\ln(AUC_{last}/D)$ | 0.2472 | 0.2404 | 102.82 | 94.49 | 111.89 | 0.9959 | 18.87 |
| $\ln(AUC_{inf}/D)$ | 0.2534 | 0.2472 | 102.51 | 94.32 | 111.42 | 0.9965 | 18.61 |

[a]Geometric Mean for 220 mg Tablet D, Fasted (Test-B2) and 220 mg Tablet D, Fasted (Ref-B1) based on Least Squares Mean of log-transformed parameter values
[b]Ratio(%) = Geometric Mean (Test)/Geometric Mean (Ref)
[c]90% Confidence Interval

What is claimed:

1. An extended release pharmaceutical composition comprising levetiracetam, wherein the composition provides a steady state plasma concentration of levetiracetam in a subject of between 1.9 µg/ml and 4.4 µg/ml within 3 hours after administration and extending for at least 8 hours of a 24-hour period after said administration.

2. The composition of claim 1, wherein the composition provides said steady state plasma concentration of levetiracetam within 2 hours after said administration and extending for at least 13 hours of a 24-hour period after said administration.

3. The composition of claim 1, wherein the composition provides said steady state plasma concentration of levetiracetam within 1 hour after said administration and extending for at least 13 hours of a 24-hour period after said administration.

4. An extended release pharmaceutical composition comprising levetiracetam, wherein the composition provides a steady state plasma concentration of levetiracetam in a subject of between 1.9 µg/ml and 4.4 µg/ml within 1 hour after administration and extending for at least 13 to 16 hours of a 24 hour period after said administration.

5. A method of improving cognition in a subject suffering from cognitive impairment or at risk thereof, wherein the method comprises administering the pharmaceutical composition of any one of claims 1-4.

6. The method of claim 5, wherein the subject suffers from cognitive impairment associated with a central nervous system (CNS) disorder or is at risk thereof.

7. The method of claim 5, wherein the cognitive impairment is associated with age-related cognitive impairment.

8. The method of claim 5, wherein the cognitive impairment is Mild Cognitive Impairment.

9. The method of claim 8, wherein the Mild Cognitive Impairment is amnestic Mild Cognitive Impairment.

10. The method of claim 5, wherein the cognitive impairment is associated with dementia, Alzheimer's disease, schizophrenia, amyotrophic lateral sclerosis, post traumatic stress disorder, cancer therapy, bipolar disorder, mental retardation, Parkinson's disease, autism, compulsive behavior, or substance addiction.

11. A method of treating mild cognitive impairment due to Alzheimer's disease in a human subject in need thereof, wherein the method comprises administering the pharmaceutical composition of any one of claims 1-4.

12. A method of treating amnestic mild cognitive impairment due to Alzheimer's disease in a human subject in need thereof, wherein the method comprises administering the pharmaceutical composition of any one of claims 1-4.

13. A method of slowing the progression of mild cognitive impairment due to Alzheimer's disease in a human subject in need thereof, wherein the method comprises administering the pharmaceutical composition of any one of claims 1-4.

14. A method of slowing the progression of amnestic mild cognitive impairment due to Alzheimer's disease in a human subject in need thereof, wherein the method comprises administering the pharmaceutical composition of any one of claims 1-4.

* * * * *